(12) United States Patent
Kishida et al.

(10) Patent No.: US 8,232,403 B2
(45) Date of Patent: Jul. 31, 2012

(54) BICYCLIC DERIVATIVES AS CETP INHIBITORS

(75) Inventors: Masashi Kishida, Ibaraki (JP); Naoko Matsuura, Tokyo (JP); Hidetomo Imase, Ibaraki (JP); Yuki Iwaki, Ibaraki (JP); Ichiro Umemura, Ibaraki (JP); Osamu Ohmori, Ibaraki (JP); Eiji Kawahara, Ibaraki (JP)

(73) Assignee: Novartis AG, Basel (CH)

( * ) Notice: Subject to any disclaimer, the term of this patent is extended or adjusted under 35 U.S.C. 154(b) by 819 days.

(21) Appl. No.: 12/300,208

(22) PCT Filed: May 8, 2007

(86) PCT No.: PCT/EP2007/004058
§ 371 (c)(1),
(2), (4) Date: Nov. 10, 2008

(87) PCT Pub. No.: WO2007/128568
PCT Pub. Date: Nov. 15, 2007

(65) Prior Publication Data
US 2009/0227580 A1  Sep. 10, 2009

Related U.S. Application Data

(60) Provisional application No. 60/866,480, filed on Nov. 20, 2006, provisional application No. 60/896,142, filed on Mar. 21, 2007.

(30) Foreign Application Priority Data

May 10, 2006 (GB) .................................. 0609268.8

(51) Int. Cl.
*A61K 31/47* (2006.01)
*C07D 215/46* (2006.01)
(52) U.S. Cl. ........................................ 546/162; 514/313
(58) Field of Classification Search .................. None
See application file for complete search history.

(56) References Cited

U.S. PATENT DOCUMENTS

| | | | |
|---|---|---|---|
| 2003/0096818 A1 | 5/2003 | Sikorski et al. | |
| 2003/0105081 A1 | 6/2003 | Yohannes et al. | |
| 2005/0059810 A1 | 3/2005 | Maeda et al. | |
| 2005/0085497 A1 | 4/2005 | Ahmad et al. | |
| 2006/0178514 A1 | 8/2006 | Baruah et al. | |
| 2009/0075968 A1 | 3/2009 | Sakaki et al. | |
| 2009/0181929 A1 | 7/2009 | Konishi et al. | |
| 2010/0041705 A1 | 2/2010 | Imase et al. | |
| 2010/0076021 A1 | 3/2010 | Imase et al. | |

FOREIGN PATENT DOCUMENTS

| | | |
|---|---|---|
| EP | 1 533 292 B1 | 5/2005 |
| EP | 1533292 | 5/2005 |
| WO | 2004/043925 | 5/2004 |
| WO | 2004/043925 A2 | 5/2004 |
| WO | 2004/085401 | 10/2004 |
| WO | 2004/085401 A1 | 10/2004 |
| WO | 2005/100298 | 10/2005 |
| WO | 2005/100298 A1 | 10/2005 |
| WO | 2006/056854 | 6/2006 |
| WO | 2006/056854 A1 | 6/2006 |
| WO | 2006/056881 | 6/2006 |
| WO | 2006/056881 A1 | 6/2006 |
| WO | 2006/073973 | 7/2006 |
| WO | 2006/073973 A2 | 7/2006 |
| WO | 2006/733973 A | 7/2006 |
| WO | 2007/075194 A | 7/2007 |
| WO | 2007/088999 A | 8/2007 |

OTHER PUBLICATIONS

"The Organic Chemistry of Drug Design and Drug Action," 2004, Elsevier, pp. 29-32.*
Davidson, J. Clin. Lipidol. 2010 vol. 4, pp. 394-398.*
Cappelli, et al., "Structure—Activity Relationships in carboxamide Derivatives Based on targeted Delivery of Radionuclides and Boron Atoms by Means of peripheral benzodiazepine receptor ligands" Journal of medicinal chemistry, 46(17), 3568-3571. (2003).
Anzini, et al., "Mapping and fitting the peripheral benzodiazepine receptor binding site by carboxamide derivatives. Comparison of different approaches to quantitative ligand—receptor interaction modeling" Journal of medicinal chemistry, 44(8), 1134-1150. (2001).
Leost, Francoise, et al: "Tandem Wolff rearrangement- .alpha.-cyclization of tertiary amines sequence: synthesis of some 1H-2-benzopyran derivatives" Tetrahedon, 54(23), 6457-6474 CODEN: TETRAB; ISSN: 0040-4020, 1998, XP004119590. Compound 11G.
Sculley, John D. et al: "Some amide derivatives of certain aminomethylpyridines" Journal of the American Chemical Society, 75, 3400-3 CODEN: JACSAT; ISSN: 0002-7863, 1953, XP002998573. Compound VII.
Liu, Luping, et al: SAR of 3,4-Dihydropyrido[3,2-d]pyrimidone p38 inhibitors Bioorganic & Medicinal Chemistry Letters, 13(22), 3979-3982 CODEN: BMCLE8; ISSN: 0960-894X, 2003, XP002428782. Compound 8.
Natarajan, Swaminathan R. et al: 'p38 MAP kinase inhibitors. Part 3: SAR on 3,4-dihydropyrimido[4,5-d] pyrimidin-2-ones and 3,4-dihydropyrido[4,3-d]pyrimidin-2-ones Bioorganic & Medicinal Chemistry Letters, 16(16), 4400-4404 CODEN: BMCLE8; ISSN: 0960-894X, 2006, XP005544088. Compound 49.

* cited by examiner

*Primary Examiner* — Janet Andres
*Assistant Examiner* — Heidi Reese
(74) *Attorney, Agent, or Firm* — Sophie Binet Cross

(57) ABSTRACT

The present invention relates to novel compounds of formula (I)

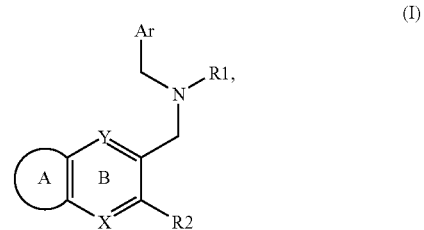

or a pharmaceutical composition thereof, with all the variables being defined in the text. The present invention further relates to the use of the compounds herein for treatment of or delay progression to overt to diseases in which CETP is involved.

10 Claims, No Drawings

BICYCLIC DERIVATIVES AS CETP INHIBITORS

This application is the National Stage of Application No. PCT/EP2007/004058, filed on Aug. 29, 2006, which claims benefit under 35 U.S.C. §119(a)-(d) or (f) or 365(b) of GB Application No. 0609268.8, filed May 10, 2006, and benefit under 35 U.S.C. §119(e) of U.S. Provisional Applications No. 60/866,480, filed Nov. 20, 2006, and 60/896,142, filed Mar. 21, 2007, the contents of which are incorporated herein by reference in their entirety.

The present invention relates to novel compounds of formula (I)

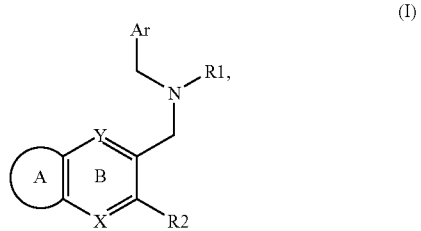

wherein
the ring A, which is annellated to ring B, represents an unsubstituted or substituted carbocyclic aromatic radical; or an unsubstituted or substituted heterocyclic moiety;
wherein Ar represents an unsubstituted or substituted carbocyclic aromatic radical;
$R_1$ is the element —C(=O)—$R_3$, —C(=O)—O—$R_3$, —C(=O)—$NR_4R_5$, —S(O)$_m$—$R_3$, —S(O)$_m$—N($R_4$)($R_5$), m being in each case the integer 0, 1 or 2, or $R_1$ is Z;
$R_2$ is selected from the group consisting of —CN, —$OR_3$, —$COR_3$, —C(=O)—O—$R_3$, —C(=O)—$NR_4R_5$, —N($R_4$)($R_5$), —S(O)$_m$($R_3$, —S(O)$_m$—N($R_4$)($R_5$) and —$NR_3$—S(O)$_m$—N($R_4$)($R_5$), m being in each case the integer 0, 1 or 2, or $R_2$ is Z;
wherein, in each case, independently of one another,
Z is selected from the group consisting of (i) unsubstituted or substituted monocyclic cycloalkyl or unsubstituted or substituted monocyclic cycloalkenyl, (ii) unsubstituted or substituted carbocyclic aromatic radical or unsubstituted or substituted heterocyclic radical;
$R_3$, independently, represents hydrogen, alkyl, haloalkyl, unsubstituted or substituted cycloalkyl, unsubstituted or substituted cycloalkenyl, in the cycloalkyl moiety unsubstituted or substituted cycloalkyl-alkyl, in the cycloalkenyl moiety unsubstituted or substituted cycloalkenyl-alkyl, unsubstituted or substituted carbocyclic aromatic radical, unsubstituted or substituted heterocyclic radical or in the aryl moiety unsubstituted or substituted aralkyl;
$R_4$ and $R_5$, independently of one another, represents hydrogen, alkyl, alkyl which is substituted by one or more substituents selected from the group consisting of halogen, hydroxy, —N($R_4$)($R_5$), —C(=O)—O—$R_3$, —C(=O)—$NR_4R_5$, —S(O)$_m$—$R_3$, —S(O)$_m$—N($R_4$)($R_5$), unsubstituted or substituted cycloalkyl, unsubstituted or substituted cycloalkenyl, and unsubstituted or substituted heterocyclic radical; or $R_4$ and $R_5$, independently of one another, represents unsubstituted or substituted cycloalkyl or unsubstituted or substituted cycloalkenyl, or unsubstituted or substituted carbocyclic aromatic radical, of unsubstituted or substituted heterocyclic radical;
$R_4$ and $R_5$ together are unsubstituted or substituted alkylene or unsubstituted or substituted alkylene that is interrupted by O, $NR_3$' or S; $R_3$' being $R_3$ or —C(=O)—$OR_3$; and
wherein in case of radicals $R_4$ and $R_5$ relating to $R_1$, $R_4$ and $R_5$ represents hydrogen;
m is the integer 0, 1 or 2;
X is $CR_6$ or N and Y is N; or X is N and Y is $CR_6$;
$R_6$ is hydrogen, halogen, $NO_2$, CN, OH, alkyl, alkoxy-alkyl, hydroxy-alkyl, halo-alkyl, alkoxy, alkoxy-alkoxy, haloalkoxy, —C(=O)—$R_3$, —C(=O)—O—$R_3$, —N($R_4$)($R_5$), —C(=O)—$NR_4R_5$, —S(O)$_m$—$R_3$, —S(O)$_m$—N($R_4$)($R_5$), —$NR_3$—S(O)$_m$—N($R_4$)($R_5$), m being in each case the integer 0, 1 or 2; alkanoyl, unsubstituted or substituted cycloalkyl, unsubstituted or substituted cycloalkenyl; in the aryl moiety unsubstituted or substituted aralkyl and in the heterocyclyl moiety unsubstituted or substituted heterocyclyl-alkyl; and
wherein substituted cycloalkyl or substituted cycloalkenyl each of which substituted is by one or more substituents selected from the group consisting of alkyl, of alkoxy, of —C(=O)—O—$R_3$, of —C(=O)—$NR_4R_5$, of —N($R_4$)($R_5$), of cycloalkyl-alkyl, of unsubstituted or substituted carbocyclic aromatic radical, of unsubstituted or substituted heterocyclic radical, of in the aryl moiety unsubstituted or substituted aralkyl, and of in the heterocyclyl moiety unsubstituted or substituted heterocyclyl-alkyl; and
wherein a carbocyclic aromatic radical or a heterocyclic aromatic radical or a heterocyclic radical, in the aryl moiety unsubstituted or substituted aralkyl, in the heterocyclyl moiety unsubstituted or substituted heterocyclyl-alkyl, or the rings A or Ar, independently of one another, are unsubstituted or substituted by one or more substituents selected from the group consisting of halogen, $NO_2$, CN, OH, alkyl, alkoxy-alkyl, hydroxy-alkyl, halo-alkyl, alkoxy, alkoxy-alkoxy, haloalkoxy, —C(=O)—$R_3$, —C(=O)—O—$R_3$, —N($R_4$)($R_5$), —C(=O)—$NR_4R_5$, —S(O)$_m$—$R_3$, —S(O)$_m$—N($R_4$)($R_5$), —$NR_3$—S(O)$_m$—N($R_4$)($R_5$) and alkanoyl, m being in each case the integer 0, 1 or 2; and unsubstituted or substituted cycloalkyl, unsubstituted or substituted cycloalkenyl; in the aryl moiety unsubstituted or substituted aralkyl and in the heterocyclyl moiety unsubstituted or substituted heterocyclyl-alkyl;
in free form or in salt form,
to a process for the preparation of these compounds, to the use of these compounds and to pharmaceutical preparations containing such a compound (I) in free form or in the form of a salt, especially a pharmaceutically acceptable salt.

In one embodiment, the present invention relates to the novel compounds of formula (I):

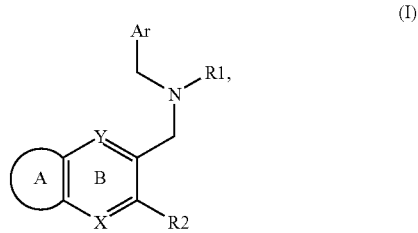

wherein the ring A, which is annellated to ring B, represents an unsubstituted or substituted carbocyclic aromatic radical or an unsubstituted or substituted heterocyclic aromatic radical;

wherein Ar represents an unsubstituted or substituted carbocyclic aromatic radical;

$R_1$ is the element —C(=O)—$R_3$, —C(=O)—O—$R_3$, —C(=O)—$NR_4R_5$, —S(O)$_m$—$R_3$, —S(O)$_m$—N($R_4$)($R_5$), m being in each case the integer 0, 1 or 2, or $R_1$ is Z, Z is selected from the group consisting of (i) unsubstituted or substituted monocyclic cycloalkyl or unsubstituted or substituted monocyclic cycloalkenyl, (ii) unsubstituted or substituted carbocyclic aromatic radical or unsubstituted or substituted heterocyclic radical;

$R_2$ is selected from the group consisting of —C(=O)$R_3$, —C(=O)—O—$R_3$, —N($R_4$)($R_5$), —S(O)$_m$—N($R_4$)($R_5$) and —$NR_3$—S(O)$_m$—N($R_4$)($R_5$), m being in each case the integer 0, 1 or 2;

$R_3$, independently, represents hydrogen, alkyl, haloalkyl, unsubstituted or substituted cycloalkyl, unsubstituted or substituted cycloalkenyl, in the cycloalkyl moiety unsubstituted or substituted cycloalkyl-alkyl, in the cycloalkenyl moiety unsubstituted or substituted cycloalkenyl-alkyl, unsubstituted or substituted carbocyclic aromatic radical, unsubstituted or substituted heterocyclic radical or in the aryl moiety unsubstituted or substituted aralkyl;

$R_4$ and $R_5$, independently of one another, represents hydrogen, alkyl, which is substituted by one or more substituents selected from the group consisting of unsubstituted or substituted cycloalkyl, unsubstituted or substituted cycloalkenyl, and unsubstituted or substituted heterocyclic radical;

$R_7$ and $R_8$, independently of one another, represents unsubstituted or substituted cycloalkyl, unsubstituted or substituted cycloalkenyl, or unsubstituted or substituted carbocyclic aromatic radical, of unsubstituted or substituted heterocyclic radical; or $R_4$ and $R_5$ together are unsubstituted or substituted alkylene or unsubstituted or substituted alkylene that is interrupted by O, $NR_3'$ or S; $R_3'$ being $R_3$ or —C(=O)—O$R_3$; and m is the integer 0, 1 or 2;

X is $CR_6$ or N and Y is N; or X is N and Y is $CR_6$;

$R_6$ is hydrogen, halogen, $NO_2$, CN, OH, alkyl, alkoxy-alkyl, hydroxy-alkyl, halo-alkyl, alkoxy, alkoxy-alkoxy, haloalkoxy, —C(=O)—$R_3$, —C(=O)—O—$R_3$, —N($R_4$)($R_5$), —C(=O)—$NR_4R_5$, —S(O)$_m$—$R_3$, —S(O)$_m$—N($R_4$)($R_5$), —$NR_3$—S(O)$_m$—N($R_4$)($R_5$), m being in each case the integer 0, 1 or 2; alkanoyl, unsubstituted or substituted cycloalkyl, unsubstituted or substituted cycloalkenyl; in the aryl moiety unsubstituted or substituted aralkyl and in the heterocyclyl moiety unsubstituted or substituted heterocyclyl-alkyl; and wherein substituted cycloalkyl or substituted cycloalkenyl or substituted alkylene, each of which is substituted by one or more substituents selected from the group consisting of alkyl, alkoxy, —C(=O)—O—$R_3$, —C(=O)—N(alkyl)(alkyl), —N(alkyl)(alkyl), $H_2$N—C(=O)—, $H_2$N—C(=O)-alkyl—, formyl, formyl-alkyl—, cycloalkyl-alkyl, carbocyclic aromatic radical, heterocyclic radical, aralkyl, and heterocyclyl-alkyl; and wherein a carbocyclic aromatic radical or a heterocyclic aromatic radical or a heterocyclic radical, in the aryl moiety unsubstituted or substituted aralkyl, in the heterocyclyl moiety unsubstituted or substituted heterocyclyl-alkyl, or the rings A or Ar, independently of one another, are unsubstituted or substituted by one or more substituents selected from the group consisting of halogen, $NO_2$, CN, OH, alkyl, alkoxy-alkyl, hydroxy-alkyl, halo-alkyl, alkoxy, alkoxy-alkoxy, haloalkoxy, —C(=O)—$R_3$, —C(=O)—O—$R_3$, —N($R_4$)($R_5$), —C(=O)—$NR_4R_5$, —S(O)$_m$—$R_3$, —S(O)$_m$—N($R_4$)($R_5$), —$NR_3$—S(O)$_m$—N($R_4$)($R_5$) and alkanoyl, m being in each case the integer 0, 1 or 2; and unsubstituted or substituted cycloalkyl, unsubstituted or substituted cycloalkenyl; in the aryl moiety unsubstituted or substituted aralkyl and in the heterocyclyl moiety unsubstituted or substituted heterocyclyl-alkyl;

in free form or in salt form, or a salt thereof.

The compounds (I) can be present as salts, in particular pharmaceutically acceptable salts. If the compounds (I) have, for example, at least one basic centre, they can form acid addition salts. The compounds (I) having at least one acid group can also form salts with bases. Salts which are unsuitable for pharmaceutical uses but which can be employed, for example, for the isolation or purification of free compounds (I) or their pharmaceutically acceptable salts, are also included. In view of the close relationship between the novel compound in the free form and in the form of its salts, in the preceding text and below the free compound or its salts may correspondingly and advantageously also be understood as meaning the corresponding salts or the free compound.

Salts are especially the pharmaceutically acceptable salts of compounds of formula (I) or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as base addition salts, preferably with organic or inorganic bases, from compounds of formula (I) or any of the intermediates mentioned herein with an acidic carboxy group, especially the pharmaceutically acceptable salts. Suitable metal ions from inorganic bases are, for example, alkaline or alkaline earth metals, such as sodium, potassium, magnesium or calcium salts. Suitable organic bases are, for example, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

In the presence of positively charged radicals, such as amino, salts may also be formed with acids. Such salts are formed, for example, as acid addition salts, preferably with organic or inorganic acids. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

When a basic group and an acid group are present in the same molecule, a compound of formula (I) or any of the intermediates mentioned herein may also form internal salts.

For isolation or purification purposes of compounds of the formula (I) or in general for any of the intermediates mentioned herein it is also possible to use pharmaceutically unacceptable salts, for example picrates or perchlorates. For therapeutic use, only pharmaceutically acceptable salts or free compounds of the formula (I) are employed (where applicable comprised in pharmaceutical preparations), and these are therefore preferred at least in the case of compounds of the formula (I).

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula (I), is to be understood as referring also to one or more salts thereof or a mixture of a corresponding free compound, intermediate or starting material and one or more salts thereof, each of which is intended to include also any solvate, metabolic precursor such as ester or amide of the compound of formula (I), or salt of any one or more of these, as appropriate and expedient and if not explicitly mentioned otherwise. Different crystal forms may be obtainable and then are also included.

For purposes of interpreting this specification, the following definitions will apply and whenever appropriate, terms used in the singular will also include the plural and vice versa.

The general definitions used above and below, unless defined differently, have the following meanings:

If not defined otherwise, alkyl being a radical or part of a radical is especially $C_1$-$C_7$-alkyl, preferably $C_1$-$C_4$-alkyl. Alkyl is a straight-chained or branched (one or, if desired and possible, more times), which has up to 20 carbon atom and is more preferably $C_1$-$C_7$-alkyl. The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

Unsubstituted or substituted aryl(carbocyclic aromatic radical) is preferably a mono- or polycyclic, especially monocyclic, bicyclic or tricyclic aryl moiety with 6 to 22 carbon atoms, especially phenyl or naphthyl, and is unsubstituted or substituted by one or more, especially one to three, moieties, preferably independently selected from the group consisting of $C_1$-$C_7$-alkyl, especially methyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, especially methoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, N-mono- or N,N-di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycarbonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfo, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl, nitro and heterocyclyl, especially morphilinyl. More preferred aryl substituents are selected from the from the group consisting of $C_1$-$C_7$-alkyl, especially methyl, halo, especially fluoro, chloro, bromo or iodo, $C_1$-$C_7$-alkoxy, especially methoxy, N-mono- or N,N-di-($C_1$-$C_7$-alkyl)-amino, N-mono- or N,N-di-($C_1$-$C_7$-alkyl)-aminocarbonyl, carboxy, cyano and heterocyclyl, especially morphilinyl. A carbocyclic aromatic radical is, in particular, phenyl, biphenylyl or naphthyl. Biphenylyl is, for example, 4-biphenylyl, and also a 2- or 3-biphenylyl. Naphthyl is 1- or 2-naphthyl.

A heterocyclic radical is, in particular, a heteroaryl which is a 5-14 membered monocyclic- or bicyclic- or fused polycyclic-ring system, having 1 to 8 heteroatoms selected from N, O or S. Preferably, the heteroaryl is a 5-10 membered ring system. A heterocyclic aromatic radical group may be mono-, bi-, tri-, or polycyclic, preferably mono-, bi-, or tricyclic, more preferably mono- or bicyclic. A heterocyclic radical can also be a partially or fully saturated heteroaryl.

A heterocyclic radical is, in particular, an unsubstituted or substituted 5- to 6-membered heterocyclic ring having 1, 2, 3 or 4 hetero atoms selected from the group consisting of N, S and O.

A heterocyclic radical is, in particular, an unsubstituted or substituted benzofused heterocyclic ring having 1 or 2 hetero atoms selected from the group consisting of N, S and O, and the heterocyclic ring being saturated or having 1 or 2 double bonds Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

A heterocyclic aromatic radical is also a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH-carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

An appropriate 5- or 6-membered and monocyclic radical which has up to four identical or different hetero atoms, such as nitrogen, oxygen or sulfur atoms, preferably one, two, three or four nitrogen atoms, an oxygen atom or a sulfur atom. Appropriate 5-membered heteroaryl radicals are, for example, monoaza-, diaza-, triaza-, tetraaza-, monooxa- or monothia-cyclic aryl radicals, such as pyrrolyl, pyrazolyl, imidazolyl, triazolyl, tetrazolyl, furyl and thienyl, while suitable appropriate 6-membered radicals are in particular pyridyl and pyrimidyl. Appropriate aromatic radicals are radicals which may be monosubstituted or polysubstituted, for example di- or trisubstituted, for example by identical or different radicals.

Pyrrolyl is, for example, 2- or 3-pyrrolyl. Pyrazolyl is 3- or 4-pyrazolyl. Imidazolyl is 2- or 4-imidazolyl. Triazolyl is, for example, 1,3,5-1H-triazol-2-yl or 1,3,4-triazol-2-yl. Tetrazolyl is, for example, 1,2,3,4-tetrazol-5-yl. Furyl is 2- or 3-furyl and thienyl is 2- or 3-thienyl, while suitable pyridyl is 2-, 3- or 4-pyridyl.

Preferred is 1,2,3,4-tetrazol-5-yl or 1,3,4-triazol-2-yl.

A benzofused heterocyclic ring having 1 or 2 hetero atoms selected from the group consisting of N, S and O, and the heterocyclic ring being saturated or having 1 or 2 double bonds is, for example, indole, quinoline, indoline or tetrahydroisoquinoline.

A 5- to 6-membered heterocyclic ring having 1, 2 or 3 hetero atoms selected from the group consisting of N, S and O is in particular a substituted tetrazole, substituted triazole, such as methyltriazole, a substituted pyrimidine or a substituted pyrazole, such as methylpyrazole. Further ones comprise substituted pyridine, substituted-triazine, imidazole, oxazole, thiazole. A preferred substituent is alkyl, such as methyl.

A 5-14 membered monocyclic- or bicyclic- or fused polycyclic-ring system, having 1 to 8 heteroatoms selected from N, O or S, is also partially or fully saturated.

Preferred is a partially or fully saturated heteroaryl 5- to 6-membered heterocyclic ring having 1, 2, 3 or 4 hetero atoms selected from the group consisting of N, S and O is, for example, a pyrroline radical, pyrrolidine radical, a dihydro- or a tetrahydro-thienyl radical, a dihydro- or a tetrahydro-furan radical, a dihydro- or tetrahydro-pyridine radical, an imidazoline or imidazolidine radical, a pyrazoline or pyrazolidine radical, a thiazoline or thiazolidine radical, an oxazoline or oxazolidine radical, a dihydro- or tetrahydro-pyridine or piperidine radical, or a dihydro- or tetrahydro-pyrane radical. Preferred 5- to 6-membered N-heterocyclic radicals are, for example, bonded via the N-atom, especially a pyrrolidin-1-yl radical.

A heterocyclic radical is unsubstituted or substituted by one or more, for example two or three, substituents. Preferred are corresponding C-substituted radicals.

Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Cycloalkenyl is, for example, $C_3$-$C_7$-cycloalkenyl and is, for example, cyclopropenyl, cyclobutenyl, cyclopentenyl, cyclohexenyl and cycloheptenyl. Cyclopentenyl and cyclohexenyl are preferred.

Halo or halogen is preferably fluoro, chloro, bromo or iodo, most preferably fluoro, chloro or bromo.

Halo-alkyl is, for example, halo-$C_1$-$C_7$alkyl and is in particular halo-$C_1$-$C_4$alkyl, such as trifluoromethyl, 1,1,2-trifluoro-2-chloroethyl or chloromethyl. Preferred halo-$C_1$-$C_7$alkyl is trifluoromethyl.

Aralkyl is for example, carboxylic aryl-alkyl, preferably, phenyl-$C_1$-$C_4$-alkyl, such as benzyl or 2-phenethyl.

Alkoxy is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$alkoxy is preferred.

Alkanoyl is, for example, $C_2$-$C_7$-alkanoyl and is, for example, acetyl, propionyl, butyryl, isobutyryl or pivaloyl. $C_2$-$C_5$-Alkanoyl is preferred, especially acetyl.

Substituted alkylene is substituted $C_2$-$C_7$-alkylene or substituted $C_2$-$C_7$-alkylene which is further interrupted by O, N or S. Said alkylene can be substituted, for example, by $C_1$-$C_7$-alkyl, by $C_1$-$C_7$-alkoxy-$C_1$-$C_7$-alkyl, by carboxy, by $C_1$-$C_7$-alkoxy-carbonyl, by $C_3$-$C_7$-cycloalkyl or by $C_3$-$C_7$-cycloalkyl which is either annealed or attached to said alkylene in spiro form.

Alkoxyalkyl may be linear or branched. The alkoxy group preferably comprises 1 to 4 and especially 1 or 2 C atoms, and the alkyl group preferably comprises 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxypropyl, 4-ethoxybutyl, 5-ethoxypentyl, 6-ethoxyhexyl, propyloxymethyl, butyloxymethyl, 2-propyloxyethyl and 2-butyloxyethyl.

PREFERRED EMBODIMENTS ACCORDING TO THE INVENTION

The groups of preferred embodiments of the invention mentioned below are not to be regarded as exclusive, rather, e.g., in order to replace general expressions or symbols with more specific definitions, parts of those groups of compounds can be interchanged or exchanged using the definitions given above, or omitted, as appropriate, and each of the more specific definitions, independent of any others, may be introduced independently of or together with one or more other more specific definitions for other more general expressions or symbols.

A preferred ring A is the benzo ring which is unsubstituted or substituted by one or more, such as two or three, substituents. Preferred substituents on the A ring are selected from the group consisting of $C_1$-$C_7$-alkyl, especially methyl, halo, especially fluoro, chloro, bromo or iodo, $C_1$-$C_7$-alkoxy, especially methoxy, N-mono- or N,N-di-($C_1$-$C_7$-alkyl)-amino, N-mono- or N,N-di-($C_1$-$C_7$-alkyl)-aminocarbonyl, carboxy, cyano and heterocyclyl, especially morphilinyl. Most preferred substituents on the A ring are selected from the group consisting of F, Cl, Br, OMe, Me, CN, $CO_2H$, $NMe_2$, C(=O)$NMe_2$ and morphiline.

Another preferred ring A is quinoline ring which is unsubstituted or substituted by one to three substituents selected from the group consisting of $C_1$-$C_7$-alkyl, especially methyl, halo, especially fluoro, chloro, bromo or iodo, $C_1$-$C_7$-alkoxy, especially methoxy, N-mono- or N,N-di-($C_1$-$C_7$-alkyl)-amino, N-mono- or N,N-di-($C_1$-$C_7$-alkyl)-aminocarbonyl, carboxy, cyano and heterocyclyl, especially morphilinyl. Most preferred substituents on the A ring are selected from the group consisting of F, Cl, Br, OMe, Me, CN, $CO_2H$, $NMe_2$, C(=O)$NMe_2$ and morphiline, etc.

Another preferred ring A is the pyrrole ring which is unsubstituted or substituted by one or more, such as two or three, substituents. A preferred substituents on the A ring is $C_1$-$C_7$-alkyl, such as methyl.

Preferred Ar is phenyl substituted by one or two substituents. Preferred substituents are halogen and haloalkyl, such as $C_1$ and $CF_3$.

Particularly preferred examples for $R_1$, are:
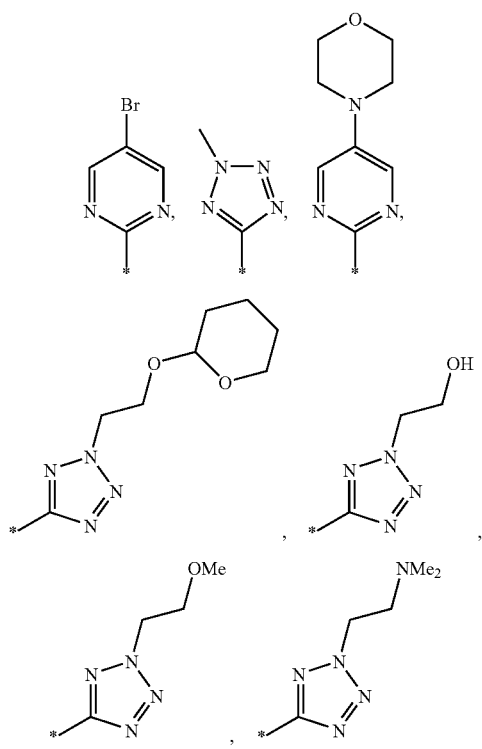
More preferably $R_1$ is 2-$C_1$-$C_7$-alkyl-2H-tetrazol-5-yl.
Particularly preferred examples for $R_2$ are:
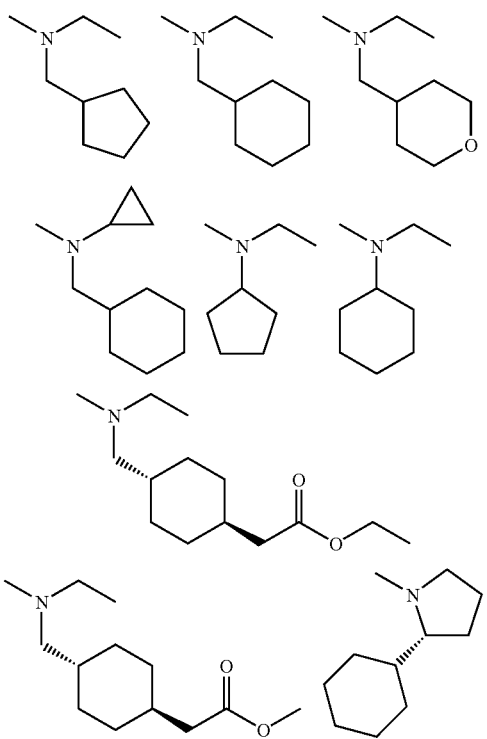
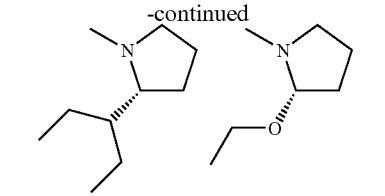
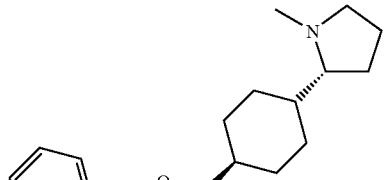
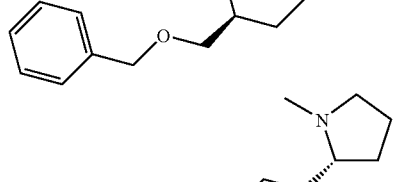
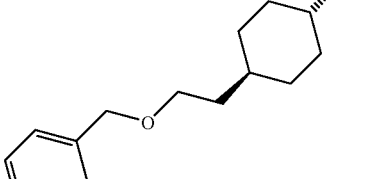
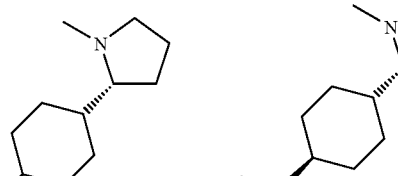
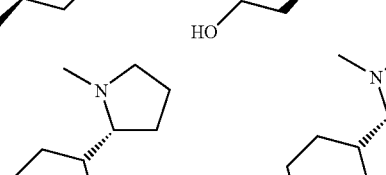
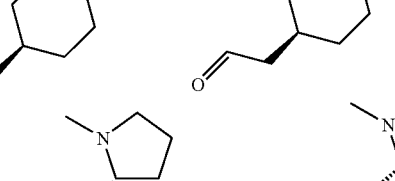
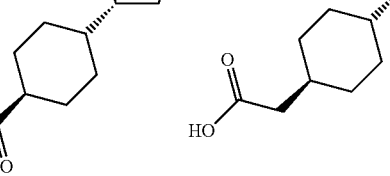
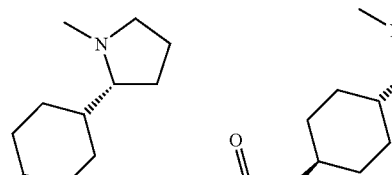
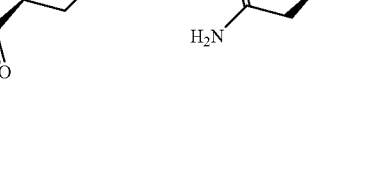

Preferred X is N.
Preferred Y is CH.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Extensive pharmacological investigations have shown that cholesteryl ester transfer protein inhibitors, in particular the compounds I and their pharmaceutically acceptable salts, for example, have pronounced selectivity in inhibiting CETP (cholesteryl ester transfer protein). CETP is involved in the metabolism of any lipoprotein in living organisms, and has a major role in the reverse cholesterol transfer system. Namely, CETP has drawn attention as a mechanism for preventing accumulation of cholesterol in peripheral cells and preventing arteriosclerosis. In fact, with regard to HDL having an important role in this reverse cholesterol transfer system, a number of epidemiological researches have shown that a decrease in CE (cholesteryl ester) of HDL in blood is one of the risk factors of coronary artery diseases. It has been also clarified that the CETP activity varies depending on the animal species, wherein arteriosclerosis due to cholesterol-loading is hardly induced in animals with lower activity, and in reverse, easily induced in animals with higher activity, and that hyper-HDL-emia and hypo-LDL (low density lipoprotein)-emia are induced in the case of CETP deficiency, thus rendering the development of arteriosclerosis difficult, which in turn led to the recognition of the significance of blood HDL, as well as significance of CETP that mediates transfer of CE in HDL into blood LDL. While many attempts have been made in recent years to develop a drug that inhibits such activity of CETP, a compound having a satisfactory activity has not been developed yet.

The CETP inhibitory effect of the compounds of the present invention can be demonstrated by using test models know by a person skilled in the pertinent art, for example, following test models:

(1) Preparation of Human Pro-Apolipoprotein Al (pro-apoAl)

The cDNA of human pro-apoAl (NCBI accession number: NM_000039) is cloned from human liver Quick-Clone™ cDNA (Clontech, Calif.) and inserted to a pET28a vector (Novagen, Germany) for bacterial expression. Expressed protein as a fusion protein with 6×His-tag at N-terminus in BL-21 Gold (DE3) (Strategene, Calif.) is purified using HiTrap Chelating (GE Healthcare, Conn.).

(2) Preparation of Donor Microemulsion

Pro-apoAl containing microemulsion as a donor particle is prepared following previous reports (J. Biol. Chem., 280: 14918-22). Glyceryl trioleate (62.5 ng, Sigma, Mo.), 3-sn-phosphatidylcholine (583 ng, Wako Pure Chemical Industries, Japan), and cholesteryl BODIPY® FL $C_{12}$ (250 ng, Invitrogen, Calif.) are dissolved in 1 mL of chloroform. The solution is evaporated, then residual solvent is removed in vacuum for more than 1 hr. The dried lipid mixture is dissolved in 500 μL of the assay buffer (50 mM Tris-HCl (pH 7.4) containing 150 mM NaCl and 2 mM EDTA) and sonicated at 50° C. with a microtip (MICROSON™ ULTRASONIC CELL DISRUPTOR, Misonix, Farmingdale, N.Y.) at output power 006 for 2 min. After sonication, the solution is cooled to 40° C., added to 100 μg of human pro-apoAl, and sonicated at output power 004 for 5 min at 40° C. The solution, BODIPY-CE microemulsion as a donor molecule is stored at 4° C. after filtration through a 0.45 μm PVDF filter.

(3) In Vitro CETP Activity Assay in Human Plasma

Human EDTA plasma samples from healthy men are purchased from New Drug Development Research Center, Inc. Donor solution is prepared by a dilution of donor microemulsion with assay buffer. Human plasma (50 μL), assay buffer (35 μL) and test compound dissolved in dimethylsulfoxide (1 μL) are added to each well of 96 well half area black flat bottom plate. The reaction is started by the addition of donor solution (14 μL) into each well. Fluorescence intensities are measured every 30 min at 37° C. with excitation wave length of 485 nm and emission wavelength of 535 nm. The CETP activity (Fl/min) is defined as the changes of fluorescence intensity from 30 to 90 min. The $IC_{50}$ value is obtained by the logistic equation (Y=Bottom+(Top-Bottom)/(1+(x/$IC_{50}$)^Hill slope) using Origin software, version 7.5 SR3. The compounds of formula I exhibit inhibitory activity with an $IC_{50}$ value in the range from approximately from 0.001 to 100 μM, especially from 0.01 to 10 μM.

(4) Effects on Plasma HDL Levels in Hamster:

Effects of compounds on HDL-cholesterol level in hamsters are investigated by the method reported previously with some modifications (Eur, J. Phamacol, 466 (2003) 147-154). In brief, male Syrian hamsters (SLC, Shizuoka, Japan) are fed a high cholesterol diet for two weeks. Then, the animals are dosed singly with the compound suspended with carboxyl methyl cellulose solution. HDL-cholesterol levels are measured by using commercially available kit (Wako Pure Chemical, Japan) after the precipitation of apolipoprotein B (apoB)-containing lipoproteins with 13% polyethylene glycol 6000. The compounds elevate greater than 5% of the HDL-cholesterol level compared with control.

The compounds of the present invention or a pharmaceutically acceptable salt thereof have superior CETP inhibitory activity in mammals (e.g., human, monkey, bovine, horse, dog, cat, rabbit, and the like), and can be used as CETP activity inhibitors. In addition, utilizing the superior CETP inhibitory activity of a compound of the present invention or a pharmaceutically acceptable salt thereof, the compounds of the present invention are useful as pharmaceutical agents effective for the prophylaxis or treatment of or delay progression to overt to diseases in which CETP is involved (e.g., hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.), particularly as prophylactic or therapeutic agents for hyperlipidemia or arteriosclerotic diseases and also for the treatment of infection (or egg embryonation) of schistosoma.

A further aspect of the present invention is the use of a CETP inhibitor for the prophylaxis or treatment of or delay progression to overt to a disease selected from the group consisting of coronary heart disease, coronary artery disease, coronary vascular disease, myocardial infarction, stroke, peripheral vascular disease, diabetes such as type II diabetes mellitus, congestive heart failure, and reperfusion injury.

The present invention preferably relates to a compound of formula (I A) or (I B)

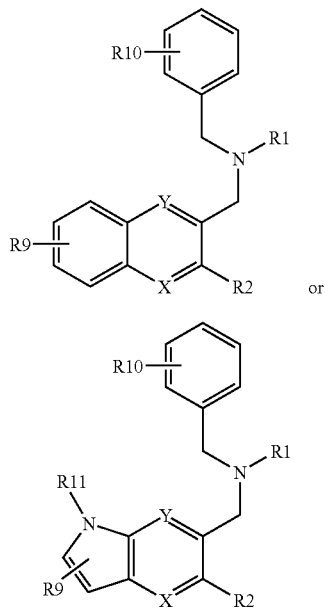

wherein X is N and Y is CH or N;
$R_1$ is heterocyclic ring selected from the group consisting of

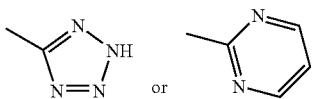

being in each case unsubstituted or N or C-substituted by a substituent selected from the group consisting of, $C_1$-$C_7$-alkyl, $C_3$-$C_7$-cycloalkyl-$C_1$-$C_7$-alkyl, $C_1$-$C_7$-alkoxy, hydroxyl-$C_1$-$C_7$-alkyl-, $C_1$-$C_7$-alkoxy-$C_1$-$C_7$-alkyl-, $(R_4)(R_5)N$—$C_1$-$C_7$-alkyl-, —$N(R_4)(R_5)$ and phenyl-$C_1$-$C_7$-alkyl-;

$R_2$ is selected from the group consisting of —C(=O)$R_3$, —C(=O)—O—$R_3$, —$N(R_4)(R_5)$, —$S(O)_m$—$N(R_4)(R_5)$ and —$NR_3$—$S(O)_m$—$N(R_4)(R_5)$, m being in each case the integer 0, 1 or 2; or $R_2$ is Z;

Z is selected from the group consisting of (i) unsubstituted or substituted $C_3$-$C_7$-cycloalkyl or unsubstituted or substituted $C_3$-$C_7$-cycloalkenyl, and (ii) unsubstituted or substituted carbocyclic phenyl, naphthyl or biphenylyl radical or unsubstituted or substituted pyrrolyl, pyrazolyl, imidazolyl, triazolyl, tetrazolyl, furyl, thienyl, pyridyl, pyrimidyl, pyrrolinyl, pyrrolidinyl, piperidinyl, piperazinyl, morpholinyl, homopiperidinyl, homopiperazinyl, dihydro- or a tetrahydro-thienyl, dihydro- or a tetrahydro-furanyl, dihydro- or tetrahydro-pyridinyl, imidazolinyl or imidazolidinyl, pyrazolinyl or pyrazolidinyl, thiazolinyl or thiazolidinyl, oxazolinyl or oxazolidinyl, dihydro- or tetrahydro-pyridinyl or piperidinyl, or dihydro- or tetrahydro-pyranyl;

$R_3$, independently, represents hydrogen, $C_1$-$C_7$-alkyl, halo-$C_1$-$C_7$-alkyl, unsubstituted or substituted $C_3$-$C_7$-cycloalkyl, unsubstituted or substituted $C_3$-$C_7$-cycloalkenyl, in the cycloalkyl moiety unsubstituted or substituted $C_3$-$C_7$-cycloalkyl-$C_1$-$C_7$-alkyl, in the cycloalkyl moiety unsubstituted or substituted $C_3$-$C_7$-cycloalkyl-$C_2$-$C_7$-alkenyl, unsubstituted or substituted phenyl or naphthyl, unsubstituted or substituted heterocyclic aromatic radical or in the aryl moiety unsubstituted or substituted phenyl-$C_1$-$C_7$-alkyl;

$R_4$ and $R_5$, independently of one another, represents $C_1$-$C_7$-alkyl, $C_3$-$C_7$-cycloalkyl, said $C_1$-$C_7$-alkyl is substituted by one or two substituents selected from the group consisting of unsubstituted or substituted cycloalkyl, unsubstituted or substituted cycloalkenyl, and unsubstituted or substituted heterocyclic radical;

wherein substituted cycloalkyl or substituted cycloalkenyl or substituted alkylene, each of which is substituted by one or two substituents selected from the group consisting of alkyl, alkoxy, —C(=O)—O—$R_3$, —C(=O)—N(alkyl)(alkyl), —N(alkyl)(alkyl), $H_2N$—C(=O)—, $H_2N$—C(=O)-alkyl—, formyl, formyl-alkyl—, cycloalkyl-alkyl, carbocyclic aromatic radical, heterocyclic radical, aralkyl, and heterocyclyl-alkyl; or $R_9$ and $R_{10}$, independently of one another, is hydrogen, halogen, $NO_2$, CN, OH, $C_1$-$C_7$-alkyl, phenyl-$C_1$-$C_7$-alkyl, naphthyl-$C_1$-$C_7$-alkyl, pyridyl-$C_1$-$C_7$-alkyl, $C_3$-$C_7$-cycloalkyl-$C_1$-$C_7$-alkyl, $C_1$-$C_7$-alkoxy-$C_1$-$C_7$-alkyl, phenyl-$C_1$-$C_7$-alkoxy, naphthyl-$C_1$-$C_7$-alkoxy, pyridyl-$C_1$-$C_7$-alkoxy, $C_3$-$C_7$-cycloalkyl-$C_1$-$C_7$-alkoxy, halo-$C_1$-$C_7$-alkyl, $C_1$-$C_7$-alkoxy, $C_1$-$C_7$-alkoxy-$C_1$-$C_7$-alkoxy, carboxy, $C_1$-$C_7$-alkoxy-carbonyl, $C_1$-$C_7$-alkyl-$S(O)_m$—, phenyl-$C_1$-$C_7$-alkyl-$S(O)_m$, naphthyl-$C_1$-$C_7$-alkyl-$S(O)_m$, pyridyl-$C_1$-$C_7$-alkyl-$S(O)_m$, halo-$C_1$-$C_7$-alkoxy, and $C_2$-$C_7$-alkanoyl(oxy); m being in each case the integer 0, 1 or 2, $C_3$-$C_7$-cycloalkyl, $C_3$-$C_7$-cycloalkenyl; in the phenyl moiety unsubstituted or substituted phenyl-$C_1$-$C_7$-alkyl and in the pyridyl moiety unsubstituted or substituted pyridyl-$C_1$-$C_7$-alkyl; and wherein a corresponding cycloalkyl radical, cycloalkenyl radical, carbocyclic aromatic radical, heterocyclic radical or heterocyclic aromatic radical is optionally substituted by one or more substitutents selected from halogen, hydroxyl, cyano, alkyl or alkoxy;

wherein p is 0, or 1 or 2 or 3;

wherein n is 0, or 1 or 2 or 3;

$R_{11}$, is $C_1$-$C_7$-alkyl;

Substituent attached in Z is independently of one another, hydrogen or one or more substituents selected from the group consisting of halogen, OH, $NH_2$, carbonyl (=O), $C_1$-$C_7$-alkyl, $C_3$-$C_7$-cycloalkyl, $C_3$-$C_7$-cycloalkyl-$C_1$-$C_7$-alkyl-, $C_1$-$C_7$-alkoxy-$C_1$-$C_7$-alkyl-, $C_3$-$C_7$-cycloalkyloxy-$C_1$-$C_7$-alkyl-, phenyl-$C_1$-$C_7$-alkoxy-, $C_3$-$C_7$-cycloalkyl-$C_1$-$C_7$-alkoxy-, halo-$C_1$-$C_7$-alkyl-, $C_1$-$C_7$-alkoxy-, $C_1$-$C_7$-alkoxy-$C_1$-$C_7$-alkoxy-, carboxy-, $C_1$-$C_7$-alkoxy-carbonyl-, $C_1$-$C_7$-alkyl-$S(O)_m$—, phenyl-$C_1$-$C_7$-alkyl-$S(O)_m$—, halo-$C_1$-$C_7$-alkoxy-, and $C_2$-$C_7$-alkanoyl-, $C_1$-$C_7$-alkoxy-$C_3$-$C_7$-cycloalkyl-, phenyl-$C_1$-$C_7$-alkoxy-$C_3$-$C_7$-cycloalkyl-, hydroxy-$C_3$-$C_7$-cycloalkyl-, hydroxy-$C_1$-$C_7$-alkyl-$C_3$-$C_7$-cycloalkyl-, formyl-$C_3$-$C_7$-cycloalkyl-, formyl-$C_1$-$C_7$-alkyl-$C_3$-$C_7$-cycloalkyl-, carboxy-$C_3$-$C_7$-cycloalkyl-, carboxy-$C_1$-$C_7$-alkyl-$C_3$-$C_7$-cycloalkyl-, $H_2NC(=O)$—$C_3$-$C_7$-cycloalkyl-, $H_2NC(=O)$—$C_1$-$C_7$-alkyl-$C_3$-$C_7$-cycloalkyl-; or a salt thereof.

The present invention more preferably relates to a compound of formula (I C)

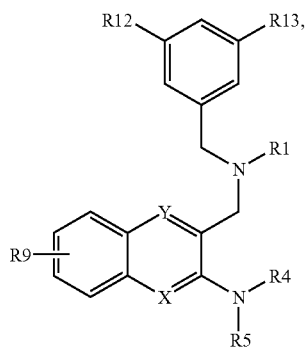

wherein X is N and Y is CH or N;
R$_1$ is 2-C$_1$-C$_7$-alkyl-2H-tetrazol-5-yl;
the element —N(R$_4$)(R$_5$) is pyrrolidine-1-yl which is substituted by one or two stubstituents selected from the group consisting of C$_1$-C$_7$-alkyl-, C$_3$-C$_7$-cycloalkyl-, C$_3$-C$_7$-cycloalkyl-methyl-C$_1$-C$_7$-alkoxy-methyl-, hydroxy-C$_1$-C$_2$-alkyl-C$_3$-C$_7$-cycloalkyl-, formyl-C$_3$-C$_7$-cycloalkyl-, formyl-C$_1$-C$_2$-alkyl-C$_3$-C$_7$-cycloalkyl-, HO$_2$C—C$_3$-C$_7$-cycloalkyl-, HO$_2$C—C$_1$-C$_2$-alkyl-C$_3$-C$_7$-cycloalkyl-, H$_2$NC(=O)—C$_3$-C$_7$-cycloalkyl-, or H$_2$NC(=O)—C$_1$-C$_2$-alkyl-C$_3$-C$_7$cycloalkyl-;
R$_9$ is one or two substituents selected from hydrogen, —CN, C$_1$-C$_7$-alkyl-, C$_1$-C$_7$-alkoxy, (C$_1$-C$_7$-alkyl)(C$_1$-C$_7$-alkyl-)amine-, halo-C$_1$-C$_7$-alkyl, or halogen;
R$_{12}$ and R$_{13}$, independently of one another, is halo-C$_1$-C$_7$-alkyl or also halogen;
wherein p is 0, or 1 or 2; or
R$_4$ is (C$_1$-C$_4$)alkyl- or (C$_3$-C$_5$)cycloalkyl-; and
R$_5$ is (C$_3$-C$_7$)cycloalkyl-(C$_1$-C$_2$)alkyl- which is optionally substituted by one to two substitutents selected from hydroxyl, alkoxy, HO$_2$C—, HO$_2$C—(C$_1$-C$_3$)alkyl-, hydroxy-(C$_1$-C$_3$) alkyl-, (C$_1$-C$_6$)alkoxy-carbonyl-, or (C$_1$-C$_6$)alkoxycarbonyl-(C$_1$-C$_3$)alkyl-;
or a salt thereof.

In one embodiment, the present invention relates to the compound of formula (II):

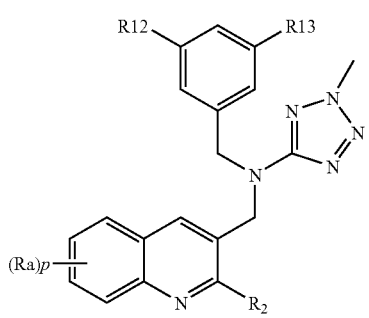

wherein p is 0, or 1 or 2;
Ra is halogen, or (C$_1$-C$_4$)-alkoxy, or halo-(C$_1$-C$_4$)alkyl;
R$_{12}$ and R$_{13}$ are independently halogen or halo-(C$_1$-C$_4$)alkyl;
R$_2$ is formula (III):

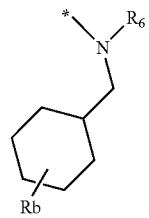

wherein R$_6$ is (C$_1$-C$_4$)alkyl- or (C$_3$-C$_5$)cycloalkyl-; Rb is —(CH$_2$)$_n$—Rc; n is 0, or 1, or 2, or 3, Rc is carboxy, hydroxy, (C$_1$-C$_4$)-alkoxy, or (C$_1$-C$_4$)-alkoxycarbonyl; or a salt thereof. Preferably, n is 0, Rc is hydroxy or (C$_1$-C$_4$)-alkoxy. Also preferably, n is 1 or 2 or 3, Rc is carboxy, hydroxy, (C$_1$-C$_4$)-alkoxy, or (C$_1$-C$_4$)-alkoxycarbonyl.

In another embodiment, the present invention relates to the compound of formula (II):

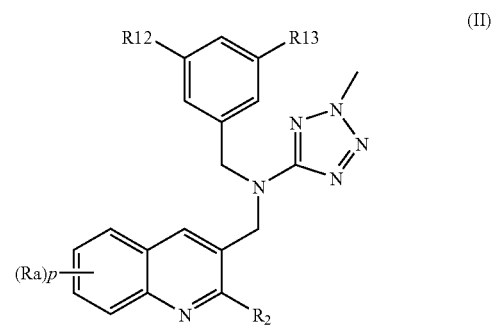

wherein p is 0, or 1 or 2;
Ra is halogen, or (C$_1$-C$_4$)-alkoxy, or halo-(C$_1$-C$_4$)alkyl;
R$_{12}$ and R$_{13}$ are independently halogen or halo-(C$_1$-C$_4$)alkyl;
R$_2$ is formula (IIIA):

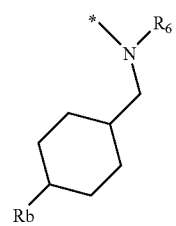

wherein R$_6$ is (C$_1$-C$_4$)alkyl- or (C$_3$-C$_5$)cycloalkyl-; Rb is —(CH$_2$)$_n$—Rc; n is 0, or 1, or 2, or 3, Rc is carboxy, hydroxy, (C$_1$-C$_4$)-alkoxy, or (C$_1$-C$_4$)-alkoxycarbonyl; or a salt thereof. Preferably, n is 0, Rc is hydroxy or (C$_1$-C$_4$)-alkoxy. Also preferably, n is 1 or 2 or 3, Rc is carboxy, hydroxy, (C$_1$-C$_4$)-alkoxy, or (C$_1$-C$_4$)-alkoxycarbonyl.

In another embodiment, the present invention relates to the compound of formula (II):

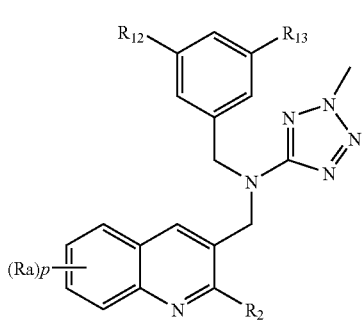
(II)

wherein p is 0, or 1, or 2, or 3;
Ra is halogen, or $(C_1-C_4)$-alkoxy, or halo-$(C_1-C_4)$alkyl;
$R_{12}$ and $R_{13}$ are independently halogen or halo-$(C_1-C_4)$alkyl;
$R_2$ is formula (IV):

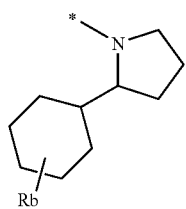
(IV)

wherein Rb is —$(CH_2)_n$—Rc; n is 0, or 1, or 2, or 3; Rc is carboxyl, hydroxy, formyl, $(C_1-C_4)$-alkoxy, $H_2NC(=O)$—, $(C_1-C_4)$-alkoxycarbonyl, or halo-$(C_1-C_4)$-alkoxycarbonyl; or a salt thereof.

In another embodiment, the present invention relates to the compound of formula (II), wherein $R_2$ is formula (IVA):

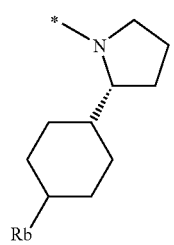
(IVA)

wherein Rb is —$(CH_2)_n$—Rc; n is 0, or 1, or 2, or 3; Rc is carboxyl, hydroxy, formyl, $(C_1-C_4)$-alkoxy, $H_2NC(=O)$—, $(C_1-C_4)$-alkoxycarbonyl, or halo-$(C_1-C_4)$-alkoxycarbonyl; or a salt thereof.

In another embodiment, the present invention relates to the compound of formula (II), wherein $R_2$ is formula (IVA), p is 1 or 2; Ra is halogen; $R_{12}$ and $R_{13}$ are halo-$(C_1-C_4)$alkyl; Rb is —$(CH_2)_n$—Rc, wherein n is 0 or 1; Rc is carboxyl, or $(C_1-C_4)$-alkoxycarbonyl, or halo-$(C_1-C_4)$-alkoxycarbonyl; or a pharmaceutically acceptable salt.

In another embodiment, the present invention relates to the compound of formula (II),

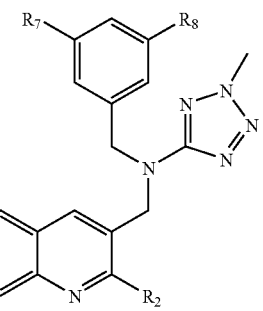
(II)

wherein p is 0, or 1 or 2;
Ra is halogen, or $(C_1-C_4)$-alkoxy, or halo-$(C_1-C_4)$alkyl;
$R_7$ and $R_8$ are independently halogen or halo-$(C_1-C_4)$alkyl;
$R_2$ is selected from formula (III) or (IV):

(III)

(IV)

wherein Rb is —$(CH_2)_n$—C(O)—O-Rc; n is 1, or 2, or 3, Rc is hydrogen, $H_2N$—, $(C_1-C_4)$-alkyl, or halo-$(C_1-C_4)$alkyl.

In another embodiment, the present invention relates to the compound of formula (II),

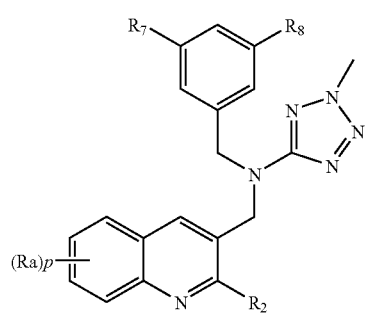
(II)

wherein p is 0, or 1 or 2;
Ra is halogen, or $(C_1-C_4)$-alkoxy, or halo-$(C_1-C_4)$alkyl;
$R_7$ and $R_8$ are independently halogen or halo-$(C_1-C_4)$alkyl;

$R_2$ is selected from formula (III) or (IV):

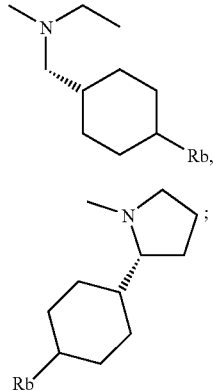

wherein Rb is —$(CH_2)_n$—C(O)—O-Rc; n is 0, or 1, or 2, or 3, Rc is hydrogen, $H_2N$—, ($C_1$-$C_4$)-alkyl, or halo-($C_1$-$C_4$) alkyl.

Yet in another embodiment, the invention relates in particular to the novel compounds shown in the examples and to the modes of preparation described therein.

Abbreviation:

Ac: acetyl, AcOEt: ethyl acetate, AIBN: 2,2'-azobisisobutyronitrile, BOP: benzotriazol-1-yloxytris(dimethylamino) phosphonium hexafluorophosphate, BPO: benzoyl peroxide, n-BuLi: n-butyl lithium, DCC: N,N'-dicyclohexyl carbodiimide, DHP: 3,4-dihydro-2H-pyran, DIPEA: N,N-diisopropylethylamine, DMAP: 4-N,N-dimethylaminopyridine, mCPBA: m-chloro perbenzoic acid, EtOH: ethanol, EDC: N-ethyl-N'-(3-dimethylaminopropyl)carbodiimide, HATU: Hex: n-hexane, KOt-Bu: potassium tert-butoxide, $LiAlH_4$: lithium alminum hydride, MeOH: methanol, Ms: methansulfonyl, $NaBH_4$: sodium tetraborohydride, NBS: N-bromosuccinimide, $POCl_3$: phosphorus(III) oxychloride, sat.: saturated, TEA: triethylamine, THF: tetrahydrofuran, Ms: methansulfonyl, DMF: N,N-dimethylformamide, TFA: trifluoroacetic acid, HPLC: ultra performance liquid chromatography.

The invention relates to processes for the preparation of the compounds according to the invention. The preparation of compounds of formula (I) or salts thereof comprises, for example, the following general schemes:

Scheme 1

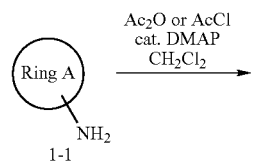

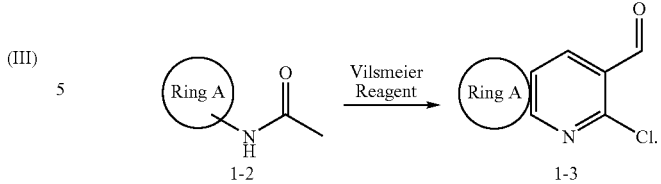

Intermediates 1-1, 1-2 and 1-3 utilized in the present invention can be purchased or prepared as shown in Scheme 1. Appropriately substituted aryl amines 1-1, wherein ring A is as defined herein or in the claims, can be treated with acetic anhydride ($Ac_2O$) or acetyl chloride (AcCl) and a catalytic amount of 4-N,N-dimethylaminopyridine (DMAP) in $CH_2Cl_2$ to afford the corresponding intermediates 1-2. Vilsmeier-type cyclization of intermediates 1-2 by treatment with phosphoryl chloride ($POCl_3$) in DMF can give the corresponding intermediates 1-3 [see for example: Meth-Cohn et al., *J. Chem. Soc., Perkin Trans.* 1 1520 (1981)].

Scheme 2.

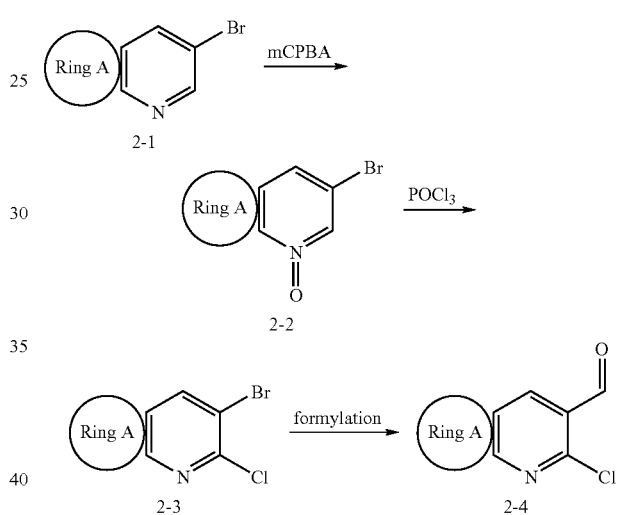

Intermediates 2-1, 2-2, 2-3 and 2-4 utilized in the present invention can be purchased or prepared as shown in Scheme 2. An appropriately substituted aryl bromides 2-1, wherein ring A is as defined herein or in the claims, can be treated with an oxidative reagent such as m-chloroperbenzoic acid (m-CPBA) or the like in an appropriate solvent such as $CH_2Cl_2$ or the like to afford the corresponding intermediates 2-2. Chlorination of intermediates 2-2 by treatment with phosphoryl chloride ($POCl_3$) can afford the corresponding intermediates 2-3 [see for example: Grig-Alexa et al., *Synlett* 11, 2000 (2004)]. Formylation of intermediates 2-3 can be accomplished with n-BuLi and DMF to give the corresponding intermediates 2-4. Alternatively, formylation can be accomplished with carbon monoxide and sodium formate or hydrogen in the presence of palladium catalyst [see for example: Okano et al., *Bull. Chem. Soc. Jap.* 67, 2329 (1994)].

Scheme 3.

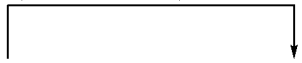

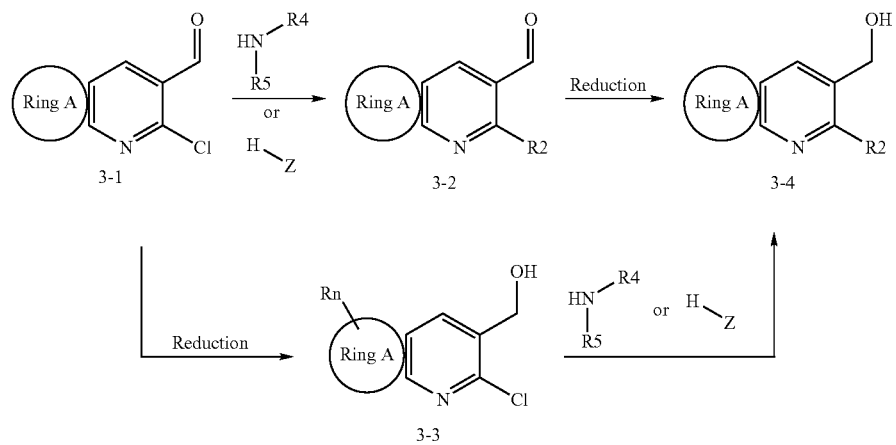

L: leaving group

Intermediates 3-1 of the present invention, wherein ring A is as defined herein or in in the claims, can be purchased or prepared according to the procedure outlined in Schemes 1 and 2. Coupling reaction between appropriately substituted aryl chlorides 3-1 and appropriately substituted amines [($R_4$)($R_5$)NH] or H—Z, wherein ring A, $R_4$, $R_5$, and Z are as defined herein or in the claims, in the presence of an appropriate base such as triethylamine (TEA), potassium carbonate ($K_2CO_3$) or the like in an appropriate solvent such as tetrahydrofuran (THF), toluene, toluene/water can give the corresponding intermediates 3-2, wherein ring A, $R_2$, Z, $R_4$, and $R_5$ are as defined herein or in the claims. Alternatively, intermediates 3-2 can be prepared by treatment of 3-1 with an appropriate amine [$R_4$—$NH_2$ or $R_5$—$NH_2$] followed by alkylation with an appropriate reagent [$R_5$-L or $R_4$-L (L: leaving group such as halogen, —OMs, etc.)]. Reduction of aldehydes 3-2 with a reductive reagent such as sodium borohydride or the like in methanol or ethanol or the like can give the corresponding alcohols 3-4. Alternatively, the chloride 3-1 can be reduced with a reductive reagent such as sodium borohydride or the like, followed by amination with an appropriately substituted amine [(R4)(R5)NH] or H—Z to give the corresponding alcohols 3-4.

Scheme 4.

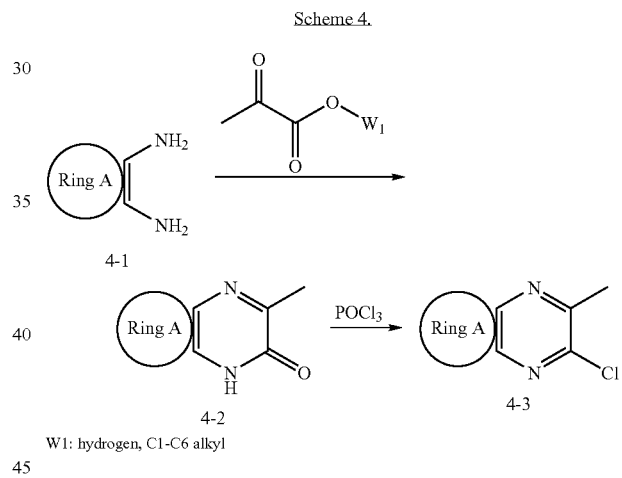

W1: hydrogen, C1-C6 alkyl

Intermediates 4-1, 4-2 and 4-3 utilized in the present invention, wherein ring A is as defined herein or in the claims, can be purchased or prepared as shown in Scheme 4. [see for example: Katou et al., *Heterocycles*, 52, 911 (2000)].

Scheme 5

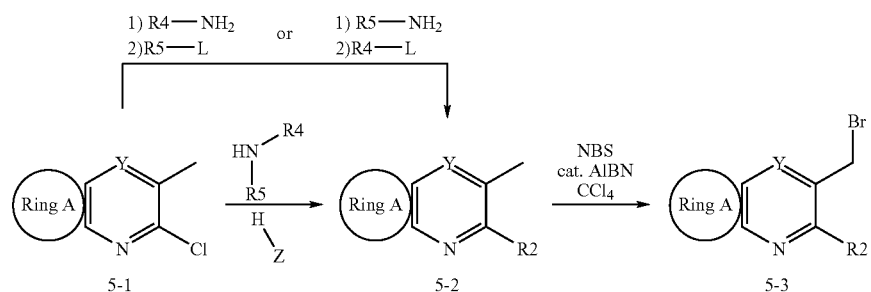

Intermediates 5-1 of the present invention, wherein ring A and Y are as defined herein or in the claims, can be purchased or prepared according to the procedure outlined in Scheme 4. The coupling reaction between appropriately substituted aryl chlorides 5-1 and appropriately substituted amines [($R_4$)($R_5$)NH] or H—Z, wherein ring A, $R_4$, $R_5$ and Z are as defined herein or in the claims, in the presence of appropriate base such as triethylamine (TEA), potassium carbonate ($K_2CO_3$) or the like in an appropriate solvent such as tetrahydrofuran (THF), toluene, toluene/water can give the corresponding intermediates 5-2, wherein ring A, $R_2$ and Y are as defined herein or in the claims. Alternatively, intermediates 5-2 can be prepared by treatment of 5-1 with an appropriate amine [$R_4$—$NH_2$ or $R_5$—$NH_2$], followed by alkylation with an appropriate reagent [$R_5$-L or $R_4$-L (L: leaving group such as halogen, —OMs, etc.)]. Halogenation of intermediates 5-2 with halogenating reagents such as N-bromosuccinimide or the like in the presence of a catalytic amount of 2,2'-azobisisobutyronitrile (AIBN) or benzoyl peroxide (BPO) in $CCl_4$ can give the corresponding benzyl halides 5-3.

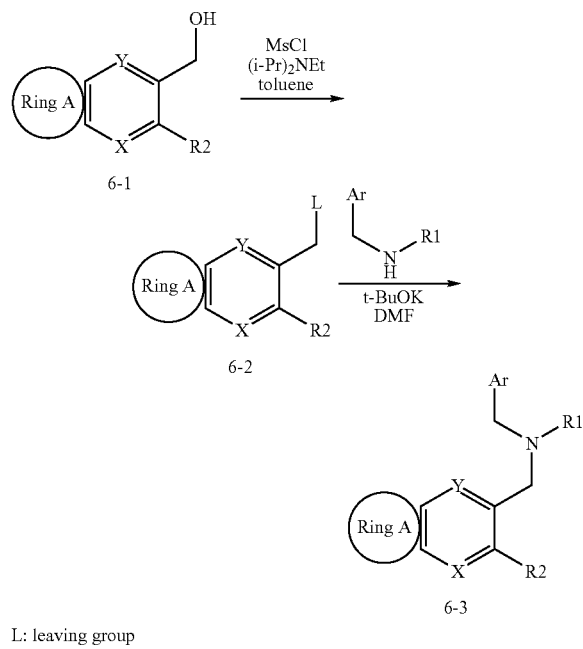

6-1

6-2

6-3

L: leaving group

Compounds 6-3 of the present invention, wherein ring A, Ar, $R_1$, $R_2$, X and Y are as defined herein or in the claims can be prepared according to the procedure outlined in Scheme 6. Intermediates 6-1 and 6-2 (L: leaving group such as halogen, —OMs, etc.) of the present invention, wherein ring A, $R_2$, X and Y are as defined herein or in the claims, can be prepared according to the procedures outlined in Schemes 3 and Scheme 5, respectively. The appropriately substituted alcohol 6-1 can be treated with thionyl chloride or methansulfonyl chloride or the like, with or without a base, such as triethylamineine and N,N-diisopropylethylamine or the like, in a solvent such as THF or toluene to afford the corresponding intermediates 6-2. Alternatively, intermediates 6-2 can be prepared by treatment of 6-1 with carbon tetrabromide and triphenylphosphine in an appropriate solvent such as dichloromethane or the like. The preferred leaving group is bromide or chloride, but may also be iodide, mesylate, tosylate or the like. Intermediates 6-2 can be treated with an appropriate amine [(Ar—$CH_2$—)($R_1$)NH], wherein Ar and $R_1$ are as defined herein or in the claims, and a base such as potassium tert-butoxide or the like in solvents such as DMF or THF or the like to give the corresponding coupling products 6-3.

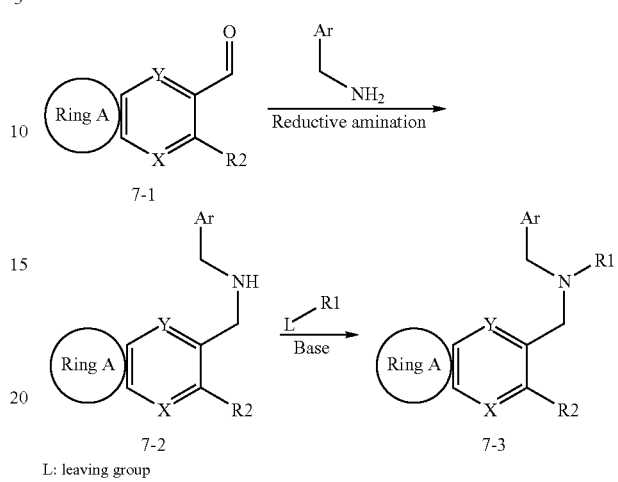

7-1

7-2

7-3

L: leaving group

Compounds 7-3 of the present invention, wherein ring A, Ar, $R_1$, $R_2$, X and Y are as defined herein or in the claims, can be prepared according to the procedure outlined in Scheme 7. Intermediates 7-1 of the present invention, wherein ring A, $R_2$, X and Y are as defined herein or in the claims, can be prepared according to the procedure outlined in Scheme 3. The appropriately substituted aldehyde 7-1 can be treated with substituted aryl-methylamine in the presence of reducing reagent such as sodium borohydride, sodium cyanoborohydride, sodium triacetoxybotohydride or the like and an acid such as acetic acid, trifluoroacertic acid, or the like in methanol, ethanol, $CH_2Cl_2$, 1,2-dichloroehane or the like to afford the corresponding intermediates 7-2. Alternatively, intermediates 7-2 can be prepared by treatment with benzylamine and a catalytic amount of acid such as p-toluene sulfonic acid or the like in toluene to give corresponding imine, followed by reduction of the resulting imine using a reducing reagent such as sodium borohydride. Compounds 7-2 can be converted to compounds 7-3 by treatment with an appropriate R1-L such as acyl chloride, alkoxycarbonylchloride, substituted chloropyridine, substituted chloropyrimidine or the like in an appropriate solvent such as toluene, THF, DMF or the like, in the presence of an appropriate base, such as potassium carbonate, triethylamine, sodium hydride, potassium bis(trimethylsilyl)amide or the like.

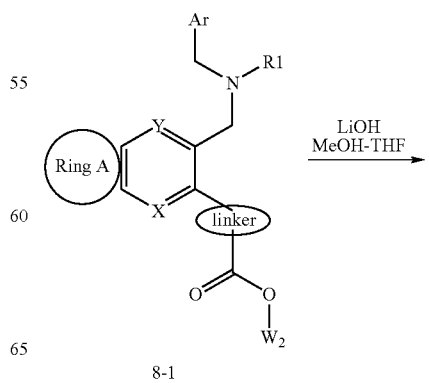

8-1

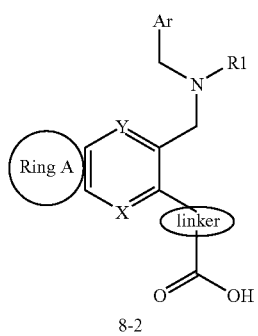

8-2

W2: C1-C6 alkyl

Compounds 8-2 of the present invention, wherein ring A, Ar, $R_1$, X and Y are as defined herein or in the claims, and wherein the -(linker)-$CO_2H$ is described in $R_2$ [ex. —N($C_1$-$C_4$-alkyl)($C_1$-$C_4$-alkyl-$C_3$-$C_7$-cycloalkyl-$C_1$-$C_3$-alkyl-$CO_2H$)] can be prepared according to the procedure outlined in Scheme 8.

Compounds 8-1 of the present invention, wherein ring A, Ar, $R_1$, X and Y are as defined herein or in the claims, and wherein $W_2$ is $C_1$-$C_6$ alkyl can be prepared according to the procedure outlined in Schemes 6 or 7. Intermediates 8-1 can be treated with a base such as lithium hydroxide, sodium hydroxide, potassium hydroxide or the like in an appropriate solvent such as methanol, ethanol, THF or the like to afford the corresponding carboxylic acids 8-2.

Scheme 9.

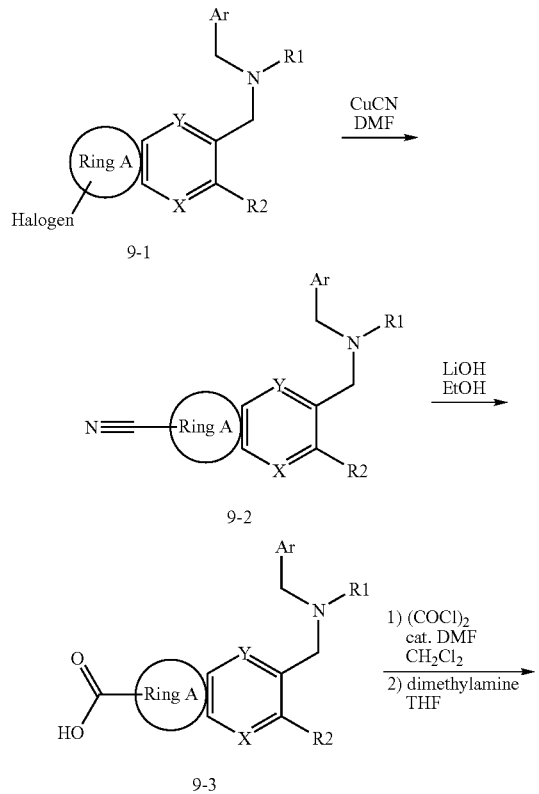

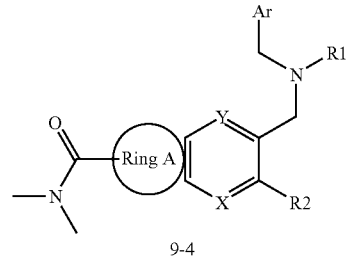

9-4

Compounds 9-2, 9-3, and 9-4 of the present invention, wherein ring A, Ar, $R_1$, $R_2$, X and Y are as defined herein or in the claims, can be prepared according to the procedure outlined in Scheme 9. Compounds 9-1 of the present invention wherein ring A, Ar, $R_1$, $R_2$, X and Y are as defined herein or in the claims and wherein the halogen is preferably iode or bromo, can be prepared according to the procedures outlined in Schemes 6 or 7. Compounds 9-1 can be treated with CuCN in DMF at elevated temperature to afford the corresponding compounds 9-2. Alternatively, the nitrites 9-2 can be prepared by coupling reactioin between compounds 9-1 and KCN in the presence of CuI and a palladium(II) salt or in the presence of certain copper or nickel complexes. Carboxylic acids 9-3 can be prepared by treatment of 9-2 with lithium hydroxide, sodium hydroxide or the like in an appropriate solvent such as methanol, ethanol, THF or the like. Chlorination of carboxylic acids 9-3 can be accomplished with oxalyl chloride and a catalytic amount of DMF in an appropriate solvent such as $CH_2Cl_2$ or with thionylchloride in an appropriate solvent such as toluene. Subsequent amination with an amine such as dimethylamine in THF or the like affords amides 94. Alternatively, amides 9-4 can be prepared by amination with an amine in the presence of a coupling reagent such as DCC, EDC, BOP, HATU or the like in an appropriate solvent such as $CH_2Cl_2$, THF or the like.

Scheme 10.

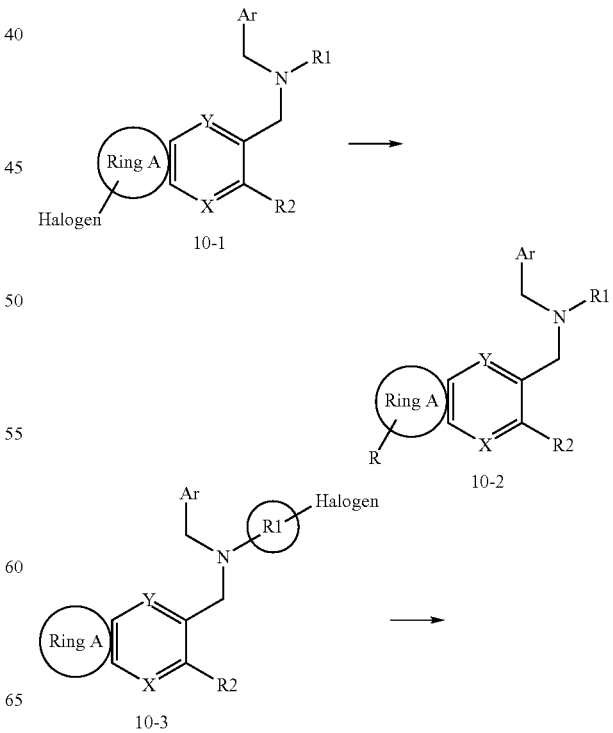

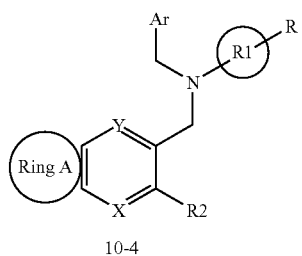

10-4

Compounds 10-2 or 10-4 of the present invention, wherein Ar, $R_1$, $R_2$, X and Y are as defined herein or in the claims and wherein R is alkyl, alkoxy, dialkylamine, or cyclicamine, can be prepared according to the procedure outlined in Scheme 10. Compounds 10-1 or 10-3 of the present invention, wherein Ar, $R_1$, $R_2$, X and Y are as defined herein or in the claims and wherein the halogen is preferably iodo or bromo, can be prepared according to the procedures outlined in Schemes 6 or 7. The coupling reaction between compounds 10-1 or 10-3 and an appropriate alcohol, amine, or alkyl Grignard reagent can be performed in the presence of a base such as NaOt-Bu, KOt-Bu, or the like, palladium or nickel catalyst and a ligand such as 2-(di-t-butylphosphino)biphenyl or the like in an appropriate solvent such as toluene, THF, dioxane, or the like, at elevated temperature to afford the corresponding coupling products 10-2 or 10-4.

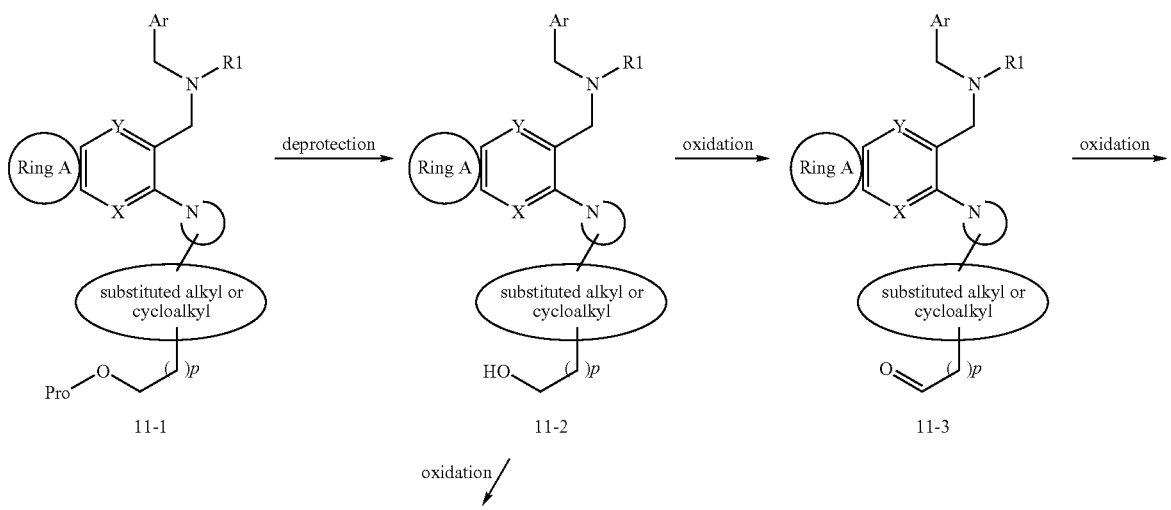

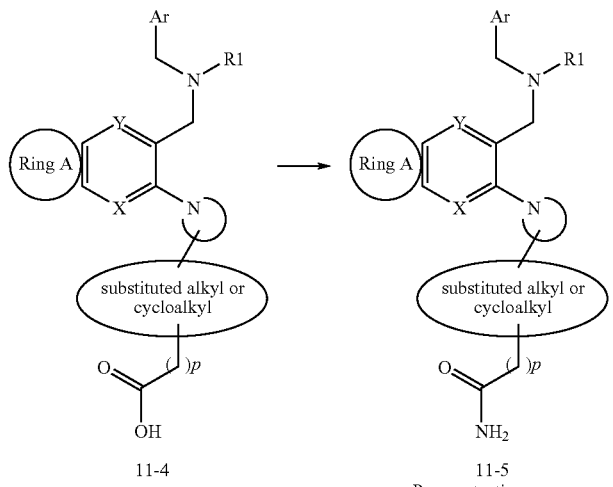

Pro: protecting group

Compounds 11-2, 11-3, 11-4 and 11-5 of the present invention, wherein Ar, $R_1$, $R_4$, $R_5$, X and Y are as defined herein or in the claims, and p is an integer as defined herein or in the claims, can be prepared according to the procedure outlined in Scheme 11. Compounds 11-1 of the present invention wherein Ar, $R_1$, $R_4$, $R_5$, X and Y are as defined herein or in the claims, and p is an integer as defined herein or in the claims, can be prepared according to the procedures outlined in Schemes 6 or 7. Deprotection of compounds 11-1 (Pro: appropriate protecting group for alcohol such as benzyl, tetrahydropyranyl, or the like) according to methods described in Peter G, M Wuts and Theodora W. Greene "Protective Groups in Organic Synthesis". $4^{th}$ Ed., Wiley and references cited therein can afford alcohols 11-2. Compounds 11-2 can be converted to aldehydes 11-3 or carboxylic acids 11-4 by oxidation with an oxidative reagent such as PCC, PDC, $KMnO_4$ or by Swern oxidation, Dess-Martin oxidation, TEMPO oxidation or the like in an appropriate solvent. Aldehydes 11-3 also can be converted to carboxylic acids 11-4 by oxidation with an oxidative reagent such as $KMnO_4$ or via sodium chlorite oxidation (ex. $NaClO_2/NaH_2PO_4$/2-methyl-2-butene), TEMPO oxidation or the like in an appropriate solvent. Treatment of carboxylic acids 11-4 with $NH_4Cl$ in the presence of a coupling reagent such as DCC, EDC, BOP, HATU or the like and a base such as triethylamine or the like in an appropriate solvent such as $CH_2Cl_2$, THF or the like can afford amides 11-5. Alternatively, carboxylic acids 11-4 can be converted to acid chlorides by reaction with thionyl chloride, oxalyl chloride or the like in an appropriate solvent such as toluene, $CH_2Cl_2$, or the like, followed by the reaction with ammonia in an appropriate solvent such as THF, $CH_2Cl_2$, or the like to give amides 11-5.

In view of the close relationship between the novel compound in the free form and in the form of its salts, in the preceding text and below the free compound or its salts may correspondingly and advantageously also be understood as meaning the corresponding salts or the free compound.

Depending on the choice of the starting materials and procedures, the novel compounds can be present in the form of one of the possible isomers or as mixtures thereof, for example as pure optical isomers, such as antipodes, or as isomer mixtures, such as racemates, diastereoisomer mixtures or racemate mixtures, depending on the number of asymmetric carbon atoms.

The invention also relates to those embodiments of the process, according to which a compound obtainable as an intermediate in any step of the process is used as a starting material and the missing steps are carried out or a starting material in the form of a derivative or salt and/or its racemates or antipodes is used or, in particular, formed under the reaction conditions.

In the process of the present invention, those starting materials are preferably used which lead to the compounds described as particularly useful at the beginning. The invention likewise relates to novel starting materials which have been specifically developed for the preparation of the compounds according to the invention, to their use and to processes for their preparation.

The invention likewise relates to a combination of a compound of formula (I), (IA), (IB), (IC) or (II) respectively, or a pharmaceutically acceptable salt thereof with a further active principle.

The combination may be made for example with the following active principles, selected from the group consisting of a:
(i) HMG-Co-A reductase inhibitor or a pharmaceutically acceptable salt thereof,
(ii) angiotensin II receptor antagonist or a pharmaceutically acceptable salt thereof,
(iii) angiotensin converting enzyme (ACE) Inhibitor or a pharmaceutically acceptable salt thereof,
(iv) calcium channel blocker or a pharmaceutically acceptable salt thereof,
(v) aldosterone synthase inhibitor or a pharmaceutically acceptable salt thereof,
(vi) aldosterone antagonist or a pharmaceutically acceptable salt thereof,
(vii) dual angiotensin converting enzyme/neutral endopeptidase (ACE/NEP) inhibitor or a pharmaceutically acceptable salt thereof,
(viii) endothelin antagonist or a pharmaceutically acceptable salt thereof,
(ix) renin inhibitor or a pharmaceutically acceptable salt thereof,
(x) diuretic or a pharmaceutically acceptable salt thereof,
(xi) an ApoA-I mimic, and
(Xii) a DGAT inhibitor.

An angiotensin II receptor antagonist or a pharmaceutically acceptable salt thereof is understood to be an active ingredients which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

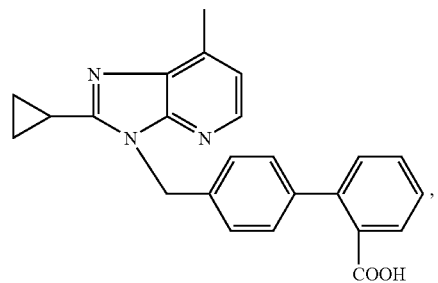

the compound with the designation SC-52458 of the following formula

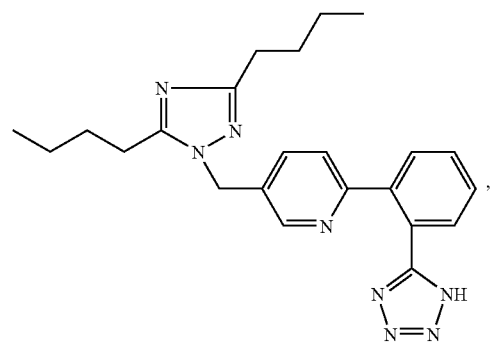

and the compound with the designation ZD-8731 of the following formula

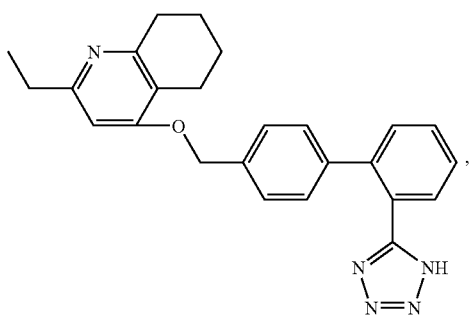

or, in each case, a pharmaceutically acceptable salt thereof.

Preferred AT$_1$-receptor antagonist are those agents which have been marketed, most preferred is valsartan or a pharmaceutically acceptable salt thereof.

HMG-Co-A reductase inhibitors (also called β-hydroxy-β-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

Aldosterone synthase inhibitor is an enzyme that converts corticosterone to aldosterone to by hydroxylating cortocosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

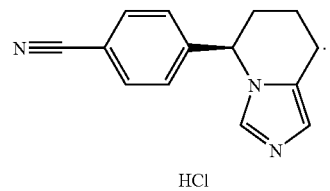

A preferred steroidal aldosterone antagonist is eplerenone of the formula

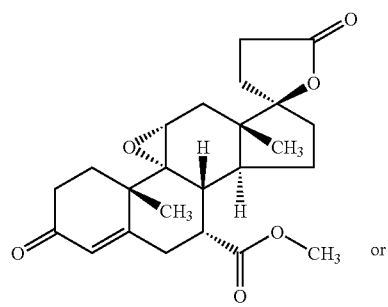

spironolactone.

A preferred dual angiotensin converting enzyme/neutral endopetidase (ACE/NEP) inhibitor is, for example, omapatrilate (cf. EP 629627), fasidotril or fasidotrilate, or, if appropriate, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

A renin inhibitor is, for example, a non-peptidic renin inhibitor such as the compound of formula

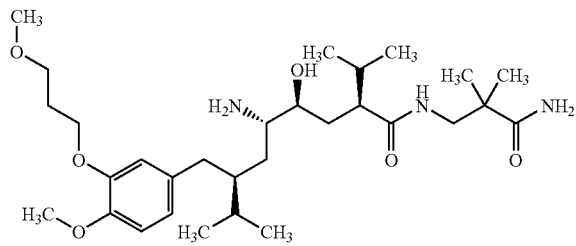

chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide. This representative is specifically disclosed in EP 678503A. Especially preferred is the hemi-fumarate salt thereof.

A diuretic is, for example, a thiazide derivative selected from the group consisting of chlorothiazide, hydrochlorothiazide, methylclothiazide, and chlorothalidon. The most preferred is hydrochlorothiazide.

An ApoA-I mimic is, for example, D4F peptide, especially of formula D-W-F-K-A-F-Y-D-K-V-A-E-K-F-K-E-A-F A DGAT inhibitor is for example, one or more of the compounds described in WO2005072740, and U.S. provisional application No. 60/787,859.

Preferably, the jointly therapeutically effective amounts of the active agents according to the combination of the present invention can be administered simultaneously or sequentially in any order, separately or in a fixed combination.

The structure of the active agents identified by generic or tradenames may be taken from the actual edition of the standard compendium "The Merck Index" or from databases, e.g. IMS LifeCycle (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The invention in particular relates to a compound of formula (I), (IA), (IB), (IC) or (II) respectively, or a pharmaceutically acceptable salt thereof, for the treatment of the human or animal body.

The invention likewise relates to the use of the compounds of the formula I or of pharmaceutically acceptable salts of compounds of this type with salt-forming properties, in particular as pharmacological, primarily CETP inhibitors, active substances. In this connection, they can be used, preferably in the form of pharmaceutically acceptable preparations, in a method for the prophylactic and/or therapeutic treatment of the animal or human body, in particular as inhibitors of CETP.

The invention in particular relates to the use of a compound of formula (I), (IA), (IB), (IC) or (II) respectively, or a pharmaceutically acceptable salt thereof, optionally in combination with at least one composition for the treatment of cardiovascular diseases and related conditions and diseases listed hereinbefore or hereinafter, for the manufacture of a medicament for the prophylaxis or treatment of or delay progression to overt to diseases in which CETP is involved (e.g., hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.), particularly as prophylactic or therapeutic agents for hyperlipidemia or arteriosclerotic diseases.

The present invention likewise relates to a method for the prophylaxis or treatment of or delay progression to overt to diseases in which CETP is involved (e.g., hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.), particularly as prophylactic or therapeutic agents for hyperlipidemia or arteriosclerotic diseases, comprising administering to an animal, including man, in need thereof, a formula (I), (IA), (IB), (IC) or (II) respectively, or a pharmaceutically acceptable salt thereof, optionally in combination with at least one composition for the treatment of cardiovascular diseases and related conditions and diseases listed hereinbefore or hereinafter.

The present invention likewise relates to a pharmaceutical composition comprising a formula (I), (IA), (IB), (IC) or (II) respectively, or a pharmaceutically acceptable salt thereof, optionally in combination with at least one composition for the treatment of cardiovascular diseases and related conditions and diseases listed hereinbefore or hereinafter, for the prophylaxis or treatment of or delay progression to overt to diseases in which CETP is involved (e.g., hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.), particularly as prophylactic or therapeutic agents for hyperlipidemia or arteriosclerotic diseases.

The pharmaceutical preparations according to the invention which contain the compound according to the invention or pharmaceutically acceptable salts thereof are those for enteral, such as oral, furthermore rectal, and parenteral administration to (a) warm-blooded animal(s), the pharmacological active ingredient being present on its own or together with a pharmaceutically acceptable carrier. The daily dose of the active ingredient depends on the age and the individual condition and also on the manner of administration.

The dose of the active ingredient depends on the warm-blooded animal species, the age and the individual condition and on the manner of administration.

The following examples illustrate the invention described above; however, they are not intended to limit its extent in any manner. Temperatures are indicated in degrees Celsius.

EXAMPLES

Example 1

Synthesis of N-[(3-{N'-[3,5-bis(trifluoromethyl)benzyl]-N'-(2-methyl-2H-tetrazol-5-yl)amino}methyl)quinolin-2-yl]-N-(cyclopentylmethyl)ethylamine

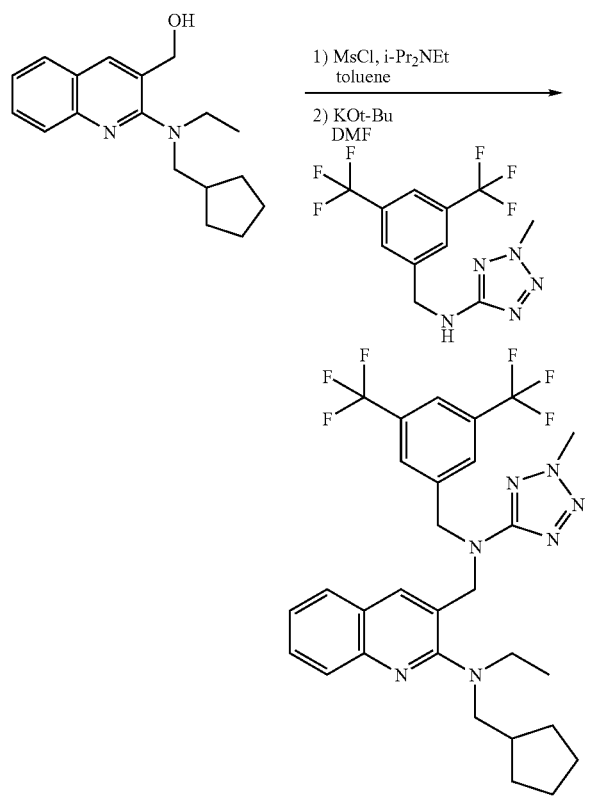

Methaneslufonyl chloride (MsCl, 15 mg, 0.13 mmol) is added dropwise to the solution of {2-[N-(cyclopentylmethyl)-N-ethylamino]quinolin-3-yl}methanol (25 mg, 0.088 mmol) and N,N-diisopropylethylamine (23 mg, 0.18 mmol) in toluene (1 mL) and the reaction mixture is stirred at ambient temperature for 2 hours. To the mixture, 1N HCl aq and ethyl acetate are added. The organic layer is washed with sat. NaHCO$_3$ aq, brine, dried over magnesium sulfate, filtered and concentrated in vacuo. After N-[3,5-bis(trifluoromethyl)benzyl]-N-(2-methyl-2H-tetrazol-5-yl)amine (29 mg, 0.089 mmol) and DMF (1 mL) are added to the residue, the mixture is stirred and then potassium tert-butoxide (11 mg, 0.098 mmol) is added and the mixture is further stirred for 1 hour. After adding 1N HCl aq, the mixture is extracted with ethyl acetate. The combined organic layer is washed with brine, dried over magnesium sulfate, filtrated, and concentrated. The resulting mixture is purified by silica gel column chromatography to give N-[(3-{N'-[3,5-bis(trifluoromethyl)benzyl]-N'-(2-methyl-2H-tetrazol-5-yl)amino]methyl)quinolin-2-yl}-N-(cyclopentylmethyl)ethylamine.

$^1$H-NMR (400 MHz, CDCl$_3$), δ (ppm): 1.03-1.10 (m, 2H), 1.08 (t, 3H), 1.37-1.60 (m, 6H), 2.03-2.20 (m, 1H), 3.18 (q, 2H), 3.23 (d, 2H), 4.22 (s, 3H), 4.67 (s, 2H), 4.83 (s, 2H), 7.32 (m, 1H), 7.56 (d, 1H), 7.57 (m, 1H), 7.66 (s, 2H), 7.72 (s, 1H), 7.78 (s, 1H), 7.85 (d, 1H).

ESI-MS m/z: 592 [M+1]$^+$

Example 2

The following compounds are prepared from substituted {2-[N-(cycloalkylmethyl)-N-ethylamino]quinolin-3-yl}methanol and N-[3,5-bis(trifluoromethyl)benzyl]-N-(2-methyl-2H-tetrazol-5-yl)amine following the procedure of example 1.

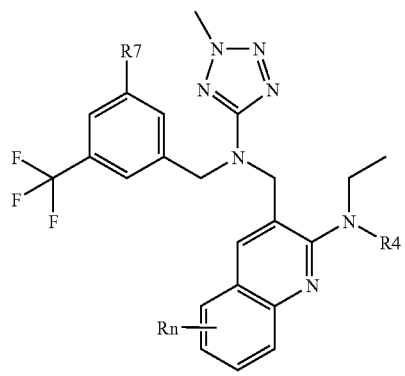

| No. | Rn | R$_4$ | R$_7$ | MS | $^1$H-NMR (400 MHz, CDCl$_3$), δ(ppm) or HPLC retention time |
|---|---|---|---|---|---|
| 2-1 | 6-F | ![cyclopentylmethyl] | CF$_3$ | 610 [M + 1]$^+$ | 1.03-1.10 (m, 2 H), 1.07 (t, 3 H), 1.37-1.60 (m, 6 H), 2.03-2.16 (m, 1 H), 3.15 (q, 2 H), 3.20 (d, 2 H), 4.23 (s, 3 H), 4.68 (s, 2 H), 4.82 (s, 2 H), 7.18 (dd, 1 H), 7.34 (ddd, 1 H), 7.65 (s, 2 H), 7.72 (s, 2 H), 7.83 (dd, 1 H). |

-continued

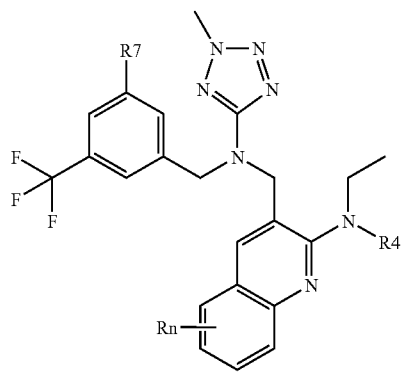

| No. | Rn | R₄ | R₇ | MS | ¹H-NMR (400 MHz, CDCl₃), δ(ppm) or HPLC retention time |
|---|---|---|---|---|---|
| 2-2 | 6-Cl | cyclopentylmethyl | CF₃ | 626 [M + 1]⁺ | 1.03-1.10 (m, 2 H), 1.08 (t, 3 H), 1.37-1.58 (m, 6 H), 2.08-2.20 (m, 1 H), 3.18 (q, 2 H), 3.22 (d, 2 H), 4.23 (s, 3 H), 4.66 (s, 2 H), 4.80 (s, 2 H), 7.50 (dd, 1 H), 7.54 (d, 1 H), 7.65 (s, 2 H), 7.68 (s, 1 H), 7.72 (s, 1 H), 7.77 (d, 1 H). |
| 2-3 | 6-OMe | cyclopentylmethyl | CF₃ | 622 [M + 1]⁺ | 1.03-1.10 (m, 2 H), 1.08 (t, 3 H), 1.37-1.58 (m, 6 H), 2.08-2.17 (m, 1 H), 3.12 (q, 2 H), 3.18 (d, 2 H), 3.86 (s, 3 H), 4.22 (s, 3 H), 4.69 (s, 2 H), 4.84 (s, 2 H), 6.88 (d, 1 H), 7.24 (dd, 1 H), 7.67 (s, 2 H), 7.69 (s, 1 H), 7.72 (s, 1 H), 7.77 (d, 1 H). |
| 2-4 | 7-F | cyclopentylmethyl | CF₃ | 610 [M + 1]⁺ | 1.03-1.10 (m, 2 H), 1.08 (t, 3 H), 1.37-1.60 (m, 6 H), 2.10-2.20 (m, 1 H), 3.19 (q, 2 H), 3.23 (d, 2 H), 4.23 (s, 3 H), 4.66 (s, 2 H), 4.80 (s, 2 H), 7.08 (ddd, 1 H), 7.46 (dd, 1 H), 7.51 (dd, 1 H), 7.64 (s, 2 H), 7.71 (s, 1 H), 7.74 (s, 1 H). |
| 2-5 | 7-Br | cyclopentylmethyl | CF₃ | 670, 672 [M + 1]⁺ | 1.02-1.10 (m, 2 H), 1.18 (t, 3 H), 1.40-1.58 (m, 6 H), 2.10-2.19 (m, 1 H), 3.19 (q, 2 H), 3.23 (d, 2 H), 4.22 (s, 3 H), 4.65 (s, 2 H), 4.78 (s, 2 H), 7.396 (s, 1 H), 7.400 (s, 1 H), 7.65 (s, 2 H), 7.71-7.77 (m, 2 H), 8.03 (s, 1 H). |
| 2-6 | 7-Me | cyclopentylmethyl | CF₃ | 606 [M + 1]⁺ | 1.03-1.10 (m, 2 H), 1.07 (t, 3 H), 1.35-1.60 (m, 6 H), 2.10-2.19 (m, 1 H), 2.51 (s, 3 H), 3.16 (q, 2 H), 3.22 (d, 2 H), 4.22 (s, 3 H), 4.65 (s, 2 H), 4.82 (s, 2 H), 7.17 (dd, 1 H), 7.46 (d, 1 H), 7.66 (s, 3 H), 7.72 (s, 1 H), 7.74 (s, 1 H). |
| 2-7 | 7-OMe | cyclopentylmethyl | CF₃ | 622 [M + 1]⁺ | 1.01-1.10 (m, 2 H), 1.21 (t, 3 H), 1.44-1.70 (m, 6 H), 2.20-2.30 (m, 1 H), 3.45-3.55 (m, 4 H), 3.97 (s, 3 H), 4.22 (s, 3 H), 4.71 (s, 2 H), 4.73 (s, 2 H), 7.08 (dd, 1 H), 7.48 (d, 1 H), 7.67 (s, 2 H), 7.76 (s, 1 H), 7.81 (br, 1 H), 7.91 (s, 1 H). |
| 2-8 | 6,7-F₂ | cyclopentylmethyl | CF₃ | 628 [M + 1]⁺ | 1.03-1.10 (m, 2 H), 1.07 (t, 3 H), 1.40-1.58 (m, 6 H), 2.08-2.16 (m, 1 H), 3.17 (q, 2 H), 3.21 (d, 2 H), 4.23 (s, 3 H), 4.66 (s, 2 H), 4.79 (s, 2 H), 7.27 (dd, 1 H), 7.58 (dd, 1 H), 7.64 (s, 2 H), 7.68 (s, 1 H), 7.72 (s, 1 H). |

-continued

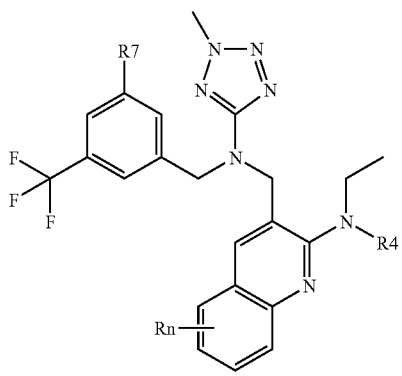

| No. | Rn | R4 | R7 | MS | $^1$H-NMR (400 MHz, CDCl$_3$), δ(ppm) or HPLC retention time |
|---|---|---|---|---|---|
| 2-9 | 5,7-F$_2$ | (cyclopentylmethyl) | CF$_3$ | 628.5 [M + 1]$^+$ | 1.03-1.10 (m, 2 H), 1.10 (t, 3 H), 1.41-1.55 (m, 6 H), 2.10-2.19 (m, 1 H), 3.23 (q, 2 H), 3.26 (d, 2 H), 4.23 (s, 3 H), 4.67 (s, 2 H), 4.79 (s, 2 H), 6.79 (ddd, 1 H), 7.27-7.30 (m, 1 H), 7.64 (s, 2 H), 7.71 (s, 1 H), 7.94 (s, 1 H). |
| 2-10 | 5,6,7-F$_3$ | (cyclopentylmethyl) | CF$_3$ | 646.6 [M + 1]$^+$ | 1.01-1.11 (m, 2 H), 1.09 (t, 3 H), 1.39-1.59 (m, 6 H), 2.07-2.17 (m, 1 H), 3.19-3.24 (m, 4 H), 4.23 (s, 3 H), 4.68 (s, 2 H), 4.79 (s, 2 H), 7.40 (ddd, 1 H), 7.64 (s, 2 H), 7.72 (s, 1 H), 7.94 (s, 1 H). |
| 2-11 | 5,7-Cl$_2$ | (cyclopentylmethyl) | CF$_3$ | 660 [M + 1]$^+$ | 1.02-1.10 (m, 2 H), 1.09 (t, 3 H), 1.41-1.60 (m, 6 H), 2.11-2.20 (m, 1 H), 3.24 (q, 2 H), 3.26 (d, 2 H), 4.22 (s, 3 H), 4.67 (s, 2 H), 4.81 (s, 2 H), 7.34 (d, 1 H), 7.64 (s, 2 H), 7.72 (s, 1 H), 7.74 (d, 1 H), 8.09 (s, 1 H). |
| 2-12 | 6-F | (cyclohexylmethyl) | CF$_3$ | 624 [M + 1]$^+$ | 0.75-0.85 (m, 2 H), 1.07 (t, 3 H), 1.05-1.13 (m, 3 H), 1.52-1.70 (m, 6 H), 3.11 (d, 2 H), 3.14 (q, 2 H), 4.22 (s, 3 H), 4.67 (s, 2 H), 4.83 (s, 2 H), 7.17 (dd, 1 H), 7.33 (ddd, 1 H), 7.64 (s, 2 H), 7.71 (s, 2 H), 7.82 (dd, 1 H). |
| 2-13 | 7-F | (cyclohexylmethyl) | CF$_3$ | 624 [M + 1]$^+$ | 0.75-0.85 (m, 2 H), 1.08 (t, 3 H), 1.05-1.13 (m, 3 H), 1.52-1.69 (m, 6 H), 3.15 (d, 2 H), 3.19 (q, 2 H), 4.22 (s, 3 H), 4.65 (s, 2 H), 4.80 (s, 2 H), 7.08 (ddd, 1 H), 7.45 (dd, 1 H), 7.50 (dd, 1 H), 7.63 (s, 2 H), 7.70 (s, 1 H), 7.73 (s, 1 H). |
| 2-14 | 7-Cl | (cyclohexylmethyl) | CF$_3$ | 640 [M + 1]$^+$ | 0.75-0.85 (m, 2 H), 1.08 (t, 3 H), 1.05-1.13 (m, 3 H), 1.54-1.68 (m, 6 H), 3.15 (d, 2 H), 3.18 (q, 2 H), 4.22 (s, 3 H), 4.65 (s, 2 H), 4.79 (s, 2 H), 7.25 (dd, 1 H), 7.46 (d, 1 H), 7.63 (s, 2 H), 7.70 (s, 1 H), 7.72 (s, 1 H), 7.83 (d, 1 H). |
| 2-15 | 6,7-F$_2$ | (cyclohexylmethyl) | CF$_3$ | 642 [M + 1]$^+$ | 0.75-0.85 (m, 2 H), 1.07 (t, 3 H), 1.05-1.13 (m, 3 H), 1.52-1.66 (m, 6 H), 3.12 (d, 2 H), 3.16 (q, 2 H), 4.22 (s, 3 H), 4.66 (s, 2 H), 4.80 (s, 2 H), 7.25 (dd, 1 H), 7.56 (dd, 1 H), 7.62 (s, 2 H), 7.67 (s, 1 H), 7.71 (s, 1 H). |

-continued

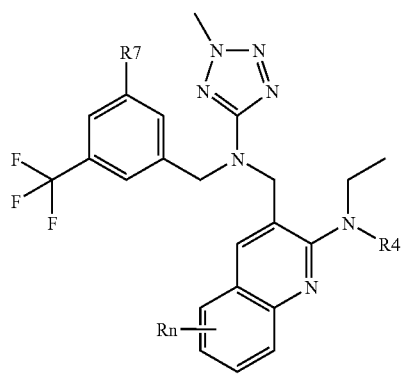

| No. | Rn | R₄ | R₇ | MS | ¹H-NMR (400 MHz, CDCl₃), δ(ppm) or HPLC retention time |
|---|---|---|---|---|---|
| 2-16 | 5,7-F₂ | (isobutyl-cyclohexyl) | CF₃ | 642 [M + 1]⁺ | 0.76-0.85 (m, 2 H), 1.09 (t, 3 H), 1.05-1.13 (m, 3 H), 1.54-1.68 (m, 6 H), 3.17 (d, 2 H), 3.22 (q, 2 H), 4.22 (s, 3 H), 4.66 (s, 2 H), 4.79 (s, 2 H), 6.77 (ddd, 1 H), 7.25 (d, 1 H), 7.62 (s, 2 H), 7.70 (s, 1 H), 7.92 (s, 1 H). |
| 2-17 | H | (isobutyl-cyclohexyl-CH₂CO₂Et) | CF₃ | 692 [M + 1]⁺ | 0.76-0.90 (m, 4 H), 1.08 (t, 3 H), 1.23 (t, 3 H), 1.25-1.30 (m, 1 H), 1.58-1.72 (m, 5 H), 2.10 (d, 2 H), 3.15 (q, 2 H), 3.16 (d, 2 H), 4.19 (q, 2 H), 4.22 (s, 3 H), 4.67 (s, 2 H), 4.83 (s, 2 H), 7.32 (m, 1 H), 7.54-7.59 (m, 2 H), 7.64 (s, 2 H), 7.71 (s, 1 H), 7.77 (s, 1 H), 7.83 (d, 1 H). |
| 2-18 | 6,7-F₂ | (isobutyl-cyclohexyl-CH₂CO₂Et) | CF₃ | 728.6 [M + 1]⁺ | 0.82-0.89 (m, 4 H), 1.08 (t, 3 H), 1.26 (t, 3 H), 1.55-1.73 (m, 6 H), 2.11 (d, 2 H), 3.14-3.19 (m, 4 H), 4.10-4.15 (m, 2 H), 4.22 (s, 3 H), 4.66 (s, 2 H), 4.78 (s, 2 H), 7.23-7.28 (m, 1 H), 7.59 (dd, 1 H), 7.62 (s, 2 H), 7.68 (s, 1 H), 7.71 (s, 1 H). |
| 2-19 | 7-F | (cyclohexyl) | CF₃ | 610 [M + 1]⁺ | 1.05-1.25 (m, 3 H), 1.10 (t, 3 H), 1.55-1.67 (m, 3 H), 1.75-1.83 (m, 4 H), 3.20-3.27 (m, 1 H), 3.73 (q, 2 H), 4.20 (s, 3 H), 4.70 (s, 2 H), 4.78 (s, 2 H), 6.77 (ddd, 1 H), 7.25 (ddd, 1 H), 7.63 (dd, 1 H), 7.70 (s, 2 H), 7.78 (s, 1 H), 7.91 (dd, 1 H), 8.08 (s, 1 H). |
| 2-20 | 7-F | (cyclopentyl-CH₂) | CF₃ | 596 [M + 1]⁺ | 0.95 (t, 3 H), 1.42-1.58 (m, 4 H), 1.60-1.70 (m, 2 H), 1.76-1.87 (m, 2 H), 3.30 (q, 2 H), 3.78-3.86 (m, 1 H), 4.22 (s, 3 H), 4.64 (s, 2 H), 4.82 (s, 2 H), 7.09-7.14 (m, 1 H), 7.51 (ddd, 1 H), 7.67 (s, 2 H), 7.72 (s, 1 H), 7.81 (s, 1 H). |

-continued

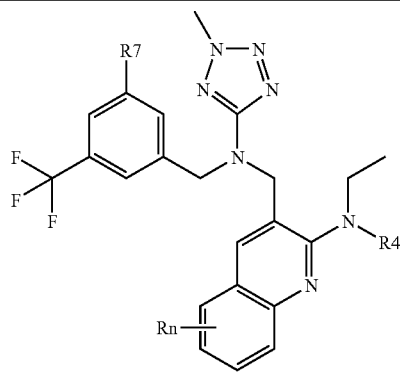

| No. | Rn | R4 | R7 | MS | $^1$H-NMR (400 MHz, CDCl$_3$), δ(ppm) or HPLC retention time |
|---|---|---|---|---|---|
| 2-21 | 6,7-F$_2$ | (cyclopentyl) | CF$_3$ | 614.5 [M + 1]$^+$ | 0.93 (t, 3 H), 1.42-1.61 (m, 4 H), 1.62-1.71 (m, 2 H), 1.75-1.83 (m, 2 H), 3.28 (q, 2 H), 3.75-3.84 (m, 1 H), 4.22 (s, 3 H), 4.65 (s, 2 H), 4.82 (s, 2 H), 7.30 (dd, 1 H), 7.57-7.65 (m, 1 H), 7.67 (s, 2 H), 7.73 (s, 1 H), 7.76 (s. 1 H). |
| 2-22 | 6,7-F$_2$ | (tetrahydropyranylethyl) | CF$_3$ | 644 [M + 1]$^+$ | 2.11 min |

Example 3

The following compounds are prepared from substituted quinolin-3-yl-methanol and N-[3,5-bis(trifluoromethyl)benzyl]-N-(2-methyl-2H-tetrazol-5-yl)amine following the procedure of example 1.

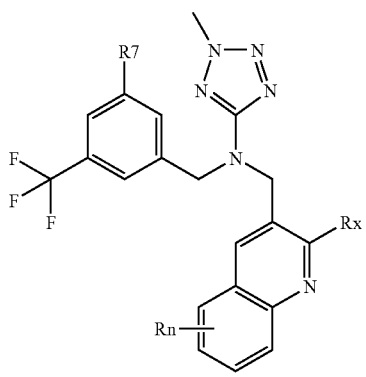

| No. | Rn | Rx | R7 | MS or Rf value | $^1$H-NMR (400 MHz, CDCl$_3$), δ(ppm) or HPLC retention time |
|---|---|---|---|---|---|
| 3-1 | 7-F | (N-cyclopropyl-N-cyclohexylmethyl isopropyl) | CF$_3$ | Rf = 0.19 (Hexane/AcOEt = 9/1) | 0.44-0.48 (m, 2 H), 0.70-0.77 (m, 2 H), 0.80-0.89 (m, 2 H), 1.05-1.20 (m, 3 H), 1.51-1.73 (m, 5 H), 1.77-1.81 (m, 1 H), 2.86-2.90 (m, 1 H), 3.35 (d, 2 H), 4.21 (s, 3 H), 4.68 (s, 2 H), 4.93 (s, 2 H), 7.01-7.06 (m, 1 H), 7.38 (dd, 1 H), 7.47 (dd, 1 H), 7.62 (s, 2 H), 7.64 (s, 1 H), 7.71 (s, 1 H). |

-continued
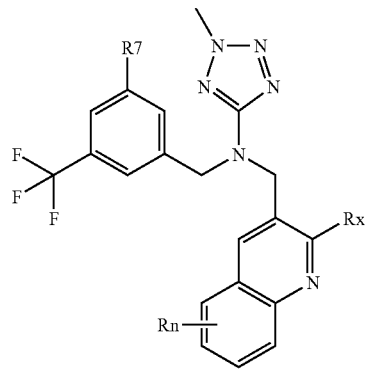
| No. | Rn | Rx | R7 | MS or Rf value | ¹H-NMR (400 MHz, CDCl₃), δ(ppm) or HPLC retention time |
|---|---|---|---|---|---|
| 3-2 | 7-F | 1-ethyl-2-cyclohexyl-pyrrolidine (racemate) | CF₃ | 636 [M + 1]⁺ | 0.97-1.25 (m, 5 H), 1.50-1.76 (m, 8 H), 1.85-1.90 (m, 1 H), 2.00-2.07 (m, 1 H), 3.22-3.29 (m, 1 H), 3.50-3.57 (m, 1 H), 4.20 (s, 3 H), 4.57 (d, 2 H), 4.64-4.70 (m, 1 H), 4.78 (d, 1 H), 4.98 (d, 1 H), 7.00 (ddd, 1 H), 7.37 (dd, 1 H), 7.45 (dd, 1 H), 7.62 (s, 1 H), 7.64 (s, 2 H), 7.72 (s, 1 H). |
| 3-3 | 6,7-F₂ | 1-ethyl-2-cyclohexyl-pyrrolidine 2-(R) | CF₃ | 654 [M + 1]⁺ | 0.93-2.05 (m, 15 H), 3.27-3.31 (m, 1 H), 3.52-3.58 (m, 1 H), 4.20 (s, 3 H), 4.59 (dd, 2 H), 4.56-4.69 (m, 1 H), 4.77 (d, 1 H), 4.99 (d, 1 H), 6.67-6.72 (m, 1 H), 7.17 (d, 2 H), 7.63 (s, 2 H), 7.72 (s, 1 H), 7.81 (s, 1 H). |
| 3-4 | 6,7-F₂ | 1-ethyl-2-(pent-3-yl)-pyrrolidine 2-(R) | CF₃ | 642 [M + 1]⁺ | 0.73 (t, 3 H), 0.81-0.94 (m, 1 H), 1.05 (t, 3 H), 1.18-1.50 (m, 4 H), 1.65-1.77 (m, 2 H), 1.88-2.04 (m, 2 H), 3.32-3.36 (m, 1 H), 3.55-3.61 (m, 1 H), 4.21 (s, 3 H), 4.58 (dd, 2 H), 4.74 (d, 1 H), 4.82-4.86 (m, 1 H), 5.01 (d, 1 H), 6.67-6.72 (m, 1 H), 7.15 (d, 1 H), 7.62 (s, 2 H), 7.72 (s, 1 H), 7.79 (s, 1 H). |

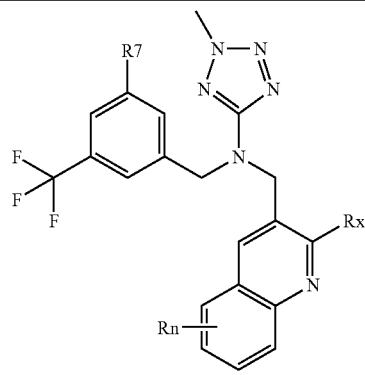

| No. | Rn | Rx | R7 | MS or Rf value | ¹H-NMR (400 MHz, CDCl₃), δ(ppm) or HPLC retention time |
|---|---|---|---|---|---|
| 3-5 | 7-F | (shown below) 2-(R) | CF₃ | Rf = 0.33 (Hexane/ AcOEt = 5/1) | 1.11 (t, 3 H), 1.76-1.96 (m, 3 H), 2.17-2.22 (m, 1 H), 3.34 (dd, 2 H), 3.44-3.51 (m, 2 H), 3.64 (dd, 2 H), 4.21 (s, 3 H), 4.57 (dd, 1 H), 4.60-4.80 (m, 1 H), 4.78 (d, 1 H), 5.02 (d, 1 H), 6.98-7.03 (m, 1 H), 7.36 (dd, 1 H), 7.48 (dd, 1 H), 7.64 (s, 2 H), 7.68 (s, 1 H), 7.71 (s, 1 H). |

Example 4

Synthesis of trans-[4-({N-[3-({N'-[3,5-bis(trifluoromethyl)benzyl]-N'-(2-methyl-2H-tetrazol-5-yl)amino}methyl)quinolin-2-yl]-N-ethylamino}methyl)cyclohexyl]acetic acid

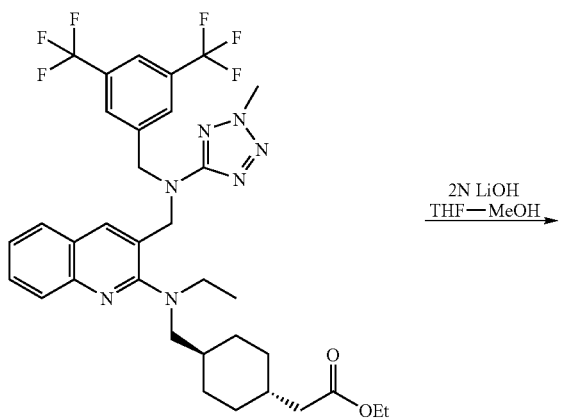

To a mixture of ethyl trans-[4-({N-[3-({N'-[3,5-bis(trifluoromethyl)benzyl]-N'-(2-methyl-2H-tetrazol-5-yl)amino}methyl)quinolin-2-yl]-N-ethylamino}methyl)cyclohexyl]acetate (39 mg, 0.056 mmol) in THF-methanol (2:1, 0.9 mL) is added 2N LiOH (0.1 mL) and the mixture is stirred at 40° C. for 3 hours. The mixture is diluted with 1N HCl and ethyl acetate, and the organic layer is washed with brine, dried over magnesium sulfate, filtered and concentrated to give trans-[4-({N-[3-({N'-[3,5-bis(trifluoromethyl)benzyl]-N'-(2-methyl-2H-tetrazol-5-yl)amino}methyl)quinolin-2-yl]-N-ethylamino}methyl)cyclohexyl]acetic acid.

¹H-NMR (400 MHz, CDCl₃), δ (ppm): 0.80-0.93 (m, 4H), 1.05-1.80 (m, 9H), 2.16 (2H, d), 3.00-3.55 (br, 4H), 4.21 (s, 3H), 4.72 (brs, 2H), 4.79 (brs, 2H), 7.57 (d, 1H), 7.65 (s, 2H), 7.73 (s, 1H), 7.73-8.10 (br, 4H).

ESI-MS m/z: 664 [M+1]⁺

Example 5

The following compounds are prepared from ethyl trans-[4-({N-[3-({N'-[3,5-bis(trifluoromethyl)benzyl]-N'-(2-methyl-2H-tetrazol-5-yl)amino}methyl)substituted quinolin-2-yl]-N-ethylamino}methyl)cyclohexyl]acetate following the procedure of example 4.

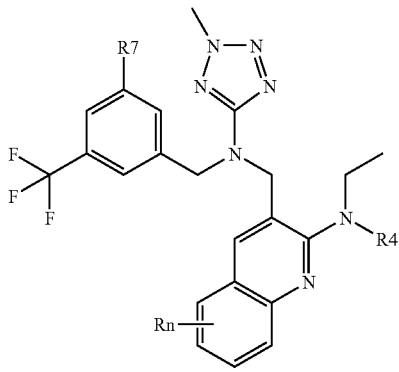

| No. | Rn | R₄ | R₇ | MS | ¹H-NMR (400 MHz, CDCl₃), δ(ppm) |
|---|---|---|---|---|---|
| 5-1 | 6,7-F₂ | (trans-4-carboxymethylcyclohexyl-methyl isobutyl group as drawn) | CF₃ | 700 [M + 1]⁺ | 0.84-0.92 (m, 4 H), 1.08 (t, 3 H), 1.45-2.04 (m, 6 H), 2.17 (d, 2 H), 3.15-3.21 (m, 4 H), 4.22 (s, 3 H), 4.67 (s, 2 H), 4.78 (s, 2 H), 7.29 (s, 1 H), 7.62 (s, 3 H), 7.69 (s, 1 H), 7.72 (s, 1 H). |

Example 6

Synthesis of 3-({N-[3,5-bis(trifluoromethyl)benzyl]-N-(2-methyl-2H-tetrazol-5-yl)amino}methyl)-2-[N'-(cyclopentylmethyl)-N'-ethylamino]quinoline-7-carbonitrile

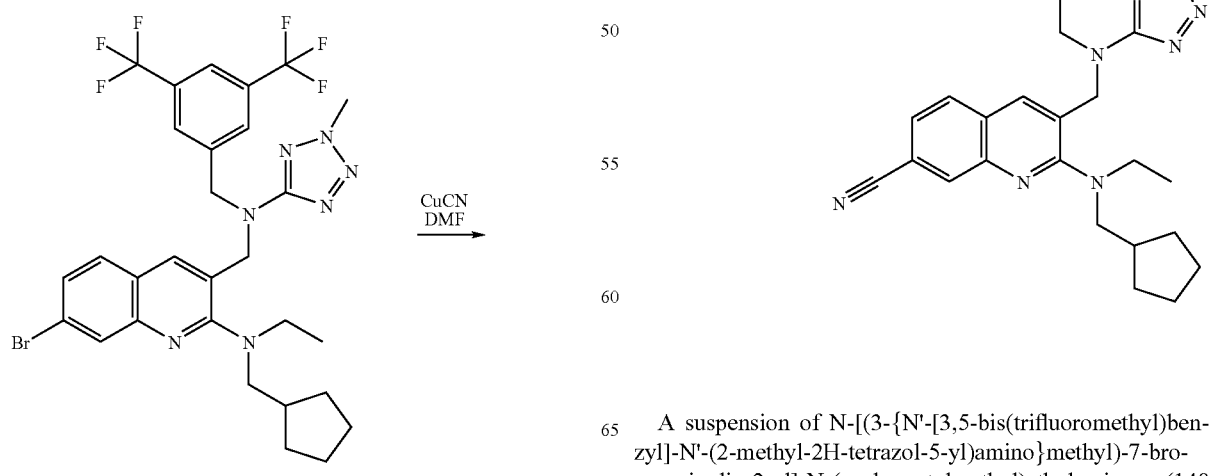

A suspension of N-[(3-{N'-[3,5-bis(trifluoromethyl)benzyl]-N'-(2-methyl-2H-tetrazol-5-yl)amino}methyl)-7-bromoquinolin-2-yl]-N-(cyclopentylmethyl)ethylamine (140 mg, 0.21 mmol) and CuCN (110 mg, 1.23 mmol) in DMF is stirred at 165° C. for 16 hours. The reaction mixture is cooled to room temperature and then diluted with ammonia water and ethyl acetate. The organic layer is washed with brine, dried over magnesium sulfate, filtered and concentrated. The crude product is purified by silica gel column chromatography to give 3-({N-[3,5-bis(trifluoromethyl)benzyl]-N-(2-methyl-2H-tetrazol-5-yl)amino}methyl)-2-[N'-(cyclopentylmethyl)-N'-ethylamino]quinoline-7-carbonitrile.

$^1$H-NMR (400 MHz, CDCl$_3$), δ (ppm): 1.03-1.12 (m, 2H), 1.10 (t, 3H), 1.41-1.60 (m, 6H), 2.11-2.20 (m, 1H), 3.23 (q, 2H), 3.26 (d, 2H), 4.23 (s, 3H), 4.67 (s, 2H), 4.80 (s, 2H), 7.44 (dd, 1H), 7.60 (d, 1H), 7.63 (s, 2H), 7.71 (s, 1H), 7.78 (s, 1H), 8.18 (s, 1H).

ESI-MS m/z: 617 [M+1]$^+$ mg, 0.06 mmol) and 2N LiOH aq. (2.0 mL) in EtOH (2 mL) is stirred and refluxed for 2 hours. The reaction mixture is cooled to room temperature and then diluted with 1N HCl and ethyl acetate. The organic layer is washed with brine, dried over magnesium sulfate, filtered and concentrated to give 3-({N-[3,5-bis(trifluoromethyl)benzyl]-N-(2-methyl-2H-tetrazol-5-yl)amino}methyl)-2-[N'-(cyclopentylmethyl)-N'-ethylamino]quinoline-7-carboxylic acid.

$^1$H-NMR (400 MHz, CDCl$_3$), δ (ppm): 1.03-1.15 (m, 2H), 1.12 (t, 3H), 1.41-1.60 (m, 6H), 2.12-2.22 (m, 1H), 3.22-3.30 (m, 4H), 4.23 (s, 3H), 4.70 (s, 2H), 4.83 (s, 2H), 7.62 (d, 1H), 7.70 (s, 2H), 7.73 (s, 1H), 7.83 (s, 1H), 7.95 (dd, 1H), 8.66 (s, 1H).

ESI-MS m/z: 636 [M+1]$^+$

Example 7

Synthesis of 3-({N-[3,5-bis(trifluoromethyl)benzyl]-N-(2-methyl-2H-tetrazol-5-yl)amino}methyl)-2-[N'-(cyclopentylmethyl)-N'-ethylamino]quinoline-7-carboxylic acid Example 8

Synthesis of 3-({N-[3,5-bis(trifluoromethyl)benzyl]-N-(2-methyl-2H-tetrazol-5-yl)amino}methyl)-2-[N'-(cyclopentylmethyl)-N'-ethylamino]quinoline-7-carboxylic acid dimethylamide

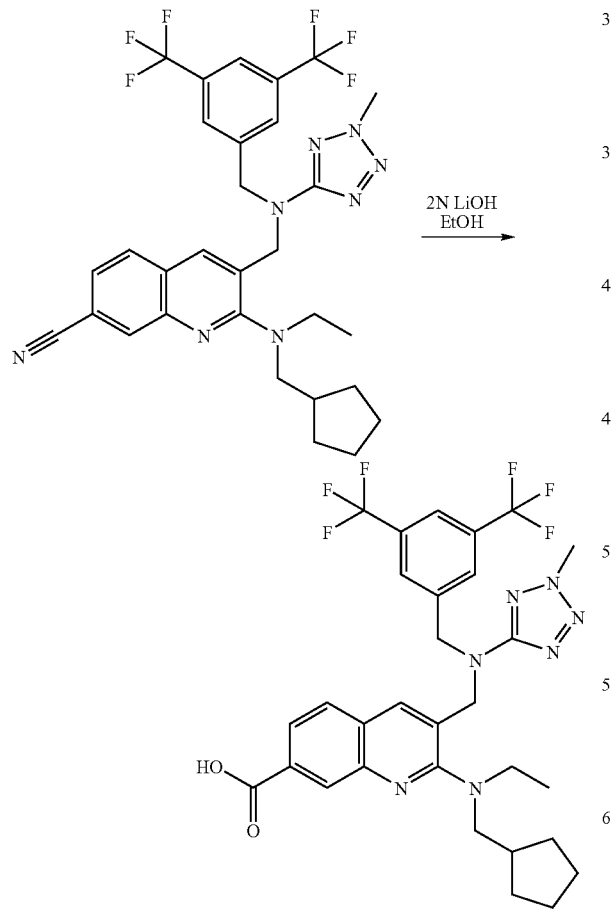

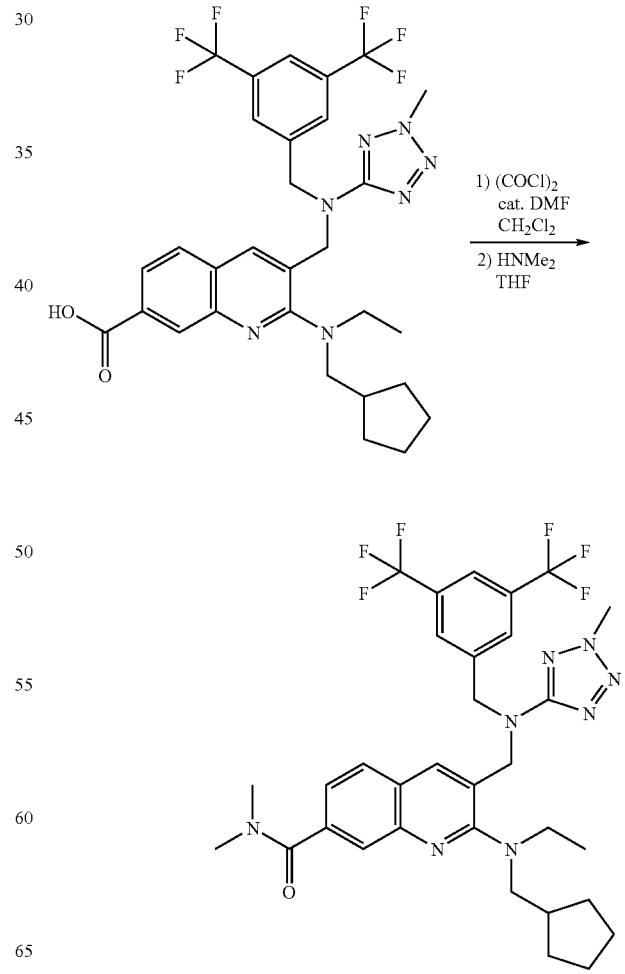

A suspension of 3-({N-[3,5-bis(trifluoromethyl)benzyl]-N-(2-methyl-2H-tetrazol-5-yl)amino}methyl)-2-[N'-(cyclopentylmethyl)-N'-ethylamino]quinoline-7-carbonitrile (40

A mixture of 3-({N-[3,5-bis(trifluoromethyl)benzyl]-N-(2-methyl-2H-tetrazol-5-yl)amino}methyl)-2-[N'-(cyclopentylmethyl)-N'-ethylamino]quinoline-7-carboxilic acid (30 mg, 0.047 mmol), oxalyl chloride (10 ul), and catalytic amount of DMF in $CH_2Cl_2$ (2 mL) is stirred at room temperature for 3 hours and concentrated in vacuo. The residue is dissolved with THF and treated with 2M dimethylamine in THF, and the resulting THF mixture is stirred at room temperature for 3 hours. The mixture is quenched by 1N HCl and extracted with EtOAc. The organic layer is washed with brine, dried over magnesium sulfate, filtered and concentrated. The crude product is purified by silica gel column chromatography to give 3-({N-[3,5-bis(trifluoromethyl)benzyl]-N-(2-methyl-2H-tetrazol-5-yl)amino}methyl)-2-[N'-(cyclopentylmethyl)-N'-ethylamino]quinoline-7-carboxylic acid dimethylamide.

$^1$H-NMR (400 MHz, $CDCl_3$), δ (ppm): 1.02-1.11 (m, 2H), 1.09 (t, 3H), 1.65-1.38 (m, 6H), 2.08-2.18 (m, 1H), 3.05 (s, 3H), 3.16 (s, 3H), 3.00-3.26 (m, 4H), 4.23 (s, 3H), 4.68 (s, 2H), 4.81 (s, 2H), 7.36 (d, 1H), 7.59 (d, 1H), 7.64 (s, 2H), 7.72 (s, 1H), 7.79 (s, 1H), 7.89 (s, 1H).

ESI-MS m/z: 663.7 $[M+1]^+$

Example 9

Synthesis of N-[3-({N'-[3,5-bis(trifluoromethyl)benzyl]-N'-(2-methyl-2H-tetrazol-5-yl)amino}methyl)-7-N'',N''-dimethylaminoquinolin-2-yl]-N-(cyclopentylmethyl)ethylamine

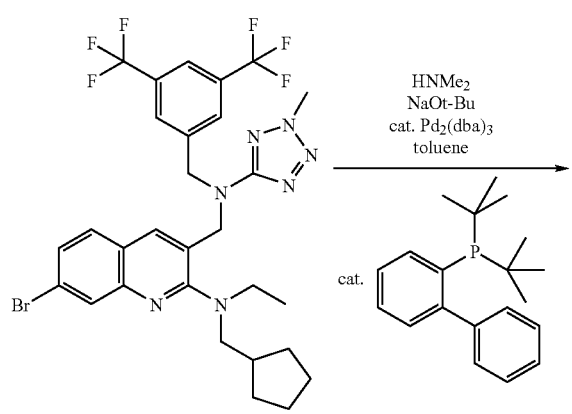

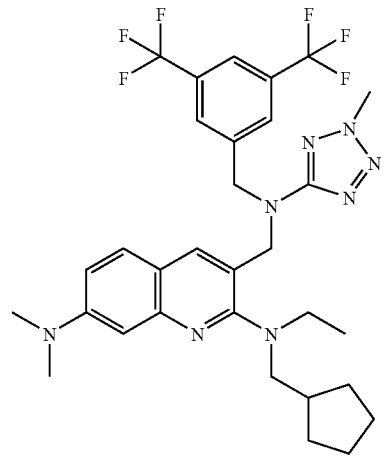

A suspension of N-[(3-{N'-[3,5-bis(trifluoromethyl)benzyl]-N'-(2-methyl-2H-tetrazol-5-yl)amino}methyl)-7-bromoquinolin-2-yl]-N-(cyclopentylmethyl)ethylamine (110 mg, 0.16 mmol), dimethylamine (2M in THF, 0.18 mL, 0.36 mmol), NaOt-Bu (25 mg, 0.26 mmol), $Pd_2(dba)_3$ (8 mg, 0.0087 mmol), and 2-(di-t-butylphosphino)biphenyl (5 mg, 0.017 mmol) in toluene (1 mL) is stirred at 10° C. for 4 hours. The reaction mixture is cooled to room temperature and diluted with water and ethyl acetate. The organic layer is washed with brine, dried over magnesium sulfate, filtered and concentrated. The crude product is purified by silica gel column chromatography to give N-[3-({N'-[3,5-bis(trifluoromethyl)benzyl]-N'-(2-methyl-2H-tetrazol-5-yl)amino}methyl)-7-N'',N''-dimethylaminoquinolin-2-yl]-N-(cyclopentylmethyl)ethylamine.

$^1$H-NMR (400 MHz, $CDCl_3$), δ (ppm): 1.02-1.11 (m, 2H), 1.04 (t, 3H), 1.37-1.63 (m, 6H), 2.11-2.20 (m, 1H), 3.07 (s, 6H), 3.15 (d, 2H), 3.86 (d, 2H), 4.21 (s, 3H), 4.63 (s, 2H), 4.80 (s, 2H), 6.95-6.98 (m, 2H), 7.40-7.43 (m, 1H), 7.63 (s, 1H), 7.66 (s, 2H), 7.72 (s, 1H).

ESI-MS m/z: 635.7 $[M+1]^+$

Example 10

The following compounds are prepared from N-[(3-{N'-[3,5-bis(trifluoromethyl)benzyl]-N'-(2-methyl-2H-tetrazol-5-yl)amino}methyl)-7-bromoquinolin-2-yl]-N-(cyclopentylmethyl)ethylamine following the procedure of example 9.

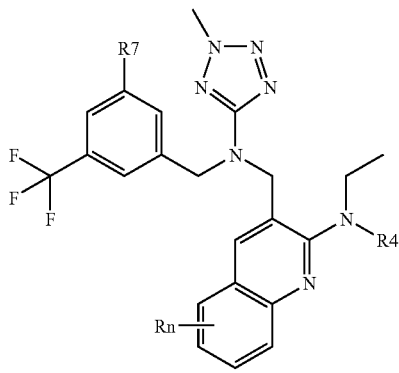

| No. | Rn | R₄ | R₇ | MS | ¹H-NMR (400 MHz, CDCl₃), δ(ppm) |
|---|---|---|---|---|---|
| 10-1 | 7-morpholine | (cyclopentylmethyl, ethyl) | CF₃ | 677 [M + 1]⁺ | 1.03-1.11 (m, 2 H), 1.07 (t, 3 H), 1.37-1.59 (m, 6 H), 2.09-2.18 (m, 1 H), 3.16 (q, 2 H), 3.20 (d, 2 H), 3.29-3.32 (m, 4 H), 3.89-3.91 (m, 4 H), 4.22 (s, 3 H), 4.64 (s, 2 H), 4.80 (s, 2 H), 7.07 (dd, 1 H), 7.16 (d, 1 H), 7.25-7.29 (m, 1 H), 7.65 (s, 2 H), 7.64-7.68 (m, 1 H), 7.71 (s, 1 H). |

Example 11

Synthesis of N-[3-({N'-[3,5-bis(trifluoromethyl)benzyl]-N'-(5-bromopyrimidin-2-yl)amino}methyl)-7-fluoroquinolin-2-yl]-N-(cyclopentylmethyl)ethylamine

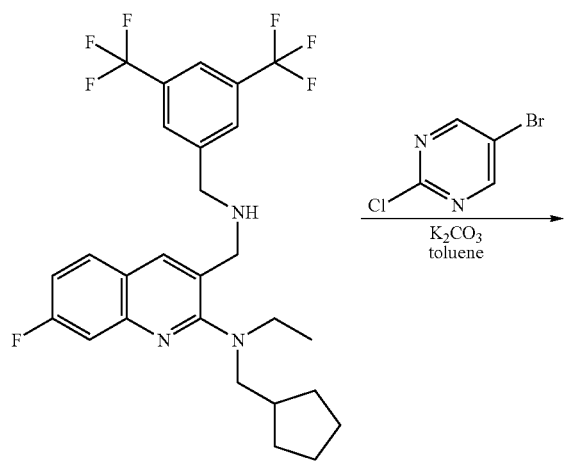

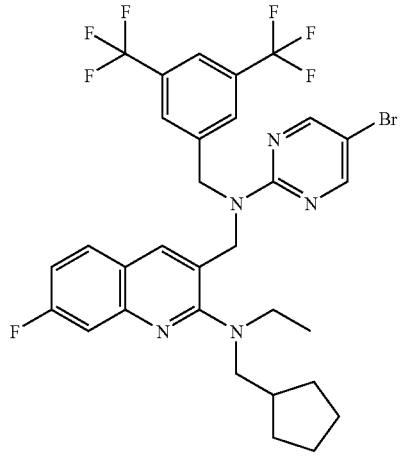

A suspension of N-(3-{N'-[3,5-bis(trifluoromethyl)benzylamino]methyl}-7-fluoroquinolin-2-yl)-N-(cyclopentylmethyl)ethylamine (610 mg, 1.2 mmol), 5-bromo-2-chloropyrimidine (449 mg, 2.3 mmol), and K₂CO₃ (321 mg, 2.3 mmol) in toluene is stirred and refluxed for 5 days. The reaction mixture is cooled to room temperature and then diluted with water and CH₂Cl₂. The organic layer is filtered through phase separator and concentrated. The crude product is purified by silica gel column chromatography to give N-[3-({N'-[3,5-bis(trifluoromethyl)benzyl]-N'-(5-bromopyrimidin-2-yl)amino}methyl)-7-fluoroquinolin-2-yl]-N-(cyclopentylmethyl)ethylamine.

Rf value=0.69 (Hexane/AcOAt=9/1)

¹H-NMR (400 MHz, CDCl₃), δ (ppm): 1.04-1.12 (m, 2H), 1.10 (t, 3H), 1.41-1.61 (m, 6H), 2.13-2.20 (m, 1H), 3.21 (dd, 2H), 3.25 (d, 2H), 4.80 (s, 2H), 4.95 (s, 2H), 7.08 (ddd, 1H), 7.48 (ddd, 1H), 7.52 (s, 1H), 7.65 (s, 2H), 7.72 (s, 1H), 8.42 (s, 2H).

Example 12

Synthesis of N-[3-({N'-[3,5-bis(trifluoromethyl)benzyl]-N'-(5-morpholin-4-yl-pyrimidin-2-yl)amino}methyl)-7-fluoroquinolin-2-yl]-N-(cyclopentylmethyl)ethylamine

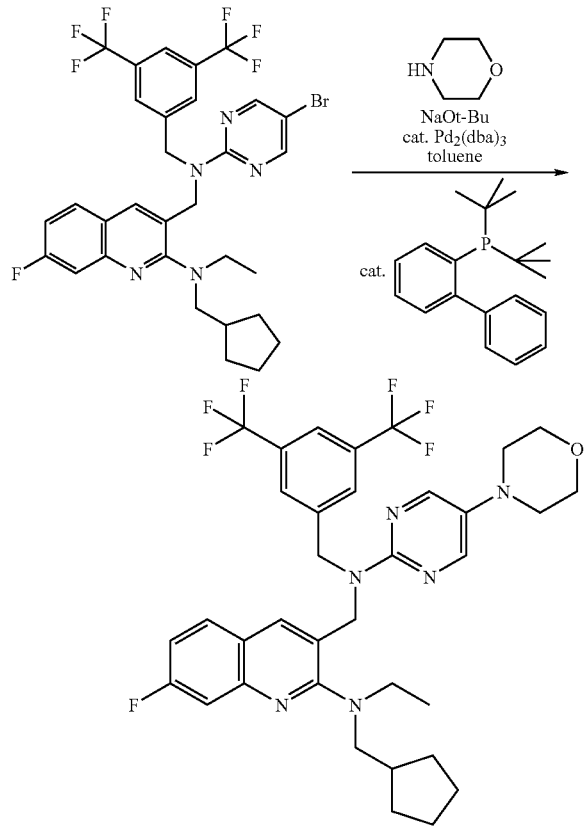

A suspension of N-[3-({N'-[3,5-bis(trifluoromethyl)benzyl]-N'-(5-bromopyrimidin-2-yl)amino}methyl)-7-fluoroquinolin-2-yl]-N-(cyclopentylmethyl)ethylamine (420 mg, 0.61 mmol), morpholine (80 µL, 0.93 mmol), NaOt-Bu (94 mg, 0.98 mmol), Pd$_2$(dba)$_3$ (28 mg, 0.031 mmol), and 2-(di-t-butylphosphino)biphenyl (18 mg, 0.060 mmol) in toluene (4 mL) is stirred at 100° C. for 2.5 hours. The reaction mixture is cooled to room temperature and then diluted with water and ethyl acetate. The organic layer is washed with brine, dried over magnesium sulfate, filtered and concentrated. The crude product is purified by silica gel column chromatography to give N-[3-({N'-[3,5-bis(trifluoromethyl)benzyl]-N'-(5-morpholin-4-yl-pyrimidin-2-yl)amino}methyl)-7-fluoroquinolin-2-yl]-N-(cyclopentylmethyl)ethylamine.

$^1$H-NMR (400 MHz, CDCl$_3$), δ (ppm): 0.87-1.11 (m, 2H), 1.09 (t, 3H), 1.38-1.62 (m, 6H), 2.13-2.20 (m, 1H), 3.07-3.09 (m, 4H), 3.18-3.27 (m, 4H), 3.87-3.90 (m, 4H), 4.81 (s 2H), 4.93 (s, 2H), 7.55-7.60 (m, 1H), 7.60 (s, 1H), 7.66 (s, 2H), 7.70 (s, 1H), 8.18 (s, 2H).

ESI-MS m/z: 691 [M+1]$^+$

Example 13

The following compounds are prepared from N-(3-{N'-[3,5-bis(trifluoromethyl)benzylamino]methyl}-substituted quinolin-2-yl)-N-(cyclopentylmethyl)ethylamine following the procedure of example 11 and 12.

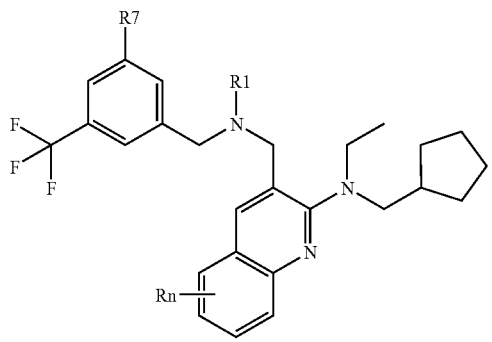

| No. | Rn | R1 | R7 | MS or Rf value | $^1$H-NMR (400 MHz, CDCl$_3$), δ(ppm) |
|---|---|---|---|---|---|
| 13-1 | 6,7-F$_2$ | Br-pyrimidin-2-yl | CF$_3$ | Rf = 0.79 (Hexane/AcOEt = 9/1) | 1.04-1.15 (m, 2 H), 1.09 (t, 3 H), 1.39-1.63 (m, 6 H), 2.10-2.20 (m, 1 H), 3.18 (dd, 2 H), 3.23 (d, 2 H), 4.81 (s, 2 H), 4.94 (s, 2 H), 7.23-7.28 (m, 1 H), 7.56 (s, 1 H), 7.58-7.61 (m, 1 H), 7.65 (s, 2 H), 7.72 (s, 1 H), 8.42 (s. 2 H). |

-continued
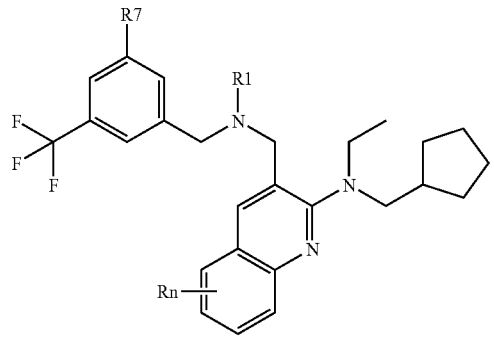
| No. | Rn | R1 | R7 | MS or Rf value | $^1$H-NMR (400 MHz, CDCl$_3$), δ(ppm) |
|---|---|---|---|---|---|
| 13-2 | 5,7-F$_2$ |  | CF$_3$ | 702, 704 [M + 1]$^+$ | 1.03-1.13 (m, 2 H), 1.11 (t, 3 H), 1.41-1.63 (m, 6 H), 2.14-2.22 (m, 1 H), 3.23 (q, 2 H), 3.27 (d, 2 H), 4.82 (s, 2 H), 4.94 (s, 2 H), 6.75-6.81 (m, 1 H), 7.25-7.29 (m, 1 H), 7.64 (s, 2 H), 7.72 (s, 1 H), 7.82 (s, 1 H), 8.41 (s, 2 H). |
| 13-3 | 6,7-F$_2$ | 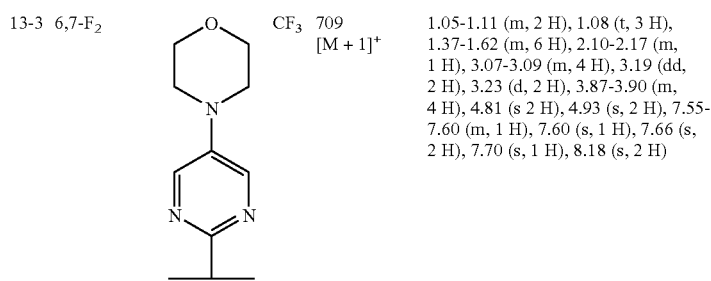 | CF$_3$ | 709 [M + 1]$^+$ | 1.05-1.11 (m, 2 H), 1.08 (t, 3 H), 1.37-1.62 (m, 6 H), 2.10-2.17 (m, 1 H), 3.07-3.09 (m, 4 H), 3.19 (dd, 2 H), 3.23 (d, 2 H), 3.87-3.90 (m, 4 H), 4.81 (s 2 H), 4.93 (s, 2 H), 7.55-7.60 (m, 1 H), 7.60 (s, 1 H), 7.66 (s, 2 H), 7.70 (s, 1 H), 8.18 (s, 2 H) |
| 13-4 | 5,7-F$_2$ | 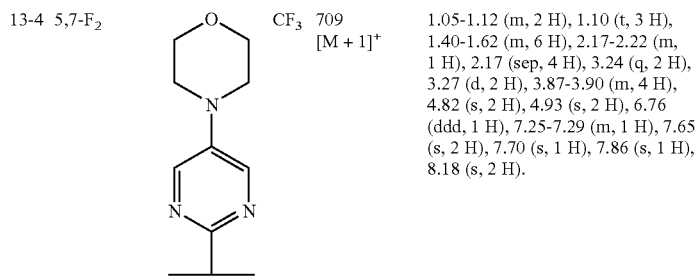 | CF$_3$ | 709 [M + 1]$^+$ | 1.05-1.12 (m, 2 H), 1.10 (t, 3 H), 1.40-1.62 (m, 6 H), 2.17-2.22 (m, 1 H), 2.17 (sep, 4 H), 3.24 (q, 2 H), 3.27 (d, 2 H), 3.87-3.90 (m, 4 H), 4.82 (s, 2 H), 4.93 (s, 2 H), 6.76 (ddd, 1 H), 7.25-7.29 (m, 1 H), 7.65 (s, 2 H), 7.70 (s, 1 H), 7.86 (s, 1 H), 8.18 (s, 2 H). |

Example 14

Synthesis of N-[3-({N'-[3,5-bis(trifluoromethyl)benzyl]-N'-[2-(2-hydroxyethyl)-2H-tetrazol-5-yl]amino}methyl)-5,7-difluoroquinolin-2-yl]-N-(cyclopentylmethyl)ethylamine

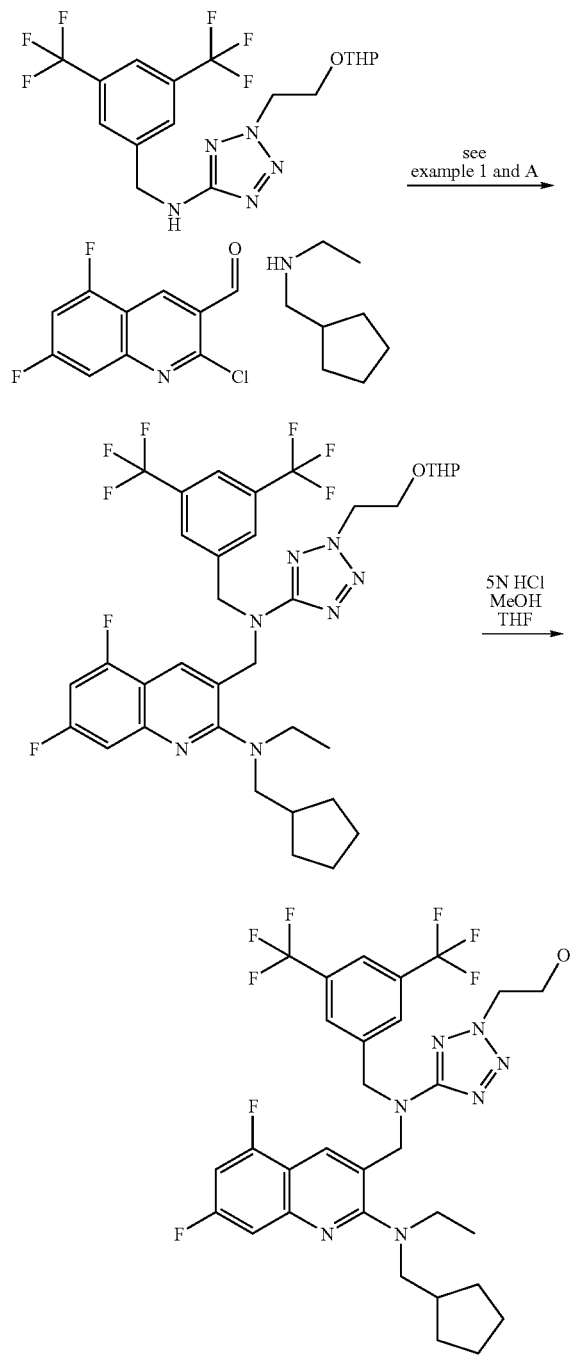

Step 1:

N-{3-[(N'-[3,5-bis(trifluoromethyl)benzyl]-N'-{2-[2-(tetrahydropyran-2-yloxy)ethyl]-2H-tetrazol-5-yl}amino)methyl]-5,7-difluoroquinolin-2-yl}-N-(cyclopentylmethyl)ethylamine is prepared from 2-chloro-5,7-difluoroquinoline-3-carbaldehyde, N-(cyclopentylmethyl)-N-ethylamine, and N-[3,5-bis(trifluoromethyl)benzyl]-N-{2-[2-(tetrahydropyran-2-yloxy)ethyl]-2H-tetrazol-5-yl}amine following the procedure of example 1 and A.

$^1$H-NMR (400 MHz, CDCl$_3$), δ (ppm): 1.03-1.12 (m, 2H), 1.11 (t, 3H), 1.41-1.79 (m, 12H), 2.12-2.22 (m, 1H), 3.20-3.26 (m, 4H), 3.43-3.49 (m, 1H), 3.67-3.73 (m, 1H), 3.97 (ddd, 1H), 4.20 (ddd, 1H), 4.58-4.61 (m, 1H), 4.63-4.69 (m, 4H), 4.80 (s, 2H), 6.75-6.80 (m, 1H), 7.25-7.28 (m, 1H), 7.64 (s, 2H), 7.71 (s, 1H), 7.93 (d, 1H).

ESI-MS m/z: 742 [M+1]$^+$

Step 2:

Aqueous 5 N HCl (0.2 mL) solution is added dropwise to a solution of N-{3-[(N'-[3,5-bis(trifluoromethyl)benzyl]-N'-{2-[2-(tetrahydropyran-2-yloxy)ethyl]-2H-tetrazol-5-yl}amino)methyl]-5,7-difluoroquinolin-2-yl}-N-(cyclopentylmethyl)ethylamine (0.25 g, 0.34 mmol) in MeOH/THF (¼, 2.5 mL) and the mixture is stirred at room temperature for 12 hours. The reaction mixture is quenched by addition of NaHCO$_3$ aqueous solution and extracted with ethyl acetate. The organic layer is washed with brine, dried over magnesium sulfate, filtered and concentrated to give N-[3-({N'-[3,5-bis(trifluoromethyl)benzyl]-N'-[2-(2-hydroxyethyl)-2H-tetrazol-5-yl]amino}methyl)-5,7-difluoroquinolin-2-yl]-N-(cyclopentylmethyl)ethylamine.

$^1$H-NMR (400 MHz, CDCl$_3$), δ (ppm): 1.03-1.12 (m, 2H), 1.10 (t, 3H), 1.41-1.62 (m, 6H), 2.12-2.22 (m, 1H), 2.29 (t, 1H), 3.21-3.26 (m, 4H), 4.14-4.16 (m, 2H), 4.62-4.65 (m, 2H), 4.67 (s, 2H), 4.81 (s, 2H), 6.76-6.81 (m, 1H), 7.26-7.28 (m, 1H), 7.64 (s, 2H), 7.72 (s, 1H), 7.95 (d, 1H).

ESI-MS m/z: 658 [M+1]$^+$

Example 15

Synthesis of N-[3-({N'-[3,5-bis(trifluoromethyl)benzyl]-N'-[2-(2-methoxyethyl)-2H-tetrazol-5-yl]amino}methyl)-5,7-difluoroquinolin-2-yl]-N-(cyclopentylmethyl)ethylamine

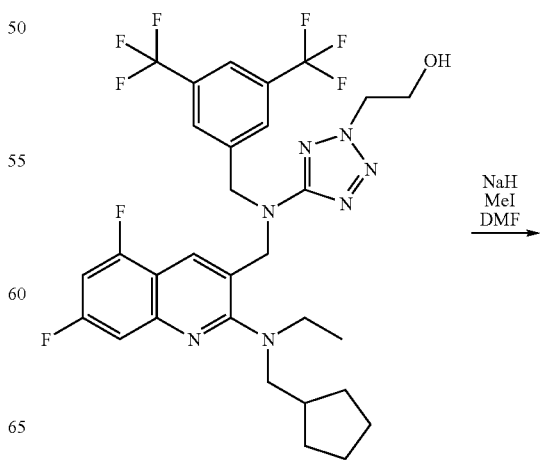

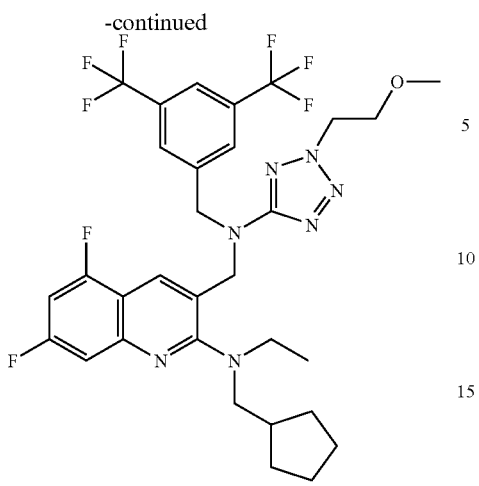

NaH (60% in oil, 5 mg, 0.13 mmol) is added to a solution of N-[3-({N'-[3,5-bis(trifluoromethyl)benzyl]-N'-[2-(2-hydroxyethyl)-2H-tetrazol-5-yl]amino}methyl)-5,7-difluoroquinolin-2-yl]-N-(cyclopentylmethyl)ethylamine (70 mg, 0.11 mmol) in DMF (0.5 mL) and stirred at 0° C. for 30 min. MeI (10 μL, 0.16 mmol) is added to the mixture and the resulting mixture is stirred at room temperature for 2 hours. The reaction mixture is quenched by addition of sat. NH₄Cl aq. and extracted with CH₂Cl₂. The organic layer is filtered through phase separator and concentrated. The crude product is purified by silica gel column chromatography to give N-[3-({N'-[3,5-bis(trifluoromethyl)benzyl]-N'-[2-(2-methoxyethyl)-2H-tetrazol-5-yl]amino}methyl)-5,7-difluoroquinolin-2-yl]-N-(cyclopentylmethyl)ethylamine.

Rf value=0.63 (Hexane/AcOEt=4/1)

¹H-NMR (400 MHz, CDCl₃), δ (ppm): 1.04-1.11 (m, 2H), 1.09 (t, 3H), 1.40-1.63 (m, 6H), 2.12-2.20 (m, 1H), 3.24 (t, 3H), 3.35 (s, 3H), 3.90 (t, 2H), 4.63-4.66 (m, 4H), 4.80 (s, 2H), 6.75-6.80 (m, 1H), 7.64 (s, 2H), 7.70 (s, 1H), 7.95 (s, 1H).

Example 16

Synthesis of N-{3-[(N'-[3,5-bis(trifluoromethyl)benzyl]-N'-{2-[2-(N'',N''-dimethylamino)ethyl]-2H-tetrazol-5-yl}amino)methyl]-5,7-difluoroquinolin-2-yl}-N-(cyclopentylmethyl)ethylamine

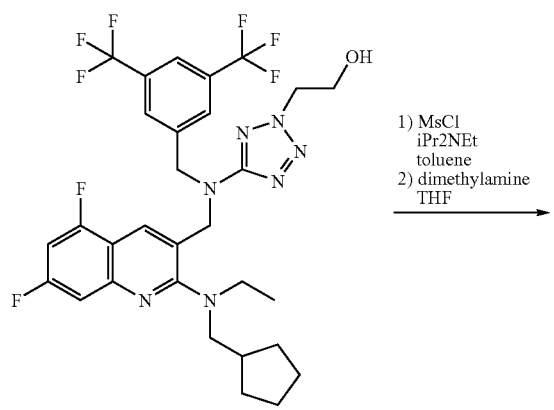

1) MsCl iPr2NEt toluene
2) dimethylamine THF

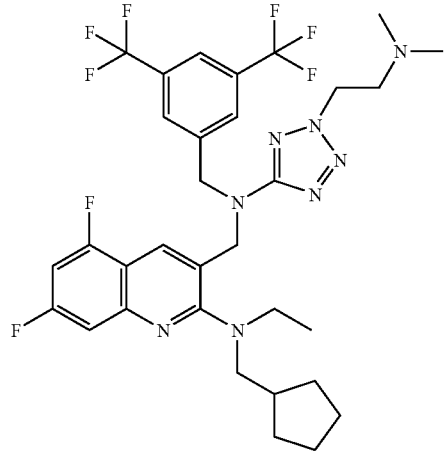

MsCl (20 mg, 0.17 mmol) is treated with a mixture of N-[3-({N'-[3,5-bis(trifluoromethyl)benzyl]-N'-[2-(2-hydroxyethyl)-2H-tetrazol-5-yl]amino}methyl)-5,7-difluoroquinolin-2-yl]-N-(cyclopentylmethyl)ethylamine (70 mg, 0.11 mmol) and N,N-diisopropylethylamine (25 mg, 0.19 mmol) in toluene (2 mL) and stirred at room temperature for 14 hours. The mixture is quenched by 1N HCl aq and extracted with EtOAc. The organic layer is washed with sat. NaHCO₃ aq and brine, dried over magnesium sulfate, filtered and concentrated to give the crude mesylate. The resulting mesylate is dissolved with 2M dimethylamine in THF (1.0 mL) and the mixture is stirred at 70° C. for 2 days. The reaction mixture is cooled to room temperature, diluted with water and CH₂Cl₂. The organic layer is filtered through phase separator and concentrated. The crude product is purified by silica gel column chromatography to give N-{3-[(N'-[3,5-bis(trifluoromethyl)benzyl]-N'-{2-[2-(N'',N''-dimethylamino)ethyl]-2H-tetrazol-5-yl}amino)methyl]-5,7-difluoroquinolin-2-yl}-N-(cyclopentylmethyl)ethylamine.

Rf value=0.22 (Hexane/AcOEt=3/1)

¹H-NMR (400 MHz, CDCl₃), δ (ppm): 1.02-1.13 (m, 2H), 1.10 (t, 3H), 1.39-1.65 (m, 6H), 2.12-2.20 (m, 1H), 2.29 (s, 6H), 2.88-2.98 (m, 2H), 3.21-3.26 (m, 4H), 4.57-4.60 (m, 2H), 4.65 (s, 2H), 4.80 (s, 2H), 6.75-7.00 (m, 1H), 7.24-7.29 (m, 1H), 7.64 (s, 2H), 7.71 (s, 1H), 7.95 (s, 1H).

Example 17

Synthesis of trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)methanol

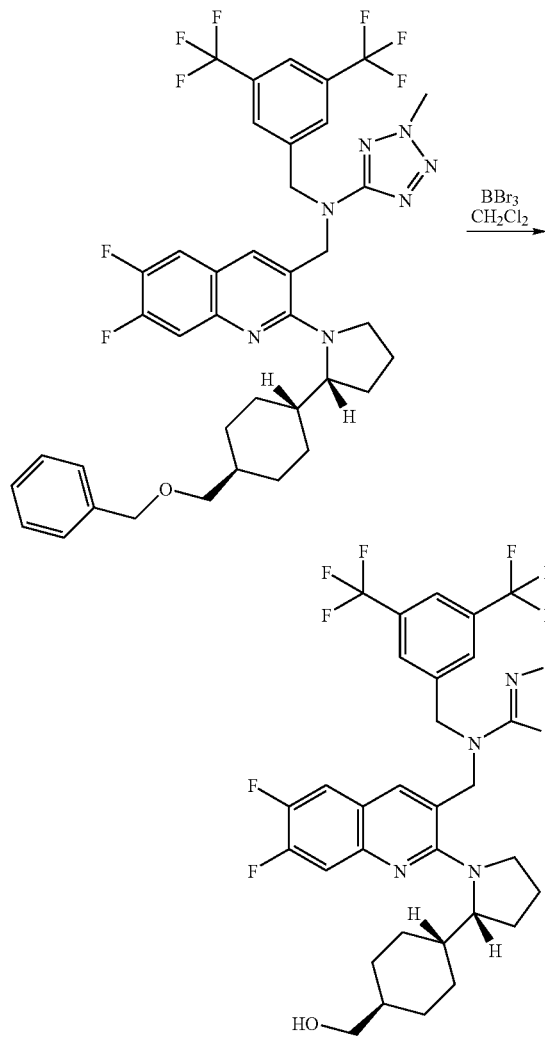

To a stirred solution of trans-N-(2-{(R)-2-[4-(2-benzyloxymethyl)cyclohexyl]pyrrolidin-1-yl}-6,7-difluoroquinolin-3-ylmethyl)-N-[3,5-bis(trifluoromethyl)benzyl](2-methyl-2H-tetrazol-5-yl)amine (7.47 g, 9.7 mmol) in CH$_2$Cl$_2$ (80 mL) is added dropwise BBr$_3$ (1.0 M CH$_2$Cl$_2$ solution, 11.6 mL, 11.6 mmol) at 0° C., and stirred at room temperature for 1 hour. The reaction mixture is quenched by addition of sat. NaHCO$_3$ aq. at 0° C. and extracted with ethyl acetate, and the organic layer is washed with brine, dried over magnesium sulfate, filtered and concentrated. The crude product is purified by silica gel column chromatography to give trans-2-(4-{(R)-1-[3-({[N-3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)methanol.

$^1$H-NMR (400 MHz, CDCl$_3$), δ (ppm): 0.73-0.95 (m, 2H), 1.00-1.13 (m, 2H), 1.21 (t, 1H), 1.34-1.44 (m, 1H), 1.57-1.61 (m, 1H), 1.64-1.79 (m, 6H), 1.83-1.92 (m, 1H), 1.98-2.02 (m, 1H), 3.18-3.24 (m, 1H), 3.39 (t, 2H), 3.48-3.57 (m, 1H), 4.21 (s, 3H), 4.56 (d, 1H), 4.57 (d, 1H), 4.62-4.70 (m, 1H), 4.78 (d, 1H), 4.99 (d, 1H), 7.22 (dd, 1H), 7.48 (dd, 1H), 7.56 (s, 1H), 7.63 (s, 2H), 7.73 (s, 1H).

ESI-MS m/z: 684 [M+1]$^+$

Example 18

The following compounds are prepared from trans-N-(2-{(R)-2-[4-(2-benzyloxymethyl)cyclohexyl]pyrrolidin-1-yl}-substituted-quinolin-3-ylmethyl)-N—[substituted-benzyl](2-methyl-2H-tetrazol-5-yl)amine following the procedure of example 17.

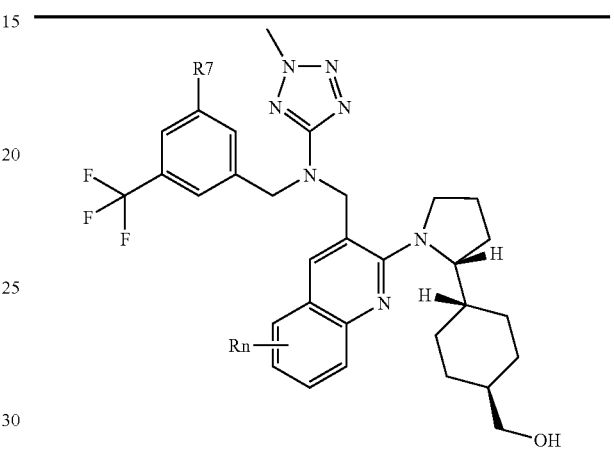

| No. | Rn | R$_7$ | MS | $^1$H-NMR (400 MHz, CDCl$_3$), δ(ppm) |
|---|---|---|---|---|
| 18-1 | 7-F | CF$_3$ | 666 [M + 1]$^+$ | 0.74-0.96 (m, 2 H), 1.01-1.14 (m, 2 H), 1.21 (t, 1 H), 1.34-1.44 (m, 1 H), 1.54-1.61 (m, 1 H), 1.66-1.79 (m, 6 H), 1.83-1.93 (m, 1 H), 1.98-2.05 (m, 1 H), 3.22-3.28 (m, 1 H), 3.39 (t, 2 H), 3.51-3.59 (m, 1 H), 4.20 (s, 3 H), 4.58 (d, 1 H), 4.59 (d, 1 H), 4.67-4.73 (m, 1 H), 4.77 (d, 1 H), 4.98 (d, 1 H), 7.00 (1 H, ddd), 7.37 (dd, 1 H), 7.46 (dd, 1 H), 7.62-7.65 (m, 3 H), 7.72 (s. 1 H). |
| 18-2 | 7-F | Cl | 632 [M + 1]$^+$ | 0.75-0.96 (m, 2 H), 1.01-1.13 (m, 2 H), 1.21 (t, 1 H), 1.34-1.45 (m, 1 H), 1.51-1.61 (m, 1 H), 1.66-1.80 (m, 6 H), 1.85-1.92 (m, 1 H), 1.97-2.05 (m, 1 H), 3.22-3.27 (m, 1 H), 3.40 (t, 2 H), 3.51-3.59 (m, 1 H), 4.21 (s, 3 H), 4.46 (d, 1 H), 4.55 (d, 1 H), 4.66-4.73 (m, 1 H), 4.73 (d, 1 H), 4.95 (d, 1 H), 7.00 (1 H, ddd), 7.31 (1 H, s), 7.33 (1 H, s), 7.37 (dd, 1 H), 7.44 (1 H, s), 7.47 (dd, 1 H), 7.62 (s, 1 H). |
| 18-3 | 6,7-F$_2$ | Cl | 651 [M + 1]$^+$ | 0.77-0.98 (m, 2 H), 1.11-1.14 (m, 2 H), 1.19 (dd, 1 H), 1.29-1.44 (m, 1 H), 1.55-1.63 (m, 1 H), 1.66-1.80 (m, 6 H), 1.84-1.93 (m, 1 H), 1.97-2.07 (m, 1 H), 3.21 (dd, 1 H), 3.40 |

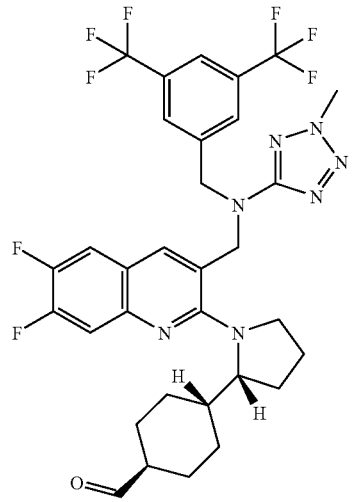

| No. | Rn | R7 | MS | ¹H-NMR (400 MHz, CDCl₃), δ(ppm) |
|---|---|---|---|---|
| | | | | (dd, 2 H), 3.49-3.57 (m, 1 H), 4.21 (s, 3 H), 4.47 (d, 1 H), 4.52 (d, 1 H), 4.66 (dd, 1 H), 4.74 (d, 1 H), 4.96 (d, 1 H), 7.23 (dd, 1 H), 7.32 (d, 2 H), 7.45 (s, 1 H), 7.48 (dd, 1 H), 7.56 (s, 1 H). |

Example 19

Synthesis of trans-4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexanecarbaldehyde

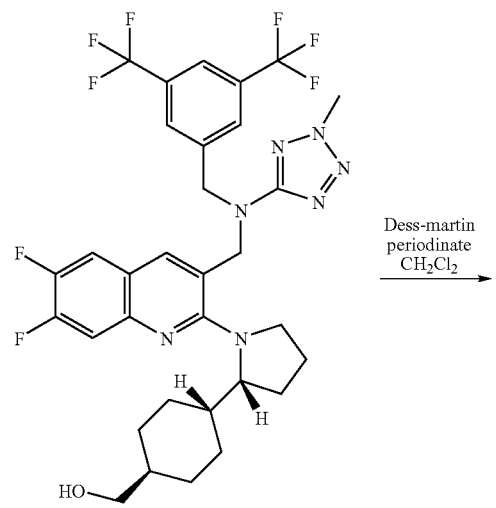

Dess-Martin periodinate (4.07 g, 9.6 mmol) is added to a suspension of trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)methanol (6.25 g, 9.1 mmol) in CH₂Cl₂ (75 mL) at 0° C., and the resulting mixture is stirred at room temperature for 20 min. The reaction mixture is quenched by addition of sat. NaHCO₃ aq. and extracted with CH₂Cl₂. The combined organic layer is washed with brine, dried over magnesium sulfate, filtered and concentrated. The crude product is purified by silica gel column chromatography to give trans-4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexanecarbardehyde.

¹H-NMR (400 MHz, CDCl₃), δ (ppm): 1.04-1.28 (m, 4H), 1.65-2.15 (m, 10H), 3.19-3.25 (m, 1H), 3.50-3.57 (m, 1H), 4.20 (s, 3H), 4.56 (d, 1H), 4.60 (d, 1H), 4.66-4.73 (m, 1H), 4.81 (d, 1H), 4.97 (d, 1H), 7.23 (dd, 1H), 7.48 (dd, 1H), 7.57 (s, 1H), 7.65 (s, 2H), 7.74 (s, 1H), 9.55 (d, 1H).

ESI-MS m/z: 682 [M+1]⁺

Example 20

The following compounds are prepared from trans-(4-{(R)-1-[3-({N—[substituted-benzyl]-N-(2-methyl-2H-tetrazol-5-yl)amino}methyl)-substituted-quinolin-2-yl]pyrrolidin-2-yl}cyclohexyl)methanol following the procedure of example 19.

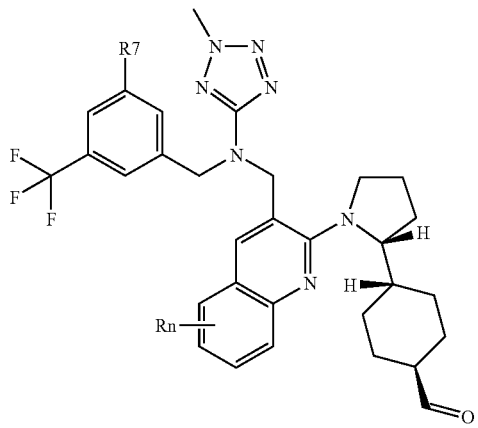

| No. | Rn | R7 | MS | $^1$H-NMR (400 MHz, CDCl$_3$), δ(ppm) |
|---|---|---|---|---|
| 20-1 | 7-F | CF$_3$ | 664 [M + 1]$^+$ | 1.04-1.25 (m, 4 H), 1.65-2.16 (m, 10 H), 3.22-3.29 (m, 1 H), 3.51-3.58 (m, 1 H), 4.20 (s, 3 H), 4.59 (d, 1 H), 4.60 (d, 1 H), 4.71-4.77 (m, 1 H), 4.79 (d, 1 H), 4.96 (d, 1 H), 7.02 (ddd, 1 H), 7.37 (dd, 1 H), 7.47 (dd, 1 H), 7.63 (s, 1 H), 7.64 (s, 2 H), 7.73 (s, 1 H), 9.55 (d, 1 H). |
| 20-2 | 7-F | Cl | 630 [M + 1]$^+$ | 1.04-1.25 (m, 4 H), 1.65-2.16 (m, 10 H), 3.22-3.28 (m, 1 H), 3.51-3.58 (m, 1 H), 4.20 (s, 3 H), 4.48 (d, 1 H), 4.56 (d, 1 H), 4.71-4.77 (m, 1 H), 4.75 (d, 1 H), 4.94 (d, 1 H), 7.02 (ddd, 1 H), 7.32 (s, 1 H), 7.34 (s, 1 H), 7.35 (dd, 1 H), 7.38 (s, 1 H), 7.48 (dd, 1 H), 7.63 (s, 1 H), 9.56 (d, 1 H). |
| 20-3 | 6,7-F$_2$ | Cl | 649 [M + 1]$^+$ | 1.04-1.29 (m, 4 H), 1.67-2.17 (m, 10 H), 3.20-3.27 (m, 1 H), 3.50-3.57 (m, 1 H), 4.20 (s, 3 H), 4.49 (d, 1 H), 4.53 (d, 1 H), 4.69 (dd, 1 H), 4.76 (d, 1 H), 4.95 (d, 1 H), 7.22-7.28 (m, 1 H), 7.33 (d, 2 H), 7.46 (s, 1 H), 7.48 (dd, 1 H), 7.57 (s, 1 H), 9.56 (d, 1 H). |

Example 21

Synthesis of trans-4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexanecarboxylic acid

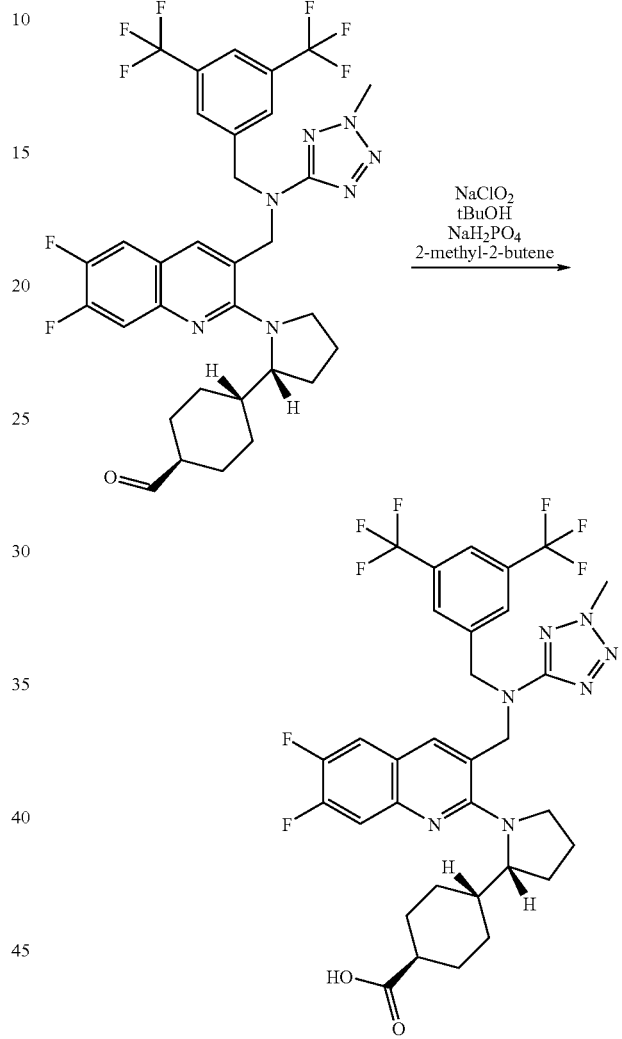

A mixture of NaClO$_2$ (2.20 g, 24 mmol) and NaH$_2$PO$_4$ (2.19 g 18 mmol) in water (40 mL) is added dropwise to a solution of trans-4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexanecarbardehyde (4.15 g, 6.1 mmol) in 2-methyl-2-butene (6.4 mL)/t-BuOH (40 mL) at 0° C., and the resulting mixture is stirred at room temperature for 1.5 hours. The reaction mixture is quenched by addition of sat. NH$_4$Cl aq. at 0° C. and extracted with ethyl acetate. The organic layer is washed with brine, dried over magnesium sulfate, filtered concentrated. The crude product is purified by silica gel column chromatography to give trans-4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexanecarboxylic acid.

$^1$H-NMR (400 MHz, CDCl$_3$), δ (ppm): 1.01-1.14 (m, 2H), 1.22-1.43 (m, 2H), 1.55-1.80 (m, 5H), 1.85-2.05 (m, 4H), 2.21 (tt, 1H), 3.17-3.24 (m, 1H), 3.49-3.56 (m, 1H), 4.19 (s, 3H), 4.57 (d, 1H), 4.60 (d, 1H), 4.64-4.70 (m, 1H), 4.79 (d, 1H), 4.95 (d, 1H), 7.23 (dd, 1H), 7.47 (dd, 1H), 7.57 (s, 1H), 7.64 (s, 2H), 7.74 (s, 1H).

ESI-MS m/z: 698 [M+1]⁺

Example 22

The following compounds are prepared from trans-(4-{(R)-1-[3-({N-substituted-benzyl]-N-(2-methyl-2H-tetrazol-5-yl)amino}methyl)-substituted-quinolin-2-yl]pyrrolidin-2-yl}cyclohexyl)methanol following the procedure of example 21.

| No. | Rn | R₇ | MS | ¹H-NMR (400 MHz, CDCl₃), δ(ppm) |
|-----|-----|-----|-----|-----|
| 22-1 | 7-F | CF₃ | 680 [M + 1]⁺ | 1.04-1.15 (m, 2 H), 1.20-1.45 (m, 2 H), 1.55-1.80 (m, 5 H), 1.85-2.05 (m, 4 H), 2.21 (tt, 1 H), 3.22-3.28 (m, 1 H), 3.51-3.58 (m, 1 H), 4.19 (s, 3 H), 4.60 (d, 2 H), 4.68-4.76 (m, 1 H), 4.78 (d, 1 H), 4.94 (d, 1 H), 7.02 (ddd, 1 H), 7.36 (dd, 1 H), 7.47 (dd, 1 H), 7.63 (s, 1 H), 7.64 (s, 2 H), 7.73 (s. 1 H). |
| 22-2 | 7-F | Cl | 646 [M + 1]⁺ | 1.02-1.14 (m, 2 H), 1.23-1.45 (m, 2 H), 1.55-1.80 (m, 5 H), 1.85-2.05 (m, 4 H), 2.22 (tt, 1 H), 3.21-3.28 (m, 1 H), 3.51-3.58 (m, 1 H), 4.19 (s, 3 H), 4.49 (d, 1 H), 4.57 (d, 1 H), 4.69-4.75 (m, 1 H), 4.74 (d, 1 H), 4.92 (d, 1 H), 7.01 (ddd, 1 H), 7.33 (s, 2 H), 7.37 (dd, 1 H), 7.45 (s, 1 H), 7.48 (dd, 1 H), 7.62 (s, 1 H) |
| 22-3 | 6,7-F₂ | Cl | 665 [M + 1]⁺ | 1.03-1.15 (m, 2 H), 1.25-1.44 (m, 2 H), 1.60-1.82 (m, 5 H), 1.84-1.94 (m, 1 H), 1.96-2.07 (m, 3 H), 2.17-2.27 (m, 1 H), 3.19-3.27 (m, 1 H), 3.48-3.60 (m, 1 H), 4.20 (s, 3 H), 4.51 (dd, 1 H), 4.54 (d, 1 H), 4.64-4.75 (m, 1 H), 4.75 (d, 1 H), 4.92 (d, 1 H), 7.21-7.28 (m, 1 H), 7.33 (s, 2 H), 7.46 (s, 2 H), 7.57 (s, 1 H). |

Example 23

Synthesis of trans-4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexanecarboxylic acid amide

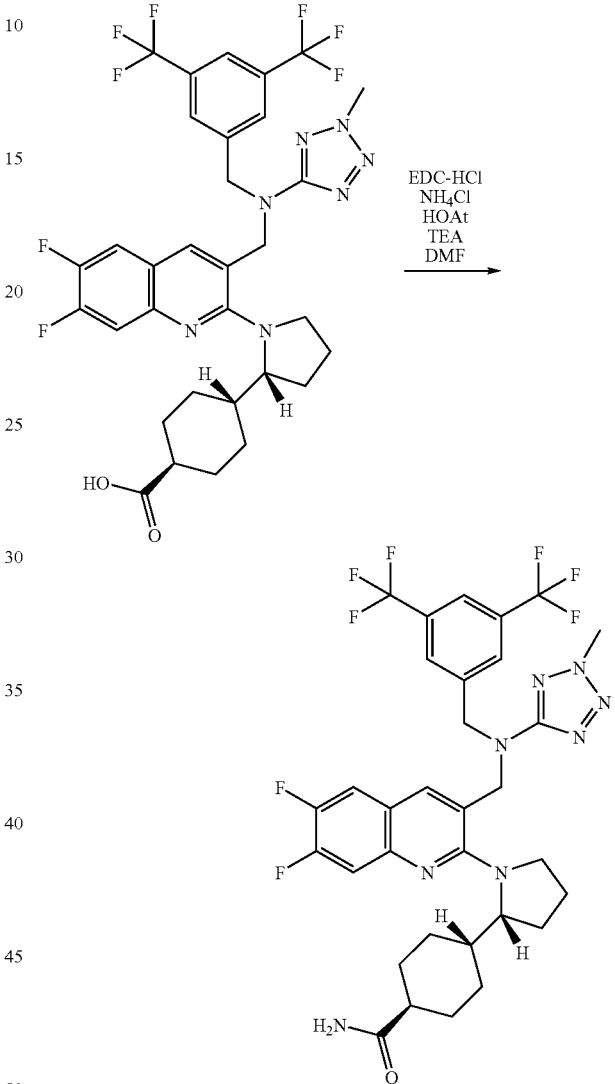

A mixture of trans-(4-{(R)-1-[3-({N—[substituted-benzyl]-N-(2-methyl-2H-tetrazol-5-yl)amino}methyl)-substituted-quinolin-2-yl]pyrrolidin-2-yl}cyclohexyl)acetic acid (135 mg, 0.19 mmol), NH₄Cl (21 mg, 0.38 mmol), N-ethyl-N'-(3-dimethylaminopropyl)carbodiimide hydrochloride (EDC.HCl, 56 mg, 0.29 mmol), 1-hydroxy-7-azabenzotriazole (HOAt, 26 mg, 0.19 mmol) and triethylamine (0.054 mL, 0.38 mmol) in DMF (1 mL) is stirred at room temperature for 3 h. After adding H₂O, the reaction mixture is extracted with EtOAc. The organic layer is washed with brine, dried over Na₂SO₄ and concentrated in vacuo. The residue is purified by silica-gel column chromatography to give trans-4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexanecarboxylic acid amide as a colorless syrup.

¹H-NMR (400 MHz, CDCl₃), δ (ppm): 1.03-1.16 (m, 2H), 1.24-1.35 (m, 2H), 1.35-1.45 (m, 2H), 1.63-1.81 (m, 5H), 1.87-1.97 (m, 3H), 1.99-2.11 (m, 2H), 3.20-3.26 (m, 1H), 3.50-3.58 (m, 1H), 4.19 (s, 3H), 4.58 (d, 1H), 4.60 (d, 1H), 4.66 (dd, 1H), 4.79 (d, 1H), 4.95 (d, 1H), 5.14 (s, 1H), 5.34 (s, 1H), 7.23 (dd, 1H), 7.47 (dd, 1H), 7.57 (s, 1H), 7.65 (s, 2H), 7.74 (s, 1H).

ESI-MS m/z: 697 [M+1]⁺

Example 24

Synthesis of trans-2-(4-{(R)-1-[3-({[3,5-bis(trifluoromethyl)benzyl](2-methyl-2H-tetrazol-5-yl)amino}methyl)-6,7-difluoroquinolin-2-yl]pyrrolidin-2-yl}cyclohexyl)ethanol

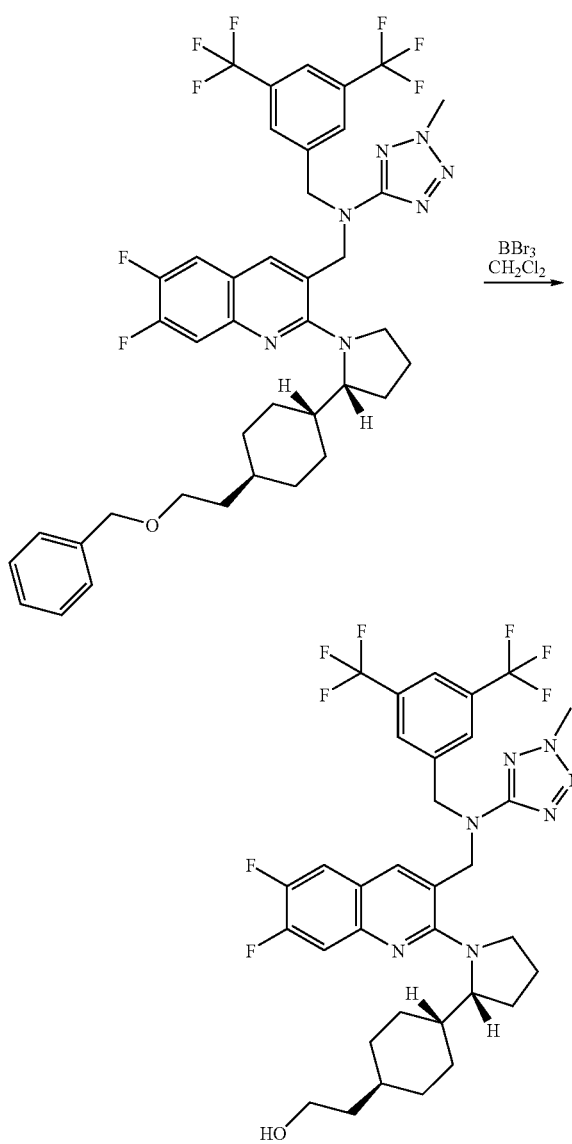

To a stirred solution of trans-N-[2-((R)-2-{4-[2-(benzyloxy)ethyl]cyclohexyl}pyrrolidin-1-yl)-6,7-difluoroquinolin-3-ylmethyl]-N-[3,5-bis(trifluoromethyl)benzyl](2-methyl-2H-tetrazol-5-yl)amine (11.0 g, 14.0 mmol) in CH₂Cl₂ (120 mL) is added dropwise BBr₃ (1.0 M CH₂Cl₂ solution, 18.0 mL, 18.0 mmol) at 0° C. and stirred at room temperature for 10 min. The reaction mixture is quenched by addition of sat. NaHCO₃ aq. extracted with ethyl acetate, and the organic layer is washed with brine, dried over magnesium sulfate, filtered and concentrated. The crude product is purified by silica gel column chromatography to give trans-2-(4-{(R)-1-[3-({[3,5-bis(trifluoromethyl)benzyl](2-methyl-2H-tetrazol-5-yl)amino}methyl)-6,7-difluoroquinolin-2-yl]pyrrolidin-2-yl}cyclohexyl)ethanol.

¹H-NMR (400 MHz, CDCl₃), δ (ppm): 0.72-0.93 (m, 2H), 1.01-1.18 (m, 3H), 1.26-1.36 (m, 1H), 1.39-1.44 (m, 2H), 1.47-1.55 (m, 1H), 1.63-1.77 (m, 6H), 1.83-1.90 (m, 1H), 1.97-2.05 (m, 1H), 3.18-3.24 (m, 1H), 3.48-3.55 (m, 1H), 3.62-3.67 (m, 2H), 4.21 (s, 3H), 4.24 (d, 1H), 4.56 (d, 1H), 4.61-4.67 (m, 1H), 4.79 (d, 1H), 4.99 (d, 1H), 7.22 (dd, 1H), 7.47 (dd, 1H), 7.56 (s, 1H), 7.63 (s, 2H), 7.73 (s, 1H).

ESI-MS m/z: 698 [M+1]⁺

Example 25

The following compounds are prepared from trans-N-(2-{(R)₂-[4-(2-benzyloxyethyl)cyclohexyl]pyrrolidin-1-yl}-substituted-quinolin-3-ylmethyl)-N—[substituted-benzyl](2-methyl-2H-tetrazol-5-yl)amine following the procedure of example 24.

| No. | Rn | R₇ | MS | ¹H-NMR (400 MHz, CDCl₃), δ(ppm) |
|---|---|---|---|---|
| 25-1 | 7-F | CF₃ | 680 [M + 1]⁺ | 0.72-0.93 (m, 2 H), 1.00-1.13 (m, 3 H), 1.25-1.35 (m, 1 H), 1.39-1.44 (m, 2 H), 1.50-1.54 (m, 1 H), 1.64-1.76 (m, 6 H), 1.84-1.90 (m, 1 H), 1.97-2.04 (m, 1 H), 3.21-3.27 (m, 1 H), 3.48-3.56 (m, 1 H), 3.62-3.67 (m, 2 H), 4.21 (s, 3 H), 4.56 (d, 1 H), 4.57 (d, 1 H), 4.66-4.71 (m, 1 H), 4.77 (d, 1 H), 4.98 (d, 1 H), 7.00 (ddd, 1 H), 7.36 (dd, 1 H), 7.46 (dd, 1 H), 7.52-7.64 (m, 3 H), 7.72 (s, 1 H). |

75
-continued

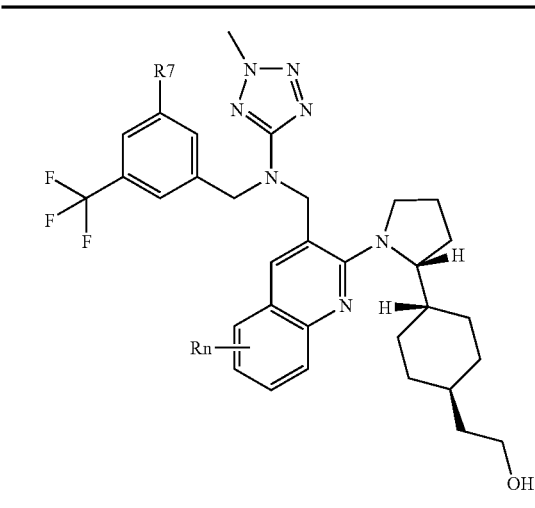

| No. | Rn | R<sub>7</sub> | MS | ¹H-NMR (400 MHz, CDCl₃), δ(ppm) |
|---|---|---|---|---|
| 25-2 | 7-F | Cl | 646 [M + 1]⁺ | 0.73-0.95 (m, 2 H), 1.00-1.14 (m, 3 H), 1.25-1.35 (m, 1 H), 1.39-1.45 (m, 2 H), 1.50-1.54 (m, 1 H), 1.64-1.76 (m, 6 H), 1.84-1.90 (m, 1 H), 1.97-2.04 (m, 1 H), 3.21-3.27 (m, 1 H), 3.49-3.57 (m, 1 H), 3.63-3.68 (dt, 2 H), 4.21 (s, 3 H), 4.45 (d, 1 H), 4.54 (d, 1 H), 4.65-4.73 (m, 1 H), 4.74 (d, 1 H), 4.95 (d, 1 H), 7.00 (ddd, 1 H), 7.31 (s, 1 H), 7.33 (s, 1 H), 7.37 (dd, 1 H), 7.44 (s, 1 H), 7.48 (dd, 1 H), 7.62 (s, 1 H). |
| 25-3 | 6,7-F₂ | Cl | 663 [M + 1]⁺ | 0.77-0.88 (m, 2 H), 1.01-1.10 (m, 2 H), 1.11-1.14 (m, 1 H), 1.25-1.36 (m, 1 H), 1.39-1.44 (m, 2 H), 1.65-1.78 (m, 6 H), 1.83-1.87 (m, 1 H), 1.97-2.03 (m, 1 H), 3.18-3.24 (m, 1 H), 3.46-3.55 (m, 1 H), 3.62-3.67 (m, 2 H), 4.21 (s, 3 H), 4.45 (d, 1 H), 4.51 (d, 1 H), 4.59-4.63 (m, 1 H), 4.76 (d, 1 H), 4.93 (d, 1 H), 7.20-7.23 (m, 1 H), 7.30 (s, 1 H), 7.32 (s, 1 H), 7.45-7.49 (m, 3 H), 7.56 (s, 1 H). |

76

Example 26

Synthesis of trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)acetoardehyde

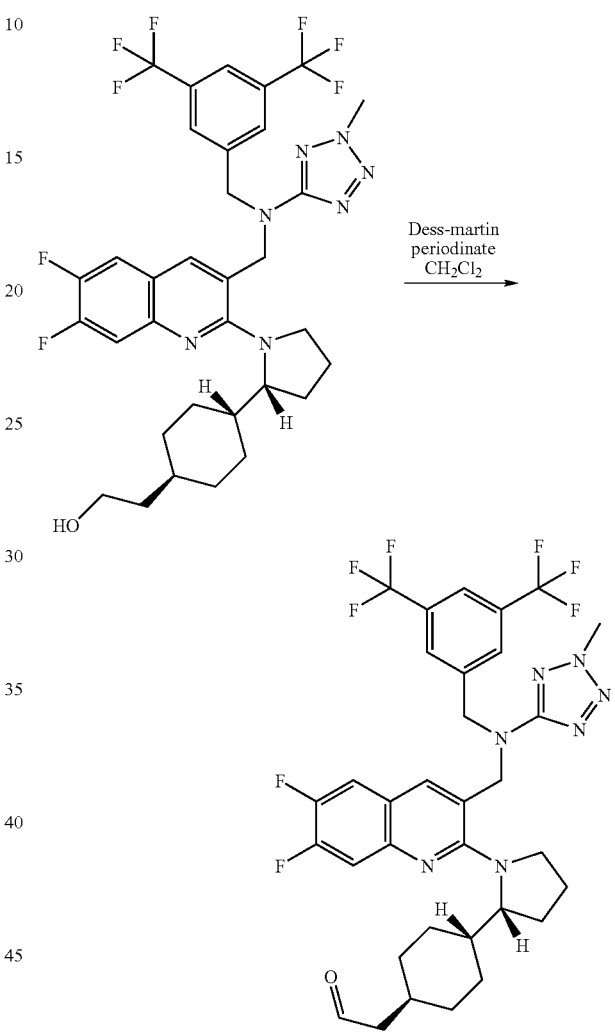

Dess-Martin periodinate (6.40 g, 15 mmol) is added to a suspension of trans-2-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)ethanol (8.80 g, 12.6 mmol) in CH₂Cl₂ (160 mL) at 0° C., and the resulting mixture is stirred at room temperature for 40 min. The reaction mixture is quenched by addition of sat. NaHCO₃ aq. and extracted with CH₂Cl₂ twice. The combined organic layer is washed with brine, dried over magnesium sulfate, filtered and concentrated. The crude product is purified by silica gel column chromatography to give trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)acetoardehyde ¹H-NMR (400 MHz, CDCl₃), δ (ppm): 0.80-1.01 (m, 2H), 1.04-1.16 (m, 2H), 1.55-1.83 (m, 8H), 1.85-1.93 (m, 1H), 1.98-2.04 (m, 1H), 2.24 (dd, 2H), 3.18-3.24 (m, 1H), 3.48-

3.56 (m, 1H), 4.21 (s, 3H), 4.54 (d, 1H), 4.57 (d, 1H), 4.63-4.69 (m, 1H), 4.79 (d, 1H), 4.98 (d, 1H), 7.22 (dd, 1H), 7.47 (dd, 1H), 7.56 (s, 1H), 7.63 (s, 2H), 7.73 (s, 1H), 9.72 (t, 1H). ESI-MS m/z: 696 [M+1]$^+$

Example 27

The following compounds are prepared from trans-(4-{(R)-1-[3-({N—[substituted-benzyl]-N-(2-methyl-2H-tetrazol-5-yl)amino}methyl)-substituted-quinolin-2-yl]pyrrolidin-2-yl}cyclohexyl)ethanol following the procedure of example 26.

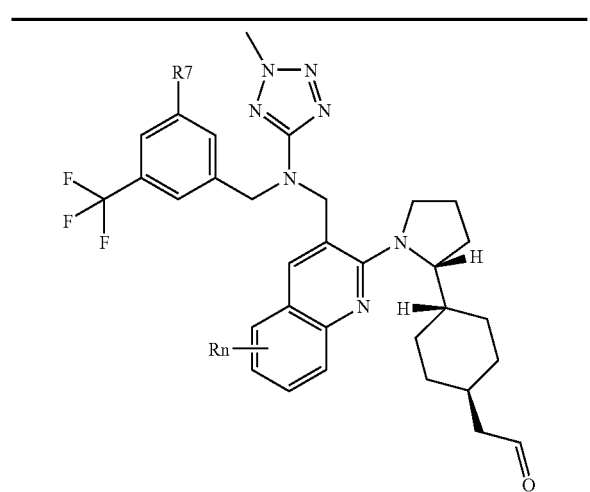

| No. | Rn | R$_7$ | MS | $^1$H-NMR (400 MHz, CDCl$_3$), δ(ppm) |
|---|---|---|---|---|
| 27-1 | 7-F | CF$_3$ | 678 [M + 1]$^+$ | 0.80-1.01 (m, 2 H), 1.04-1.16 (m, 2 H), 1.55-1.83 (m, 8 H), 1.85-1.93 (m, 1 H), 1.98-2.04 (m, 1 H), 2.24 (dd, 2 H), 3.21-3.27 (m, 1 H), 3.50-3.57 (m, 1 H), 4.20 (s, 3 H), 4.54-4.60 (m, 2 H), 4.66-4.73 (m, 1 H), 4.77 (d, 1 H), 4.97 (d, 1 H), 7.01 (ddd, 1 H), 7.36 (dd, 1 H), 7.46 (dd, 1 H), 7.60-7.64 (m, 3 H), 7.72 (s, 1 H), 9.72 (t, 1 H). |
| 27-2 | 7-F | Cl | 644 [M + 1]$^+$ | 0.81-1.04 (m, 2 H), 1.05-1.16 (m, 2 H), 1.55-1.82 (m, 8 H), 1.84-1.93 (m, 1 H), 1.96-2.04 (m, 1 H), 2.25 (dd, 2 H), 3.21-3.27 (m, 1 H), 3.50-3.57 (m, 1 H), 4.20 (s, 3 H), 4.45 (d, 1 H), 4.54 (d, 1 H), 4.67-4.72 (m, 1 H), 4.74 (d, 1 H), 4.95 (d, 1 H), 7.01 (ddd, 1 H), 7.30 (s, 1 H), 7.32 (s, 1 H), 7.36 (dd, 1 H), 7.44 (s, 1 H), 7.47 (dd, 1 H), 7.62 (s, 1 H), 9.73 (t, 1 H). |
| 27-3 | 6,7-F$_2$ | Cl | 661 [M + 1]$^+$ | 0.85-0.92 (m, 2 H), 1.03-1.12 (m, 2 H), 1.66-1.79 (m, 8 H), 1.85-1.90 (m, 1 H), 1.97-2.02 (m, 1 H), 2.22-2.25 (m, 2 H), 3.17-3.21 (m, 1 H), 3.47-3.55 (m, 1 H), 4.20 (s, 3 H), 4.45 (d, 1 H), 4.52 (d, 1 H), 4.61-4.65 (m, 1 H), 4.74 (d, 1 H), 4.95 (d, 1 H), 7.20-7.23 (m, 1 H), 7.30 (s, 1 H), 7.32 (s, 1 H), 7.44 (s, 1 H), 7.46 (dd, 1 H), 7.56 (s, 1 H). |

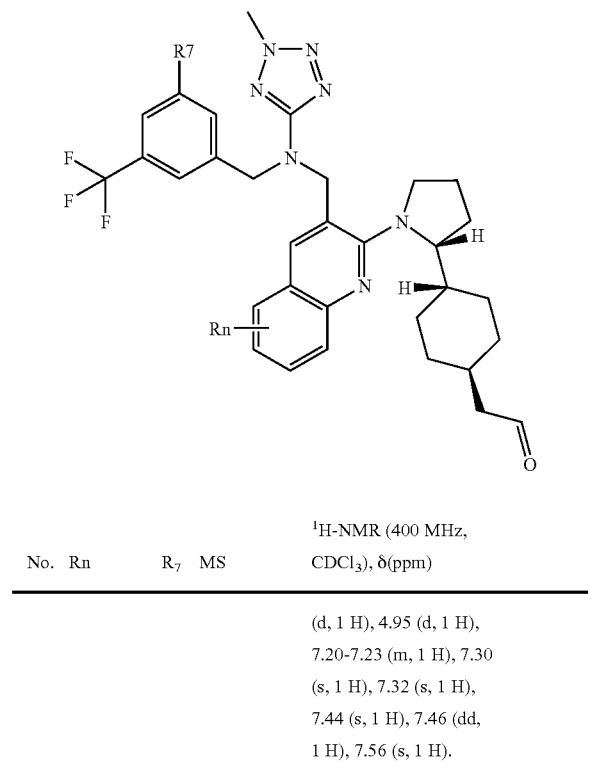

Example 28

Synthesis of trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)acetic acid

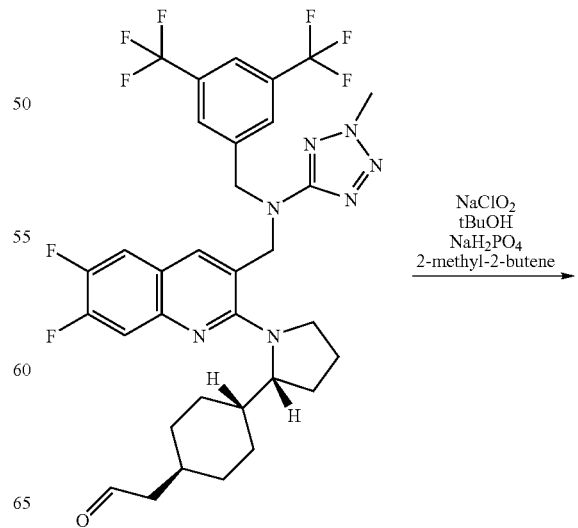

NaClO$_2$
tBuOH
NaH$_2$PO$_4$
2-methyl-2-butene
→

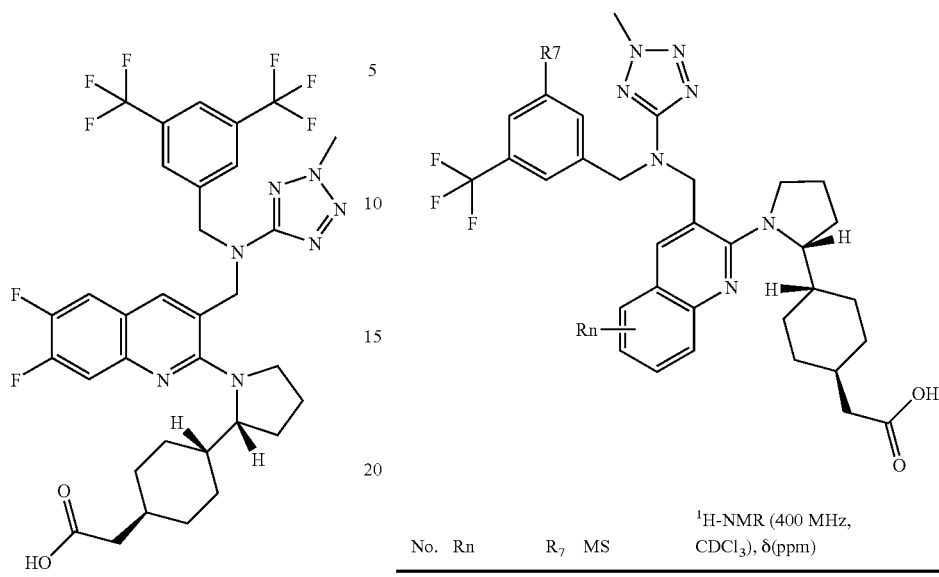

A mixture of NaClO$_2$ (4.60 g, 51 mmol) and NaH$_2$PO$_4$ (4.30 g, 36 mmol) in water (20 mL) is added dropwise to a solution of trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)acetoardehyde (7.10 g, 10.2 mmol) in 2-methyl-2-butene (15 mL)/t-BuOH (115 mL) at room temperature, and the resulting mixture is stirred at room temperature for 1 hour. The reaction mixture is quenched by addition of sat. NH$_4$Cl aq. at 0° C. and extracted with ethyl acetate. The organic layer is washed with brine, dried over magnesium sulfate, filtered concentrated. The crude product is purified by silica gel column chromatography to give trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)acetic acid.

$^1$H-NMR (400 MHz, CDCl$_3$), δ (ppm): 0.78-1.00 (m, 2H), 1.03-1.17 (m, 2H), 1.60-1.80 (m, 8H), 1.83-1.93 (m, 1H), 1.96-2.06 (m, 1H), 2.17 (d, 2H), 3.15-3.24 (m, 1H), 3.46-3.54 (m, 1H), 4.20 (s, 3H), 4.54 (d, 1H), 4.57 (d, 1H), 4.60-4.68 (m, 1H), 4.79 (d, 1H), 4.98 (d, 1H), 7.22 (dd, 1H), 7.47 (dd, 1H), 7.56 (s, 1H), 7.63 (s, 2H), 7.72 (s, 1H).

ESI-MS m/z: 712 [M+1]$^+$

Example 29

The following compounds are prepared from trans-(4-{(R)-1-[3-({N—[substituted-benzyl]-N-(2-methyl-2H-tetrazol-5-yl)amino}methyl)-substituted-quinolin-2-yl]pyrrolidin-2-yl}cyclohexyl)acetoardehyde following the procedure of example 28.

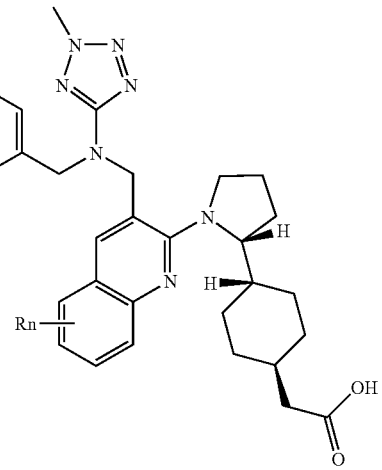

| No. | Rn | R$_7$ | MS | $^1$H-NMR (400 MHz, CDCl$_3$), δ(ppm) |
|---|---|---|---|---|
| 29-1 | 7-F | CF$_3$ | 694 [M + 1]$^+$ | 0.80-1.02 (m, 2 H), 1.04-1.17 (m, 2 H), 1.50-1.82 (m, 8 H), 1.83-1.93 (m, 1 H), 1.95-2.05 (m, 1 H), 2.17 (d, 2 H), 3.21-3.28 (m, 1 H), 3.49-3.57 (m, 1 H), 4.20 (s, 3 H), 4.45 (d, 1 H), 4.54 (d, 1 H), 4.65-4.72 (m, 1 H), 4.73 (d, 1 H), 4.95 (d, 1 H), 7.00 (ddd, 1 H), 7.31 (s, 1 H), 7.32 (s, 1 H), 7.36 (dd, 1 H), 7.43 (s, 1 H), 7.47 (dd, 1 H), 7.63 (s. 1 H). |
| 29-2 | 7-F | Cl | 660 [M + 1]$^+$ | 0.80-1.00 (m, 2 H), 1.04-1.15 (m, 2 H), 1.50-1.80 (m, 8 H), 1.83-1.92 (m, 1 H), 1.95-2.04 (m, 1 H), 2.17 (d, 2 H), 3.21-3.27 (m, 1 H), 3.49-3.57 (m, 1 H), 4.20 (s, 3 H), 4.57 (d, 2 H), 4.65-4.72 (m, 1 H), 4.77 (d, 1 H), 4.97 (d, 1 H), 7.00 (ddd, 1 H), 7.36 (dd, 1 H), 7.47 (dd, 1 H), 7.62 (s. 3 H), 7.71 (s, 1 H). |
| 29-3 | 6,7-F$_2$ | Cl | 679 [M + 1]$^+$ | 0.83-0.96 (m, 2 H), 1.04-1.10 (m, 2 H), 1.52-1.78 (m, 8 H), 1.85-1.88 (m, 1 H), 1.97-2.03 (m, 1 H), 2.17 (d, 2 H), 3.18-3.22 (m, 1 H), 3.47-3.55 (m, 1 H), 4.20 (s, 3 H), 4.45 (d, 1 H), 4.48 (d, 1 H), 4.65-4.70 (m, 1 H), 4.74 (d, 1 H), 4.95 (d, 1 H), 7.22 (dd, 1 H), 7.30 (s, 1 H), 7.32 (s, 1 H), 7.44 (s, 1 H), 7.47 (dd, 1 H), 7.56 (s, 1 H). |

Example 30

Synthesis of give trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)acetic acid amide

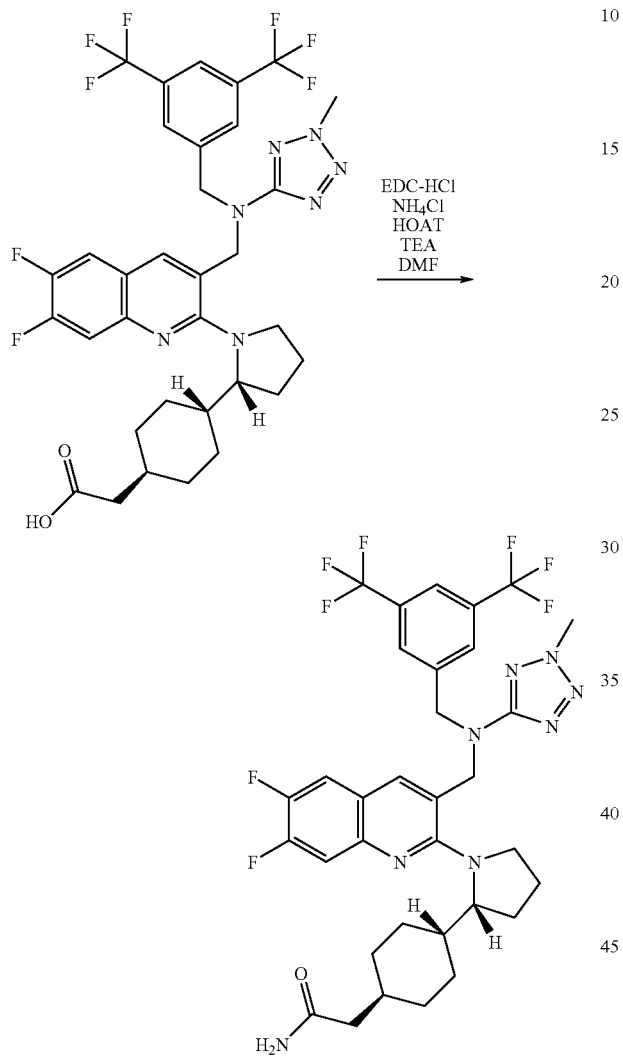

To a solution of trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)acetic acid (85 mg, 0.12 mmol) in DMF (3 mL) is added NH₄Cl (10 mg, 0.18 mmol), N-ethyl-N'-(3-dimethylaminopropyl)carbodiimide hydrochloride (EDC.HCl 41 mg, 0.18 mmol), 1-hydroxy-7-azabenzotriazole (HOAt, 24 mg, 0.18 mmol), and small amount of triethylamine. After stirring for 2 hours at room temperature, the reaction mixture is diluted with EtOAc, washed successively with water and brine, and dried over magnesium sulfate. Evaporation of the solvent and purification by silica gel column using ethyl acetate-hexane affords trans-(4-{(R)-1-[3-({N-[3,5-bis(trifluoromethyl)benzyl]-N-(2-methyl-2H-tetrazol-5-yl)amino}methyl)-6,7-difluoroquinolin-2-yl]pyrrolidin-2-yl}cyclohexyl)acetic acid amide.

¹H-NMR (400 MHz, CDCl₃), δ (ppm): 0.79-0.98 (m, 2H), 1.05-1.14 (m, 2H), 1.47-1.81 (m, 8H), 1.87-1.93 (m, 1H), 2.02-2.07 (m, 3H), 3.19-3.27 (m, 1H), 3.50-3.59 (m, 1H), 4.20 (s, 3H), 4.55 (d, 2H), 4.57-4.68 (m, 1H), 4.78 (d, 1H), 4.97 (d, 1H), 5.30 (bs, 2H), 7.20-7.24 (m, 2H), 7.35-7.40 (m, 1H), 7.63 (s, 2H), 7.73 (s, 1H).

ESI-MS m/z: 710 [M+1]⁺

Example 31

Synthesis of N-[(3-{N'-[3,5-bis(trifluoromethyl)benzyl]-N'-(2-methyl-2H-tetrazol-5-yl)amino}methyl)quinoxalin-2-yl]-N-(cyclopentylmethyl)ethylamine

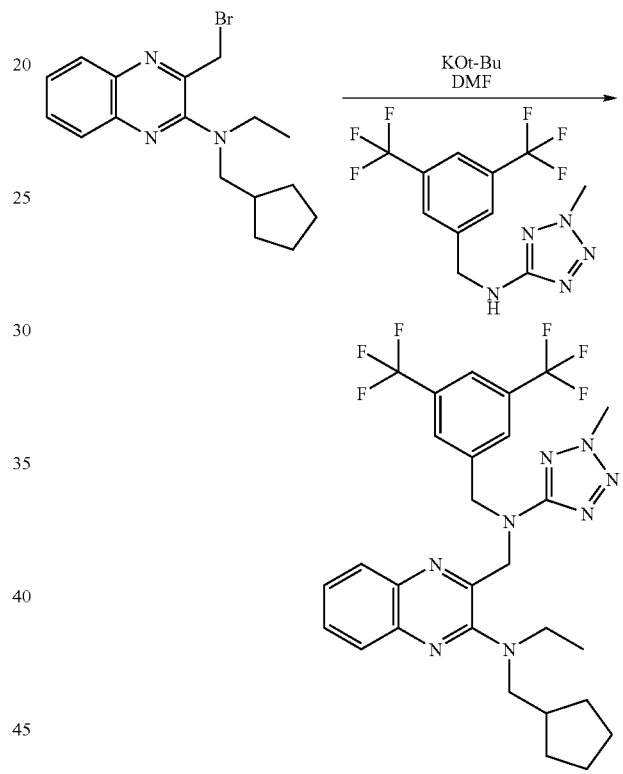

Potassium tert-butoxide (11 mg, 0.098 mmol) is added to a solution of N-[3,5-bis(trifluoromethyl)benzyl]-N-(2-methyl-2H-tetrazol-5-yl)amine (46 mg, 0.14 mmol) in DMF (1 mL) at 5° C. and the mixture is stirred at the same temperature for 20 min. To the mixture, a DMF (1 mL) solution of N-[3-(bromomethyl)quinoxalin-2-yl]-N-(cyclopentylmethyl)ethylamine (38 mg, 0.11 mmol) is added dropwise over 3 min and the mixture is further stirred for 30 min. After adding 1N HCl aq, the mixture is extracted with ethyl acetate. The combined organic layer is washed with brine, dried over magnesium sulfate, filtrated, and concentrated. The resulting mixture is purified by silica gel column chromatography to give N-[(3-{N'-[3,5-bis(trifluoromethyl)benzyl]-N'-(2-methyl-2H-tetrazol-5-yl)amino}methyl)quinoxalin-2-yl]-N-(cyclopentylmethyl)ethylamine.

¹H-NMR (400 MHz, CDCl₃), δ (ppm): 1.03-1.10 (m, 2H), 1.14 (t, 3H), 1.37-1.68 (m, 6H), 2.11-2.21 (m, 1H), 3.31 (q, 2H), 3.31 (d, 2H), 4.13 (s, 3H), 4.93 (s, 4H), 7.45 (ddd, 1H), 7.57 (ddd, 1H), 7.71 (s, 1H), 7.77 (s, 2H), 7.75-7.80 (m, 2H).

ESI-MS m/z: 593 [M+1]⁺

Example 32

Synthesis of N-(6-{N'-[3,5-bis(trifluoromethyl)benzyl-N'-(2-methyl-2H-tetrazol-5-yl)amino]methyl}-1-methyl-1H-pyrrolo[3,2-b]pyridin-5-yl)-N-(cyclopentylmethyl)ethylamine

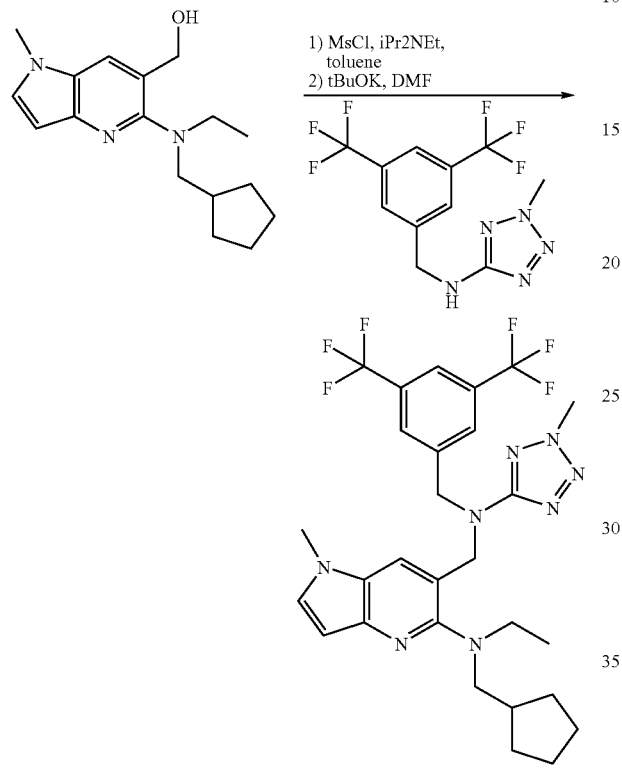

To a solution of {5-[N-(cyclopentylmethyl)-N-ethylamino]-1-methyl-1H-pyrrolo[3,2-b]pyridin-6-yl}methanol (85 mg, 0.30 mmol) in toluene (1.5 mL) is added diisopropylethylamine (0.062 mL, 0.35 mmol) and methanesulfonyl chloride (0.027 mL, 0.35 mmol) at room temperature. After stirring for 1 hour, H$_2$O is added. The mixture is extracted with EtOAc, washed with brine, dried over sodium sulfate and concentrated in vacuo. To a solution of N-[3,5-bis(trifluoromethyl)benzyl]-N-(2-methyl-2H-tetrazol-5-yl)amine (106 mg, 0.33 mmol) in DMF (1.5 mL) is added potassium tert-butoxide (54 mg, 0.44 mmol) at 0° C. After stirring for 30 min, a solution of the residue in DMF (1 mL) is slowly added and the reaction mixture is stirred for 1 hour. The reaction mixture is quenched with H$_2$O, and the mixture is extracted with EtOAc. The organic layer is washed with brine, dried over sodium sulfate, concentrated and purified by silica-gel column chromatography to give N-(6-{N'-[3,5-bis(trifluoromethyl)benzyl-N'-(2-methyl-2H-tetrazol-5-yl)amino]methyl}-1-methyl-1H-pyrrolo[3,2-b]pyridin-5-yl)-N-(cyclopentylmethyl)ethylamine as a colorless oil.

$^1$H-NMR (400 MHz, CDCl$_3$), δ (ppm): 0.96-1.12 (m, 5H), 1.34-1.58 (m, 6H), 1.94-2.13 (m, 1H), 2.95-3.15 (m, 2H), 3.65-3.80 (m, 4H), 4.13-4.23 (m, 4H), 4.71 (s, 2H), 4.85-5.00 (m, 2H), 6.60 (s, 1H), 7.20 (s, 1H), 7.41 (s, 1H), 7.68 (s, 2H), 7.75 (s, 1H).

ESI-MS m/z: 595 [M+1]$^+$

Example 33

N-(6-{N'-[3,5-bis(trifluoromethyl)benzyl]-N'-(2-methyl-2H-tetrazol-5-yl)amino}methyl-1,3-dimethyl-1H-pyrrolo[3,2-b]pyridin-5-yl)-N-(cyclopentylmethyl)ethylamine is prepared from {5-[N-(cyclopentylmethyl)ethylamino]-1,3-dimethyl-1H-pyrrolo[3,2-b]pyridin-6-yl}methanol and N-[3,5-bis(trifluoromethyl)benzyl]-N-(2-methyl-2H-tetrazol-5-yl)amine following the procedure of example 32.

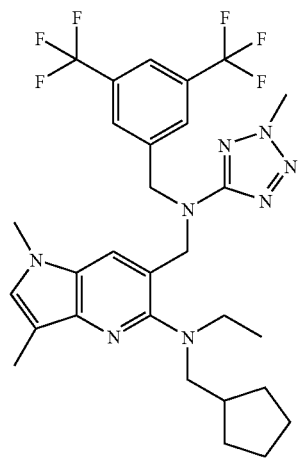

$^1$H-NMR (400 MHz, CDCl$_3$), δ (ppm): 0.99 (t, 3H), 1.03-1.12 (m, 2H), 1.34-1.56 (m, 6H), 1.94-2.08 (m, 1H), 2.32 (s, 3H), 3.00-3.09 (m, 4H), 3.59 (s, 3H), 4.20 (s, 3H), 4.66 (s, 2H), 4.94 (s, 2H), 6.93 (d, 1H), 7.33 (s, 1H), 7.67 (s, 2H), 7.72 (s, 1H).

ESI-MS m/z: 609 [M+1]$^+$

Example 34

Inhibitory Activity of Compounds

| Example | IC50 μM (buffer) | IC50 μM (human plasma) |
| --- | --- | --- |
| 1 | 0.16 | 0.26 |
| 2-6 | 0.028 | 0.092 |
| 2-7 | 0.044 | 0.075 |
| 2-8 | 0.04 | 0.024 |
| 2-10 | 0.036 | 0.037 |
| 2-12 | 0.12 | 0.094 |
| 2-13 | 0.032 | 0.082 |
| 2-15 | 0.043 | 0.062 |
| 2-17 | 0.25 | 0.22 |
| 2-22 | 0.16 | 0.03 |
| 3-2 | 0.039 | 0.043 |
| 3-4 | 0.06 | 0.062 |
| 3-5 | 0.12 | 0.11 |
| 6 | 0.054 | 0.039 |
| 13-4 | 0.0058 | 0.033 |
| 21 | 0.021 | 0.045 |
| 28 | 0.025 | 0.039 |

The starting material can be prepared, for example, as follows:

Example A

Preparation of {2-[N-(cyclopentylmethyl)-N-ethylamino]quinolin-3-yl}methanol

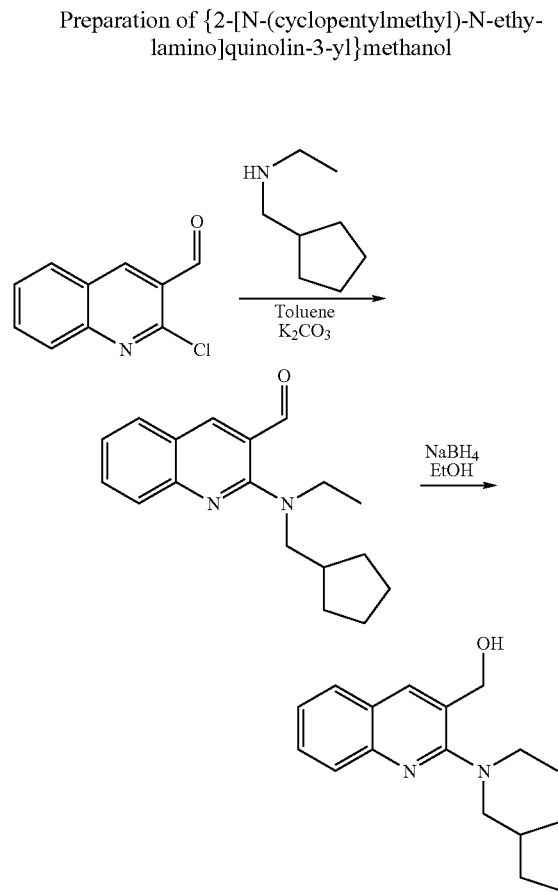

Step 1:

A suspension of 2-chloroquinoline-3-carbaldehyde (50 mg, 0.26 mmol), N-(cyclopenthyl-methyl)-N-ethylamine (50 mg, 0.39 mmol) and potassium carbonate (54 mg, 0.39 mmol) in toluene is irradiated in a microwave reactor for 30 min. The reaction mixture is purified by silica gel column chromatography to give 2-[N-(cyclopentylmethyl)-N-ethylamino] quinoline-3-carbaldehyde.

$^1$H-NMR (400 MHz, CDCl$_3$), δ (ppm): 1.11-1.23 (m, 2H), 1.21 (t, 3H), 1.45-1.60 (m, 4H), 1.65-1.74 (m, 2H), 2.34 (m, 1H), 3.48 (d, 2H), 3.53 (q, 2H), 7.32 (ddd, 1H), 7.66 (ddd, 1H), 7.76 (dd, 1H), 7.79 (dd, 1H), 8.45 (s, 1H), 10.15 (s, 1H).

Step 2:

To a solution of 2-[N-(cyclopentylmethyl)-N-ethylamino] quinoline-3-carbaldehyde (25 mg, 0.088 mmol) in ethanol (1 mL) is added sodium borohydride (5 mg, 0.13 mmol) and the mixture is stirred for 1 hour. After addition of sat. ammonium chloride and water, the mixture is extracted with ethyl acetate. The combined organic layer is washed with brine, dried over magnesium sulfate, filtered and concentrated to give {2-[N-(cyclopentylmethyl)-N-ethylamino]quinolin-3-yl}methanol, which is used without further purification.

Example B

Preparation of {2-[N-(cyclohexylmethyl)-N-ethylamino]-7-fluoroquinolin-3-yl}methanol

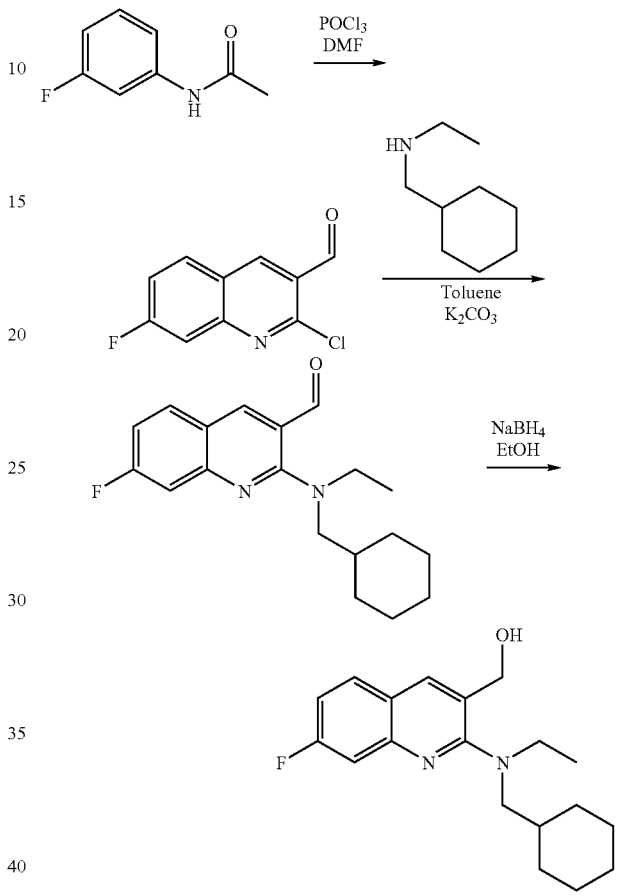

Step 1:

A Vilsmeier reagent prepared from DMF (23 mL) and phosphoryl chloride (78.4 mL) at 0-10° C. is slowly added dropwise to 3-fluoroacetanilide (18.5 g, 0.12 mol) and the resulting mixture is stirred at 100° C. for 14 hours. The mixture is poured onto ice-water and extracted with CH$_2$Cl$_2$ twice. The combined organic layer is dried, filtered and concentrated. The crystal is collected and washed with CH$_2$Cl$_2$ to give 2-chloro-7-fluoroquinoline-3-carbaldehyde as a brown powder.

$^1$H-NMR (400 MHz, CDCl$_3$), δ (ppm): 7.45 (ddd, 1H), 7.72 (dd, 1H), 8.01 (dd, 1H), 8.76 (s, 1H), 10.55 (s, 1H).

Step 2:

A suspension of 2-chloro-7-fluoroquinoline-3-carbaldehyde (200 mg, 0.95 mmol), N-(cyclohexylmethyl)-N-ethylamine (140 mg, 0.99 mmol) and potassium carbonate (140 mg, 1.0 mmol) in toluene (3 mL) is stirred and refluxed for 14 hours. The reaction mixture is cooled to room temperature and then diluted with water and ethyl acetate. The organic layer is washed with 1N HCl, brine, dried over magnesium sulfate, filtered and concentrated. The crude product is purified by silica gel column chromatography to give 2-[N-(cyclohexylmethyl)-N-ethylamino]-7-fluoroquinoline-3-carbaldehyde.

¹H-NMR (400 MHz, CDCl₃), δ (ppm): 0.83-0.93 (m, 2H), 1.08-1.20 (m, 4H), 1.22 (t, 3H), 1.62-1.81 (m, 5H), 3.40 (d, 2H), 3.52 (q, 2H), 7.08 (ddd, 1H), 7.38 (dd, 1H), 7.73 (dd, 1H), 8.40 (s, 1H), 10.09 (s, 1H).

Step 3:

To a mixture of 2-[N-(cyclohexylmethyl)-N-ethylamino]-7-fluoroquinoline-3-carbaldehyde (230 mg, 0.73 mmol) in ethanol (2 mL) is added sodium borohydride (30 mg, 0.79 mmol) and the mixture is stirred for 2 hours. After addition of sat. ammonium chloride and water, the mixture is extracted with ethyl acetate. The combined organic layer is washed with brine, dried over magnesium sulfate, filtered and concentrated to give [N-(cyclopentylmethyl)-N-ethylamino]quinolin-3-yl}methanol, which is used without further purification.

¹H-NMR (400 MHz, CDCl₃), δ (ppm): 0.85-0.95 (m, 2H), 1.10-1.20 (m, 3H), 1.15 (t, 3H), 1.56-1.71 (m, 4H), 1.73-1.79 (m, 4H), 3.21 (d, 2H), 3.28 (q, 2H), 3.48 (brs, 1H), 4.82 (s, 2H), 7.14 (ddd, 1H), 7.48 (dd, 1H), 7.67 (dd, 1H), 7.98 (s, 1H).

Example C

Preparation of {2-[N-(cyclopentylmethyl)-N-ethylamino]-6,7-difluoroquinolin-3-yl}methanol

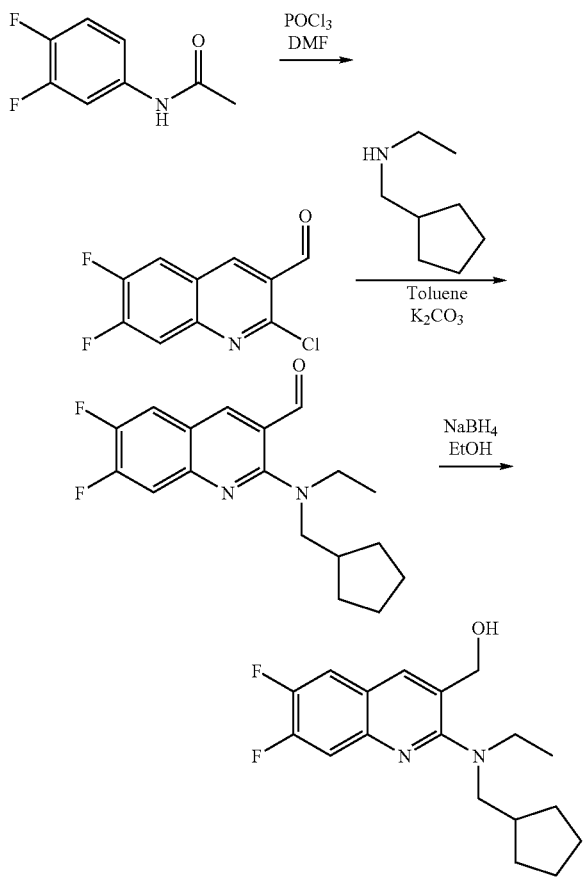

Step 1:

Phosphoryl chloride (147.1 mL) is carefully added to DMF (32.5 mL) at 0-15° C. to prepare a solution of vilsmeier reagent in phosphoryl chloride, and the mixture is warmed to 30° C. to give clear pale yellow mixture. 3,4-difluoroacetanilide (30 g, 0.12 mol) is added to the mixture, and the resulting mixture is stirred at 80° C. for 30 min, 90° C. for 30 min, 100° C. for 18 hours, and finally 120° C. for 2 hours. The mixture is cooled to room temperature, poured onto ice-water (1500 mL) and extracted with CH₂Cl₂ 7 times (total 3000 mL). The combined organic layer is dried over magnesium sulfate, filtered and concentrated. The brown crystal is collected and washed with CH₂Cl₂ to give 2-chloro-6,7-difluoroquinoline-3-carbaldehyde as a pale yellow powder.

¹H-NMR (400 MHz, CDCl₃), δ (ppm): 7.73 (dd, 1H), 7.84 (dd, 1H), 8.69 (s, 1H), 10.55 (s, 1H).

Step 2:

A suspension of 2-chloro-6,7-difluoroquinoline-3-carbaldehyde (0.13 g, 0.56 mmol), N-(cyclopenthylmethyl)-N-ethylamine (0.15 g, 1.2 mmol), and potassium carbonate (0.15 g, 1.1 mmol) in toluene (2.0 mL) is stirred and refluxed for 15 hours. The reaction mixture is purified by silica gel column chromatography to give 2-[N-(cyclopentylmethyl)-N-ethylamino]-6,7-difluoroquinoline-3-carbaldehyde.

¹H-NMR (400 MHz, CDCl₃), δ (ppm): 1.11-1.23 (m, 2H), 1.23 (t, 3H), 1.47-1.63 (m, 4H), 1.67-1.76 (m, 2H), 2.33 (sep, 1H), 3.47 (d, 2H), 3.54 (q, 2H), 7.49 (dd, 1H), 7.63 (dd, 1H), 8.36 (s, 1H), 10.12 (s, 1H).

Step 3:

To a mixture of 2-[N-(cyclopentylmethyl)-N-ethylamino]-6,7-difluoroquinoline-3-carbaldehyde (0.10 g, 0.31 mmol) in ethanol (2.0 mL) is added sodium borohydride (14 mg, 0.37 mmol) and the mixture is stirred for 2 hours. After addition of sat. ammonium chloride and water, the mixture is extracted with ethyl acetate. The combined organic layer is washed with brine, dried over magnesium sulfate, filtered and concentrated to {2-[N-(cyclopentylmethyl)-N-ethylamino]-6,7-difluoroquinolin-3-yl}methanol which is used without further purification.

¹H-NMR (400 MHz, CDCl₃), δ (ppm): 1.11-1.20 (m, 2H), 1.17 (t, 3H), 1.48-1.63 (m, 4H), 1.67-1.76 (m, 2H), 2.13 (sep, 1H), 3.23-3.28 (m, 4H), 3.85 (brs, 1H), 4.83 (brs, 2H), 7.43 (dd, 1H), 7.62 (dd, 1H), 7.91 (s, 1H).

Example D

Preparation of ethyl trans-[4-({N-ethyl-N-[3-(hydroxymethyl)quinolin-2-yl]amino}methyl)cyclohexyl]acetate

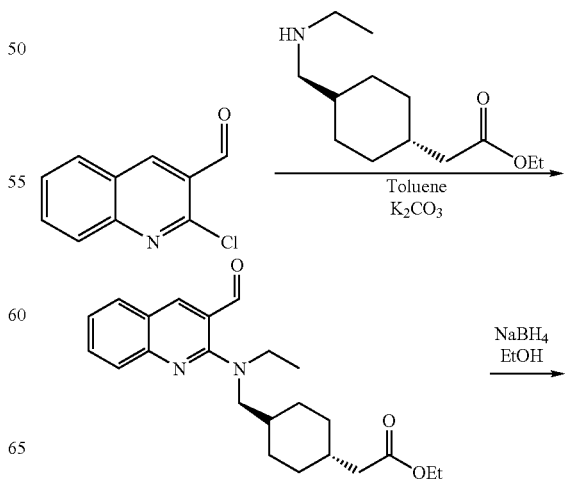

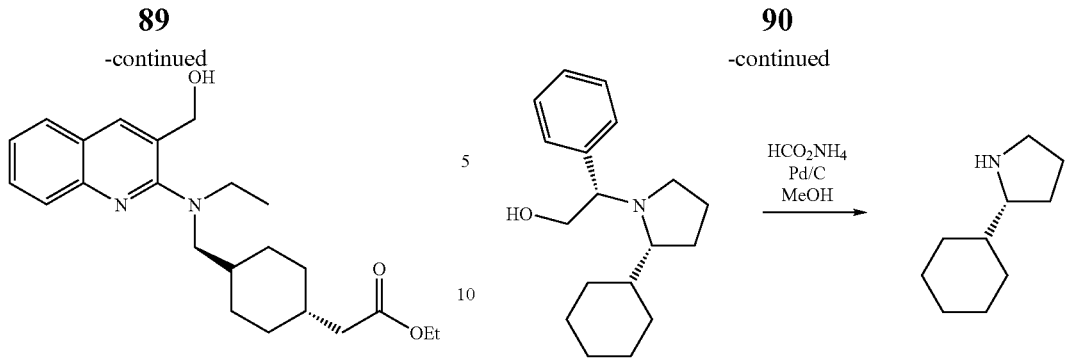

A suspension of 2-chloroquinoline-3-carbaldehyde (93 mg, 0.49 mmol), ethyl trans-{4-[(N-ethylamino)methyl]cyclohexyl}acetate (165 mg, 0.73 mmol) and potassium carbonate (134 mg, 0.97 mmol) in toluene (2 mL) is stirred and refluxed for 3 days. The reaction mixture is cooled to room temperature, diluted with water and ethyl acetate. The organic layer is washed with brine, dried over magnesium sulfate, filtered and concentrated. The crude residue is dissolved with ethanol (1.5 mL) and treated with sodium borohydride (18 mg, 0.48 mmol). The mixture is stirred at room temperature for 2 hours. After addition of sat. ammonium chloride and water, the mixture is extracted with ethyl acetate. The combined organic layer is washed with brine, dried over magnesium sulfate, filtered and concentrated. The crude product is purified by silica gel column chromatography to give ethyl trans-[4-({N-ethyl-N-[3-(hydroxymethyl)quinolin-2-yl]amino}methyl)cyclohexyl]acetate.

$^1$H-NMR (400 MHz, CDCl$_3$), δ (ppm): 0.86-1.02 (m, 4H), 1.14 (t, 3H), 1.22 (t, 3H), 1.48-1.53 (m, 1H), 1.65-1.87 (m, 5H), 2.13 (d, 2H), 3.21 (d, 2H), 3.25 (q, 2H), 3.87 (brs, 1H), 4.85 (s, 2H), 7.39 (ddd, 1H), 7.60 (ddd, 1H), 7.71 (dd, 1H), 7.87 (d, 1H), 7.99 (s, 1H).

Example E

Preparation of (R)-2-cyclohexylpyrrolidine (R)-2-cyclohexylpyrrolidine is prepared using the same procedures for (S)-2-cyclopentylpyrrolidine ((S)-(+)-phenylglycinol is used instead of (R)-(−)-phenylglycinol, see *J. Org. Chem.*, 1992, 57, 1656-1662) as shown below.

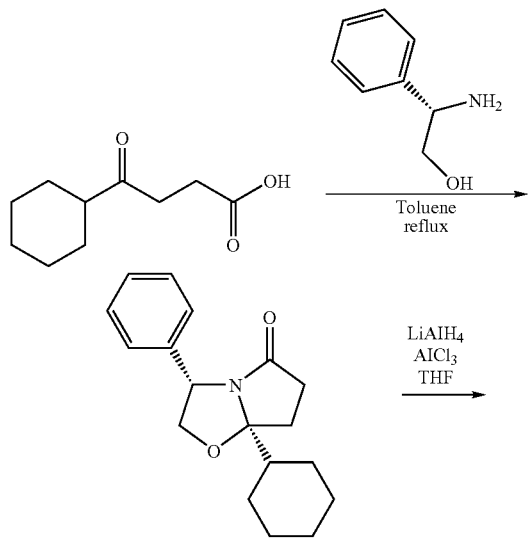

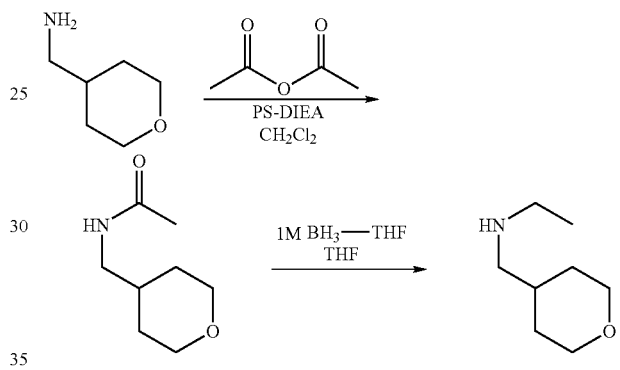

Example F

Preparation of ethyl[(tetrahydropyran-4-yl)methyl)]amine

Step 1:
PS-DIEA (Argonaut Technologies, 1.35 g, 4.5 mmol) is added to a mixture of C-(tetrahydropyran-4-yl)methylamine (345 mg, 3.0 mmol) in CH$_2$Cl$_2$ (20 ml) at ambient temperature. Acetic anhydride (367 mg, 3.6 mmol) is added to the mixture. After stirring at ambient temperature for 18 hours, methylisocyanate polystyrene (Novabiochem, 1.84 g, 3.0 mmol) and N-(2-aminoethyl)aminomethyl polystyrene (Novabiochem, 1.07 g, 3.0 mmol) are added. After stirring at room temperature for 4 h, the resins are removed by filtration, and the resins are washed with dichloromethane. The filtrate and washing are combined, and the solvent is removed by evaporation in vacuo to give N-(tetrahydropyran-4-ylmethyl)acetamide.
ESI-MS m/z: 158 [M+1]$^+$
UPLC retention time: 0.94 min.

Step 2:
1M Borane THF complex solution in THF (10.2 ml, 10.2 mmol) is added to a solution of N-(tetrahydropyran-4-ylmethyl)acetamide (235 mg, 1.50 mmol) in THF (15 ml) at ambient temperature under nitrogen gas atmosphere. After stirring for 2 days, methanol (5 ml) is added to the reaction mixture at ambient temperature. After stirring for 1 hour, 1N HCl (50 ml) is added to the mixture, and a part of THF is removed by evaporation in vacuo. The mixture is washed with ether and 5 N NaOH is added to the mixture. The product is extracted with CH$_2$Cl$_2$, and the organic phase is washed with brine, dried over magnesium sulfate, and concentrated to give N-ethyl-N—[(tetrahydropyran-4-yl)methyl)]amine.
ESI-MS m/z: 144 [M+1]$^+$
HPLC retention time: 0.58 min.

Example G

Preparation of N-[3,5-bis(trifluoromethyl)benzyl]-N-(2-methyl-2H-tetrazol-5-yl)amine <Method 1>

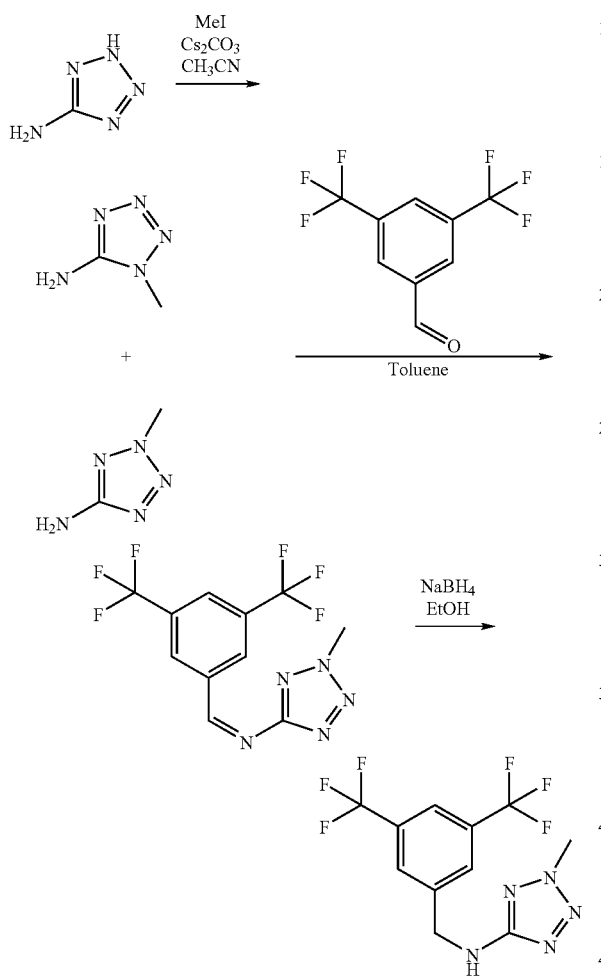

Step 1:

Methyliodide (45 mL, 1.2 eq., 0.72 mol) is added to a mixture of 5-aminotetrazole (51.1 g, 0.60 mol) and $Cs_2CO_3$ (235.0 g, 1.2 eq., 0.72 mol) in acetonitrile (500 mL), and the resulting mixture is stirred at 50° C. for 18 hours. The mixture (at 50° C.) is filtered, and the residue is washed with hot acetnitrile (50° C.). The filtrate is concentrated to give the mixture of desired 5-amino-2-methyltetrazole and 5-amino-1-methyltetrazole.

Step 2:

A crude mixture of 5-amino-2-methyltetrazole and 5-amino-1-methyltetrazole is treated with 3,5-bis(trifluoromethyl)benzaldehyde (48 mL, 71 g, 0.29 mol) in toluene (780 mL), and the mixture is stirred and refluxed for 5 hours. The resulting mixture is filtered to remove off the insoluble solid (5-amino-1-methyltetrazole), and the residue is washed with hot toluene. The filtrate is concentrated to give crude 2-methyl-N-[3,5-bis(trifluoromethyl)phenylmethylene]-2H-tetrazole-5-amine (70.1 g).

Step 3:

$NaBH_4$ (8.2 g, 0.22 mol) is added portionwise slowly to EtOH (700 mL) solution of crude 2-methyl-N-[3,5-bis(trifluoromethyl)phenylmethylene]-2H-tetrazole-5-amine at 0° C., and the mixture is stirred at room temperature for 1 hour. After addition of sat. $NH_4Cl$ aq. and water at 0° C., the mixture is concentrated to remove 300 mL of EtOH and extracted with $CH_2Cl_2$ (300 mL×4 times). The combined organic layer is washed with brine, dried over magnesium sulfate, filtered and concentrated The residue is purified by silica gel column chromatography to give N-[3,5-bis(trifluoromethyl)benzyl]-N-(2-methyl-2H-tetrazol-5-yl)amine as a white crystalline solid.

$^1$H-NMR (400 MHz, $CDCl_3$), δ (ppm): 1.61 (s, 3H), 4.66 (d, 2H), 5.03 (t, 1H), 7.79 (s, 1H), 7.83 (s, 1H).

<Method 2>

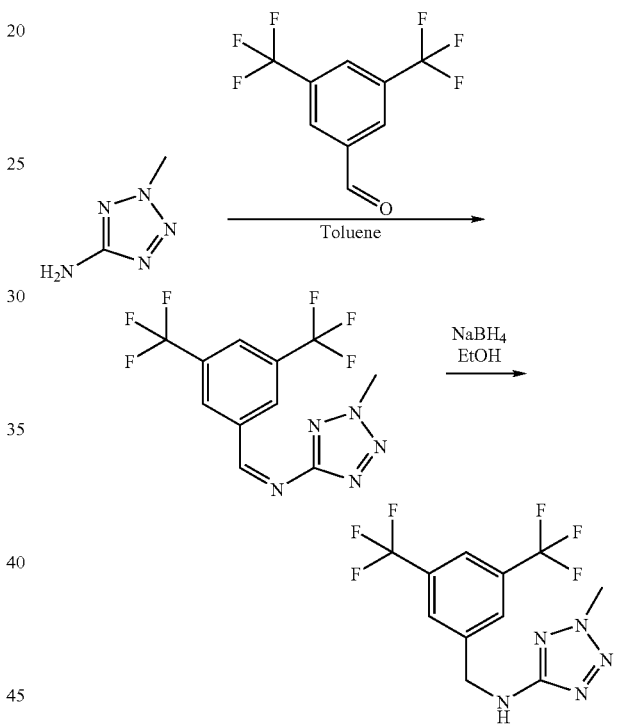

Step 1:

A mixture 5-amino-2-methyltetrazole (5.00 g, 50 mmol) and 3,5-bis(trifluoromethyl)benzaldehyde (19.5 g, 81 mmol) in toluene (100 mL) is stirred and refluxed for 3 hours. The resulting mixture is concentrated to give crude 2-methyl-N-[3,5-bis(trifluoromethyl)phenylmethylene]-2H-tetrazole-5-amine.

Step 2:

$NaBH_4$ (1.2 g, 64 mmol) is added portionwise slowly to an EtOH (100 mL) solution of crude 2-methyl-N-[3,5-bis(trifluoromethyl)phenylmethylene]-2H-tetrazole-5-amine at 0° C., and the mixture is stirred at room temperature for 1 hour. After addition of sat. $NH_4Cl$ aq. and water at 0° C., the mixture is extracted with EtOAc. The combined organic layer is washed with brine, dried over magnesium sulfate, filtered and concentrated The residue is purified by silica gel column chromatography chromatography to give N-[3,5-bis(trifluoromethyl)benzyl]-N-(2-methyl-2H-tetrazol-5-yl)amine as a white crystalline solid.

$^1$H-NMR (400 MHz, CDCl$_3$), δ (ppm): 1.61 (s, 3H), 4.66 (d, 2H), 5.03 (t, 1H), 7.79 (s, 1H), 7.83 (s, 1H).

Example H

Preparation of N-[3,5-bis(trifluoromethyl)benzyl]-N-{2-[2-(tetrahydropyran-2-yloxy)ethyl]-2H-tetrazol-5-yl}amine

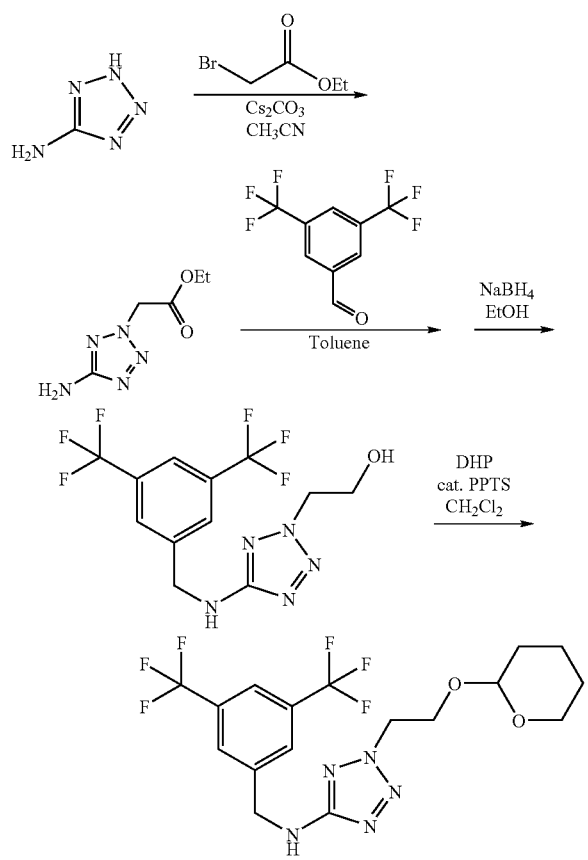

Step 1:

A mixture of 5-aminotetrazole (10.0 g, 0.12 mol), ethyl bromoacetate (20.0 g, 0.12 mol), and Cs$_2$CO$_3$ (40.0 g, 0.13 mol) in acetonitrile (220 mL) is stirred and refluxed for 5 hours. The mixture is cooled to 50° C. and filtrated. The resulting filtrate is concentrated to give the crude coupling product. The mixture of the crude product and 3,5-bis(trifluoromethyl)benzaldehyde (25.0 g, 0.10 mol) in toluene (220 mL) is stirred and refluxed for 5 hours. After cooling to room temperature, the resulting mixture is concentrated. NaBH$_4$ (4.4 g, 0.12 mol) is added portionwise slowly to EtOH (220 mL) solution of the resulting residue, and the mixture is stirred at room temperature for 2 days. After addition of sat. NH$_4$Cl aq. and water, the mixture is extracted with ethyl acetate. The combined organic layer is washed with brine, dried over magnesium sulfate, filtered and concentrated. The crude product is purified by silica gel column chromatography to give 2-(5-{N-[3,5-bis(trifluoromethyl)benzyl]amino}tetrazol-2-yl)ethanol.

$^1$H-NMR (400 MHz, CDCl$_3$), δ (ppm): 2.43-2.55 (m, 1H), 4.08-4.12 (m, 2H), 4.55-4.58 (m, 2H), 4.67 (d, 2H), 5.07-5.12 (m, 1H), 7.80 (s, 1H), 7.84 (s, 2H).

Step 2:

A mixture of 2-(5-{N-[3,5-bis(trifluoromethyl)benzyl]amino}tetrazol-2-yl)ethanol (0.68 g, 1.9 mmol), 3,4-dihydro-2H-pyran (DHP, 0.35 g, 4.2 mmol) and a catalytic amount of pyridinium p-toluene sulfonate (PPTS, 0.050 g, 0.20 mmol) in CH$_2$Cl$_2$ (10 mL) is stirred at room temperature for 10 hours. The resulting mixture is quenched by addition of sat. NaHCO$_3$ aq. and extracted with EtOAc. The organic layer is washed with brine, dried over magnesium sulfate, filtered and concentrated. The crude product is purified by silica gel column chromatography to give N-[3,5-bis(trifluoromethyl)benzyl]-N-{2-[2-(tetrahydropyran-2-yloxy)ethyl]-2H-tetrazol-5-yl}amine.

$^1$H-NMR (400 MHz, CDCl$_3$), δ (ppm): 1.42-1.76 (m, 6H), 3.43-3.48 (m, 1H), 3.68 (ddd, 1H), 3.89-3.95 (m, 1H), 4.12-4.18 (m, 1H), 4.57-4.58 (m, 1H), 4.61 (t, 2H), 4.67 (d, 2H), 4.89-4.97 (m, 1H), 7.79 (s, 1H), 7.84 (s, 2H).

Example I

Preparation of trans-(R)-2-[(4-benzyloxymethyl)cyclohexyl]pyrrolidine

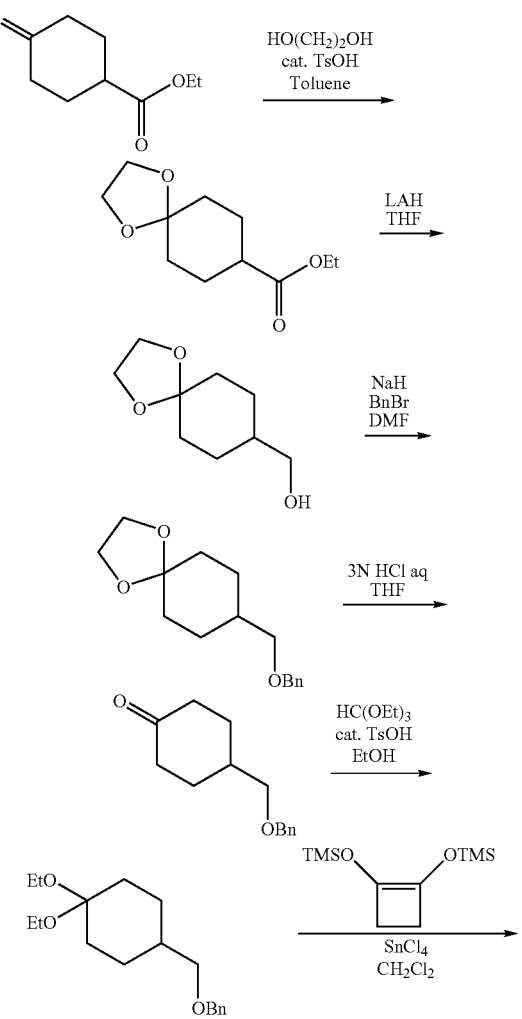

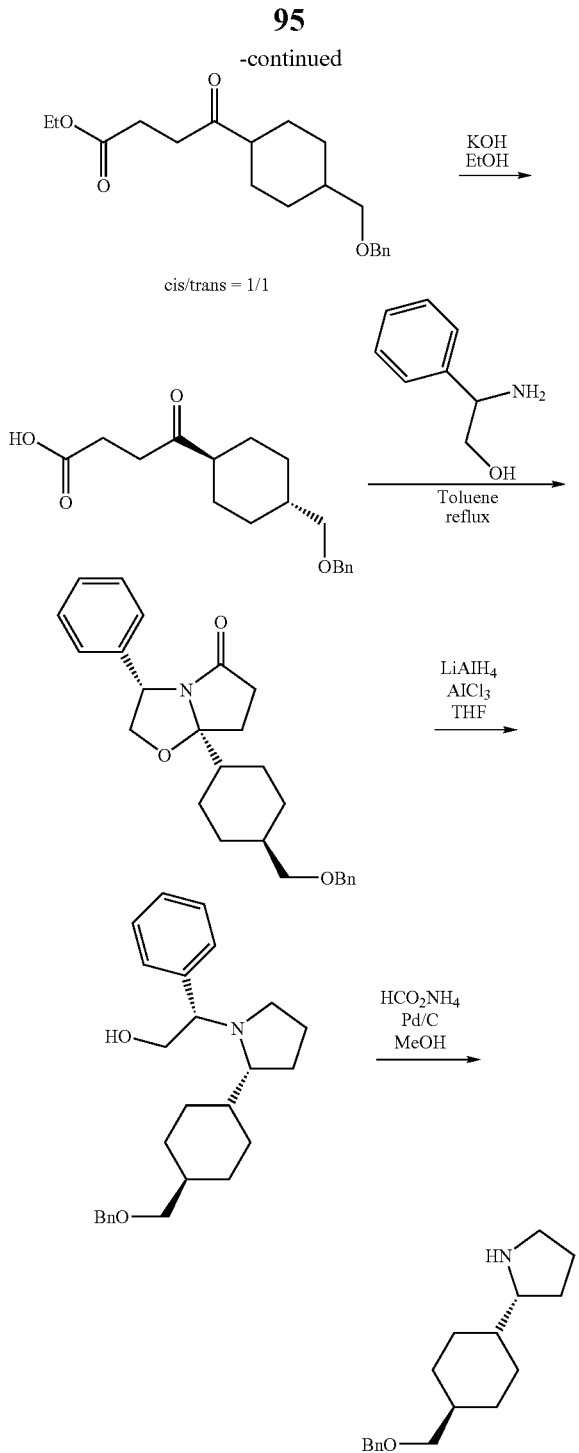

Step 1:

A mixture of 4-ethoxycarbonyl cyclohexanone (175 g, 1.03 mol), ethylenegrycol (70 mL), and p-toluenesulfonic acid (2.1 g) in toluene (700 mL) is stirred and refluxed for 6 hours with continuous water removal using Dean-Stark apparatus. After cooling to room temperature, sat. NaHCO$_3$ aq. (1500 mL) and EtOAc (800 mL) are added to the reaction mixture. The organic layer is washed with brine, dried over magnesium sulfate, and concentrated under reduced pressure to afford crude 1,4-dioxa-spiro[4.5]decane-8-carboxylic acid ethyl ester (220 g) as yellow oil, which is used without further purification.

$^1$H-NMR (400 MHz, CDCl$_3$), δ (ppm): 1.24 (t, 3H), 1.50-1.60 (m, 2H), 1.75-1.86 (m, 4H), 1.90-1.98 (m, 2H), 2.29-2.35 (m, 1H), 3.94 (s, 4H), 4.12 (q, 2H).

Step 2:

To a mixture of lithium aluminum hydride (50.5 g, 1.06 mol) in THF (800 mL) is carefully added crude 1,4-dioxaspiro[4.5]decane-8-carboxylic acid ethyl ester (220 g) in THF (700 mL) at 0° C. over 2.5 hours under argon atmosphere. After stirring 1 hour at ambient temperature, Na$_2$SO$_4$-10H$_2$O (175 g) is added at 0° C., and the mixture is stirred for additional 10 min. Insoluble matter is filtered, and the filtrate is concentrated in vacuo to afford crude (1,4-dioxa-spiro[4.5]dec-8-yl)methanol as a colorless oil, which is used without further purification.

$^1$H-NMR (400 MHz, CDCl$_3$), δ (ppm): 1.22-1.33 (m, 2H), 1.45-1.60 (m, 3H), 1.75-1.83 (m, 4H), 3.49 (d, 2H), 3.91-3.98 (m, 4H).

Step 3:

To a mixture of NaH (60% in oil, 60.9 g, 1.52 mol) in DMF (1500 mL) is carefully added crude (1,4-dioxa-spiro[4.5]dec-8-yl)methanol (150 g) in DMF (50 mL) at 10° C. under argon atmosphere and the mixture is stirred for 1 hour at the same temperature. To the mixture is added benzyl bromide (181 mL) 10° C., and stirring is continued for 3 hours at room temperature. After addition of H$_2$O (70 mL) over 10 min, the mixture is poured into the mixture of H$_2$O (4500 mL) and EtOAc (2000 mL). The water layer is extracted with EtOAc and the combined organic layer is washed with brine, dried over magnesium sulfate, and concentrated under reduced pressure to afford crude 8-benzyloxymethyl-1,4-dioxa-spiro[4.5]decane as a yellow oil. The crude product is used without further purification.

$^1$H-NMR (400 MHz, CDCl$_3$), δ (ppm): 1.22-1.33 (m, 2H), 1.50-1.59 (m, 2H), 1.62-1.74 (m, 1H), 1.73-1.86 (m, 4H), 3.31 (d, 2H), 3.90-3.97 (m, 4H), 4.50 (s, 2H), 7.26-7.35 (m, 5H).

Step 4:

To a mixture of crude 8-benzyloxymethyl-1,4-dioxa-spiro[4.5]decane (297 g) in THF (600 mL) is added 3N HCl (900 mL) at room temperature, and the mixture is stirred overnight. After addition of sat. NaHCO$_3$ aq., the mixture is extracted with EtOAc. The water layer is extracted with EtOAc, and the combined organic layer is washed with brine, dried over magnesium sulfate, and concentrated under reduced pressure. The crude mixture is purified by silica gel column chromatography to afford 4-benzyloxymethylcyclohexanone.

$^1$H-NMR (400 MHz, CDCl$_3$), δ (ppm): 1.41-1.53 (m, 2H), 2.03-2.18 (m, 3H), 2.28-2.43 (m, 4H), 3.39 (d, 2H), 4.53 (s, 2H), 7.26-7.38 (m, 5H).

Step 5:

4-Benzyloxymethylcyclohexanone (168 g, 0.77 mol) is dissolved in ethanol (2000 mL), and then triethylorthoformate (350 mL) and p-toluenesulfonic acid (13.3 g) are added. The resulting mixture is stirred and refluxed for 6 hours. After addition of triethylamine (10.5 mL) at room temperature, the mixture is concentrated (500 mL). After addition of sat. NaHCO$_3$ aq., the resulting mixture is extracted with EtOAc. The water layer is extracted with EtOAc and the combined organic layer is washed with brine, dried over magnesium sulfate, and concentrated under reduced pressure. The crude mixture is purified by short pad silica gel column chromatography to afford (4,4-diethoxycyclohexylmethoxymethyl) benzene.

$^1$H-NMR (400 MHz, CDCl$_3$), δ (ppm): 1.12-1.19 (m, 2H), 1.16 (t, 3H), 1.17 (t, 3H), 1.31-1.42 (m, 2H), 1.62-1.75 (m, 3H), 1.97-2.04 (m, 2H), 3.31 (d, 2H), 3.41 (q, 2H), 4.50 (q, 2H), 4.50 (s, 2H), 7.25-7.37 (m, 5H).

Step 6:

To a mixture of tin tetrachloride (199 g, 0.77 mol) in CH$_2$Cl$_2$ (1800 mL) is added (4,4-diethoxycyclohexylmethoxymethyl)benzene (225 g) and 1,2-bis(trimethylsiloxy)cyclobutene (176 g, 0.77 mol) in CH$_2$Cl$_2$ (900 mL) at −56 to −47° C. over 40 min. The mixture is stirred for 15 min at −50° C. The cooled reaction mixture is poured into water (5000 mL), and the water layer is extracted with CH$_2$Cl$_2$. The combined organic layer is washed with sat. NaHCO$_3$ aq. and brine, dried over magnesium sulfate, and concentrated under reduced pressure. The crude mixture is purified by short-pad silica gel column chromatography to afford ethyl 4-[4-(benzyloxymethyl)cyclohexyl]-4-oxobutyrate (cis/trans=1/1) as a yellow oil.

$^1$H-NMR (400 MHz, CDCl$_3$, cis:trans 1:1 mixture), δ (ppm): 0.97-1.08 (m, 1H), 1.24 (t, 3H), 1.33-1.44 (m, 2H), 1.55-1.67 (m, 3H), 1.77-1.98 (m, 3H), 2.34 (tt, 0.5H), 2.51-2.58 (m, 0.5H), 2.57 (t, 2H), 2.74 (t, 1H), 2.75 (t, 1H), 3.29 (d, 1H), 3.32 (d, 1H), 4.12 (q, 2H), 4.48 (s, 1H), 4.49 (s, 1H), 7.25-7.37 (m, 5H).

Step 7:

Potassium hydroxide (17.0 g, 0.30 mol) is added to EtOH (300 mL) solution of ethyl 4-[4-(benzyloxymethyl)cyclohexyl]-4-oxobutyrate (cis/trans=1/1, 33.0 g, 0.10 mol), and the mixture is stirred at 85° C. for 2 hours. After cooling to 0° C., 5N HCl is added to the mixture (to reach pH 2-3), the mixture is concentrated to remove ethanol. The crude mixture is extracted with EtOAc. The water layer is extracted with EtOAc, and the combined organic layer is washed with water and brine, dried over magnesium sulfate, and concentrated under reduced pressure to afford crude 4-[4-(benzyloxymethyl)cyclohexyl]-4-oxobutyric acid (cis/trans=ca. 1/6). The mixture of ether-hexane (ca. 1:4, 120 mL) is added to the resulting solid and sonicated. The crystal is collected by filtration, washed with small amount of ether-hexane (1:4) and dried to give trans-4-[4-(benzyloxymethyl)cyclohexyl]-4-oxobutyric acid as a pale yellow solid.

$^1$H-NMR (400 MHz, CDCl$_3$), δ (ppm): 0.97-1.09 (m, 2H), 1.31-1.43 (m, 2H), 1.56-1.68 (m, 1H), 1.89-1.98 (m, 4H), 2.34 (tt, 1H), 2.62 (t, 2H), 2.76 (t, 2H), 3.29 (d, 2H), 4.49 (s, 2H), 7.26-7.38 (m, 5H).

Step 8:

To a stirred solution of (S)-(+)-phenylglycinol (6.85 g, 50 mmol) in toluene (150 mL) is added trans-4-[4-(benzyloxymethyl)cyclohexyl]-4-oxobutyric acid (15.2 g, 50 mmol), and the resulting mixture is heated to reflux for 4 hours with continuous water removal by using Dean-stark apparatus. The resulting mixture is concentrated, and the resulting residue is purified by silica gel column chromatography to afford trans-(3S,7aS)-7a-[4-(benzyloxymethyl)cyclohexyl]-3-phenyltetrahydropyrrolo[2,1-b]oxazol-5-one.

$^1$H-NMR (400 MHz, CDCl$_3$), δ (ppm): 0.73-0.89 (m, 2H), 1.08-1.21 (m, 2H), 1.51 (tt, 1H), 1.53-1.63 (m, 1H), 1.83-2.97 (m, 4H), 1.98 (tt, 1H), 2.43 (ddd, 1H), 2.58 (ddd, 1H), 2.75 (dt, 1H), 3.23 (d, 2H), 4.07 (dd, 1H), 4.46 (s, 2H), 4.64 (t, 1H), 5.19 (t, 1H), 7.19-7.22 (m, 2H), 7.24-7.38 (m, 8H).

Step 9:

To a cooled (0° C.) mixture of anhydrous AlCl$_3$ (4.70 g, 35 mmol) in THF (120 mL) is slowly added lithium aluminum hydride (4.34 g, 115 mmol), and the resulting mixture is stirred at the same temperature for 30 min. To the resulting stirred and cooled (−78° C.) THF mixture is added a solution of trans-(3S,7aS)-7a-[4-(benzyloxymethyl)cyclohexyl]-3-phenyltetrahydropyrrolo[2,1-b]oxazol-5-one (15.5 g, 38 mmol) in THF (80 mL) over 30 min. The resulting mixture is stirred at the same temperature for 1.5 hours, and then warmed to room temperature and stirred for additional 15 min. The resulting mixture is cooled to 0° C., quenched with the careful addition of Na$_2$SO$_4$-10H$_2$O (5.0 g), and stirred for additional 30 min at room temperature. The insoluble matter is filtered and the filtrate is concentrated in vacuo to afford crude trans-(S)-2-{(R)-2-[4-benzyloxymethyl)cyclohexyl]pyrrolidin-1-yl}-2-phenylethanol, which is used without further purification.

$^1$H-NMR (400 MHz, CDCl$_3$), δ (ppm): 0.95-1.16 (m, 4H), 1.40-1.66 (m, 6H), 1.67-1.76 (m, 1H), 1.77-1.85 (m, 1H), 1.86-1.94 (m, 2H), 2.20-2.28 (m, 1H), 2.58-2.66 (m, 1H), 2.87-2.93 (m, 1H), 3.31 (dd, 2H), 3.59-3.65 (m, 1H), 3.96-4.04 (m, 2H), 4.51 (s, 2H), 7.15-7.17 (m, 2H), 7.25-7.49 (m, 8H).

Step 10:

To a stirred mixture of anhydrous ammonium formate (6.87 g, 0.11 mol) and trans-(S)-2-{(R)-2-[4-benzyloxymethyl)cyclohexyl]pyrrolidin-1-yl}-2-phenylethanol (10.7 g, 0.027 mol) in MeOH (135 mL) is added 10% palladium on carbon (0.54 g), and the resulting mixture is stirred at room temperature under nitrogen atmosphere for 2 hours. Anhydrous ammonium formate (3.45 g) and 10% palladium on carbon (0.54 g) are added, and the mixture is stirred at room temperature under nitrogen atmosphere for another 3 hours. The reaction mixture is filtered, and the filtrate is concentrated. The crude residue (18.26 g) is dissolved with 1N HCl and extracted with ether to remove phenethylalcohol. The water layer is neutralized by addition of 2N NaOH and extracted with CH$_2$Cl$_2$. The combined CH$_2$Cl$_2$ layer is washed with brine, dried over magnesium sulfate, filtered and concentrated to give crude trans-(R)-2-[4-benzyloxymethyl)cyclohexyl]pyrrolidine (6.54 g). To a mixture of crude trans-(R)-2-[4-benzyloxymethyl)cyclohexyl]pyrrolidine in EtOH (20 mL), L-tartaric acid (3.59 g, 0.024 mol) is added. The mixture is warmed to 60° C. until the mixture becomes clear, then the mixture is cooled down slowly to room temperature. The resulting precipitate is filtered and rinsed with additional EtOH to afford pure trans-(R)-2-[4-(benzyloxymethyl)cyclohexyl]pyrrolidine tartaric acid salt as off-white crystals. The tartaric acid salt is dissolved in 1N NaOH aq. and extracted with CH$_2$Cl$_2$. The organic layer is dried over magnesium sulfate, filtered and evaporated to afford pure trans-(R)-2-[4-(benzyloxymethyl)cyclohexyl]pyrrolidine.

$^1$H-NMR (400 MHz, CDCl$_3$), δ (ppm): 0.89-1.06 (m, 4H), 1.11-1.20 (m, 1H), 1.24-1.34 (m, 1H), 1.46-1.78 (m, 4H), 1.80-1.89 (m, 3H), 1.95-2.00 (m, 1H), 2.62 (dt, 1H), 2.81 (ddd, 1H), 2.99 (ddd, 1H), 3.27 (d, 2H), 4.49 (s, 2H), 7.22-7.36 (m, 5H).

Example J

Preparation of trans-N-(2-{(R)-2-[4-(2-benzyloxymethyl)cyclohexyl]pyrrolidin-1-yl}-6,7-difluoroquinolin-3-ylmethyl)-N-[3,5-bis(trifluoromethyl)benzyl](2-methyl-2H-tetrazol-5-yl)amine

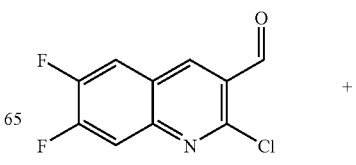

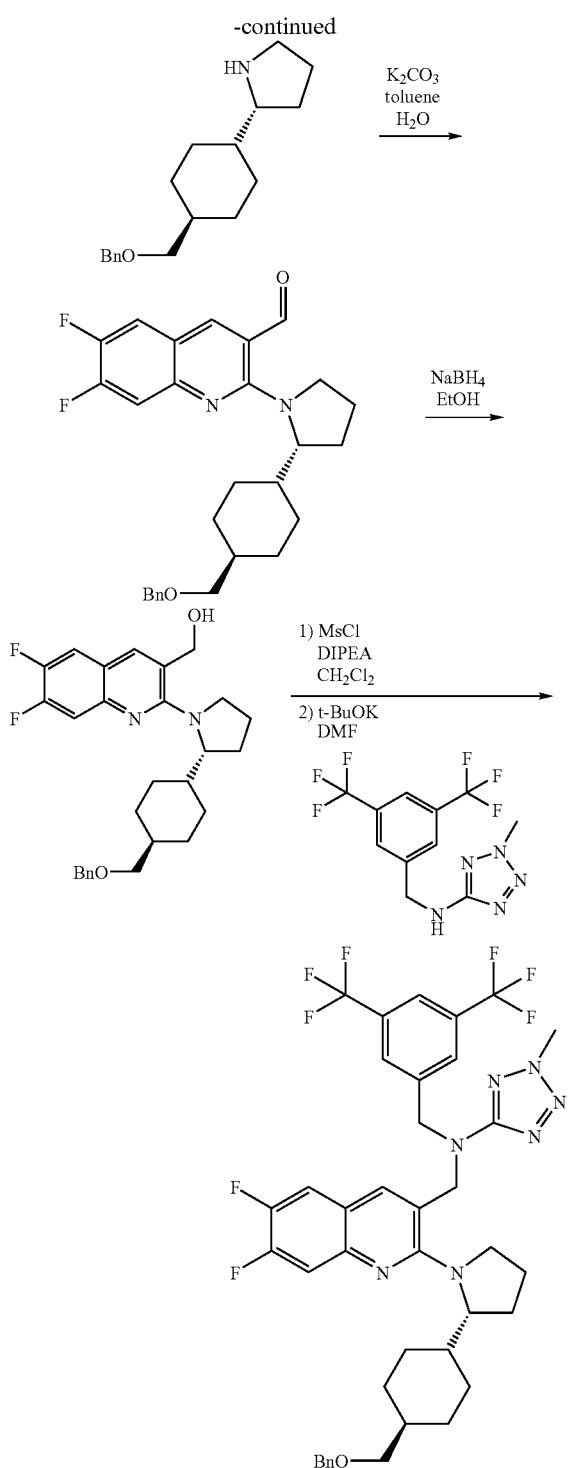

Step 1:

A suspension of 2-chloro-6,7-difluoroquinoline-3-carbaldehyde (4.97 g, 18 mmol), trans-(R)-2-[(4-benzyloxymethyl)cyclohexyl]pyrrolidine (5.39 g, 20 mmol) and potassium carbonate (2.97 g, 21 mol) in toluene (100 mL) and water (10 mL) is stirred and refluxed for 3 hours. The reaction mixture is cooled to room temperature and then diluted with water and ethyl acetate. The organic layer is washed with water, citric acid aq., brine, dried over magnesium sulfate, filtered and concentrated. The crude product is purified by silica gel column chromatography to give 2-{(R)-2-[4-(benzyloxymethyl)cyclohexyl]pyrrolidin-1-yl}-6,7-difluoroquinoline-3-carbaldehyde as a yellow syrup.

$^1$H-NMR (400 MHz, CDCl$_3$), δ (ppm): 0.81-1.04 (m, 2H), 1.08-1.21 (m, 2H), 1.55-1.74 (m, 3H), 1.76-1.90 (m, 4H), 1.91-2.07 (m, 3H), 3.18-3.24 (m, 1H), 3.25 (d, 2H), 3.69 (dt, 1H), 4.47 (s, 2H), 4.66-4.74 (m, 1H), 7.26-7.34 (m, 5H), 7.40-7.47 (m, 2H), 8.31 (s, 1H), 10.13 (s, 1H).

Step 2:

2-{(R)-2-[4-(benzyloxymethyl)cyclohexyl]pyrrolidin-1-yl}-6,7-difluoroquinoline-3-carbaldehyde (7.25 g, 16 mmol) is dissolved with ethanol (80 mL) and treated with sodium borohydride (0.30 g, 7.9 mmol) at 0° C., and the resulting mixture is stirred at room temperature for 30 min. After addition of water and ethyl acetate, the mixture is partially concentrated to remove ethanol. The mixture is extracted with EtOAc, and the organic layer is washed with brine, sat. NH$_4$Cl aq., dried over magnesium sulfate, filtered and concentrated.

The crude product is purified by silica gel column chromatography to give (2-{R)-2-[4-(benzyloxymethyl)cyclohexyl]pyrrolidin-1-yl}-6,7-difluoroquinolin-3-yl)methanol as a yellow syrup.

$^1$H-NMR (400 MHz, CDCl$_3$), δ (ppm): 0.74-0.97 (m, 2H), 1.00-1.14 (m, 2H), 1.49-1.63 (m, 2H), 1.69-1.84 (m, 6H), 1.88-2.05 (m, 2H), 2.44 (dd, 1H), 3.21 (d, 2H), 3.27-3.33 (m, 1H), 3.60 (dt, 1H), 4.45 (s, 2H), 4.62-4.66 (m, 1H), 4.73 (dd, 1H), 4.87 (dd, 1H), 7.22-7.34 (m, 5H), 7.37 (dd, 1H), 7.48 (dd, 1H), 7.93 (s, 1H).

Step 3:

Methaneslufonyl chloride (1.52 mL, 20 mmol) is added dropwise to a mixture of (2-{(R)-2-[4-(benzyloxymethyl)cyclohexyl]pyrrolidin-1-yl}-6,7-difluoroquinolin-3-yl)methanol (7.03 g, 15 mmol) and N,N-diisopropylethylamine (DIPEA, 3.41 mL, 15 mmol) in toluene (75 mL) at 0° C. The reaction mixture is stirred at ambient temperature for 1 hour. To the mixture, water and ethyl acetate are added, and the organic layer is washed with sat. NaHCO$_3$ aq, brine, dried over magnesium sulfate, filtered and concentrated in vacuo. The residue is dissolved with toluene and concentrated in vacuo to give crude 2-{(R)-2-[4-(benzyloxymethyl)cyclohexyl]pyrrolidin-1-yl}-3-(chloromethyl)-6,7-difluoroquinoline. To a mixture of N-[3,5-bis(trifluoromethyl)benzyl]-N-(2-methyl-2H-tetrazol-5-yl)amine (5.88 g, 18 mmol) in DMF (60 mL) is added potassium tert-butoxide (2.03 g, 18 mmol) at 0° C., and the resulting mixture is stirred for 30 min at the same temperature. A crude 2-{(R)-2-[4-(benzyloxymethyl)cyclohexyl]pyrrolidin-1-yl}-3-(chloromethyl)-6,7-difluoroquinoline dissolved in DMF (30 mL) is added dropwise to the mixture at 0° C., and the resulting mixture is stirred for 1 hour at the same temperature. Potassium tert-butoxide (1.70 g, 14 mmol) is added to the reaction mixture, and the mixture is stirred another 1 hour at room temperature. After adding water, the mixture is extracted with ethyl acetate. The combined organic layer is washed with brine, dried over magnesium sulfate, filtrated, and concentrated. The resulting mixture is purified by silica gel column chromatography to give trans-N-(2-{(R)-2-[4-(2-benzyloxymethyl)cyclohexyl]pyrrolidin-1-yl}-6,7-difluoroquinolin-3-ylmethyl)N-[3,5-bis(trifluoromethyl)benzyl](2-methyl-2H-tetrazol-5-yl)amine as a yellow amorphous solid.

$^1$H-NMR (400 MHz, CDCl$_3$), δ (ppm): 0.74-0.95 (m, 2H), 0.99-1.12 (m, 2H), 1.48-1.59 (m, 2H), 1.64-1.83 (m, 6H), 1.84-1.90 (m, 1H), 1.96-2.04 (m, 1H), 3.16-3.22 (m, 1H), 3.22 (d, 2H), 3.49-3.55 (m, 1H), 4.20 (s, 3H), 4.46 (s, 2H), 4.55 (d, 1H), 4.57 (d, 1H), 4.60-4.65 (m, 1H), 4.78 (d, 1H), 4.98 (d, 1H), 7.21 (dd, 1H), 7.25-7.33 (m, 5H), 7.47 (dd, 1H), 7.55 (s, 1H), 7.63 (s, 2H), 7.72 (s, 1H).

Example K

Preparation of trans-(R)-2-[4-(2-benzyloxyethyl)cyclohexyl]pyrrolidine

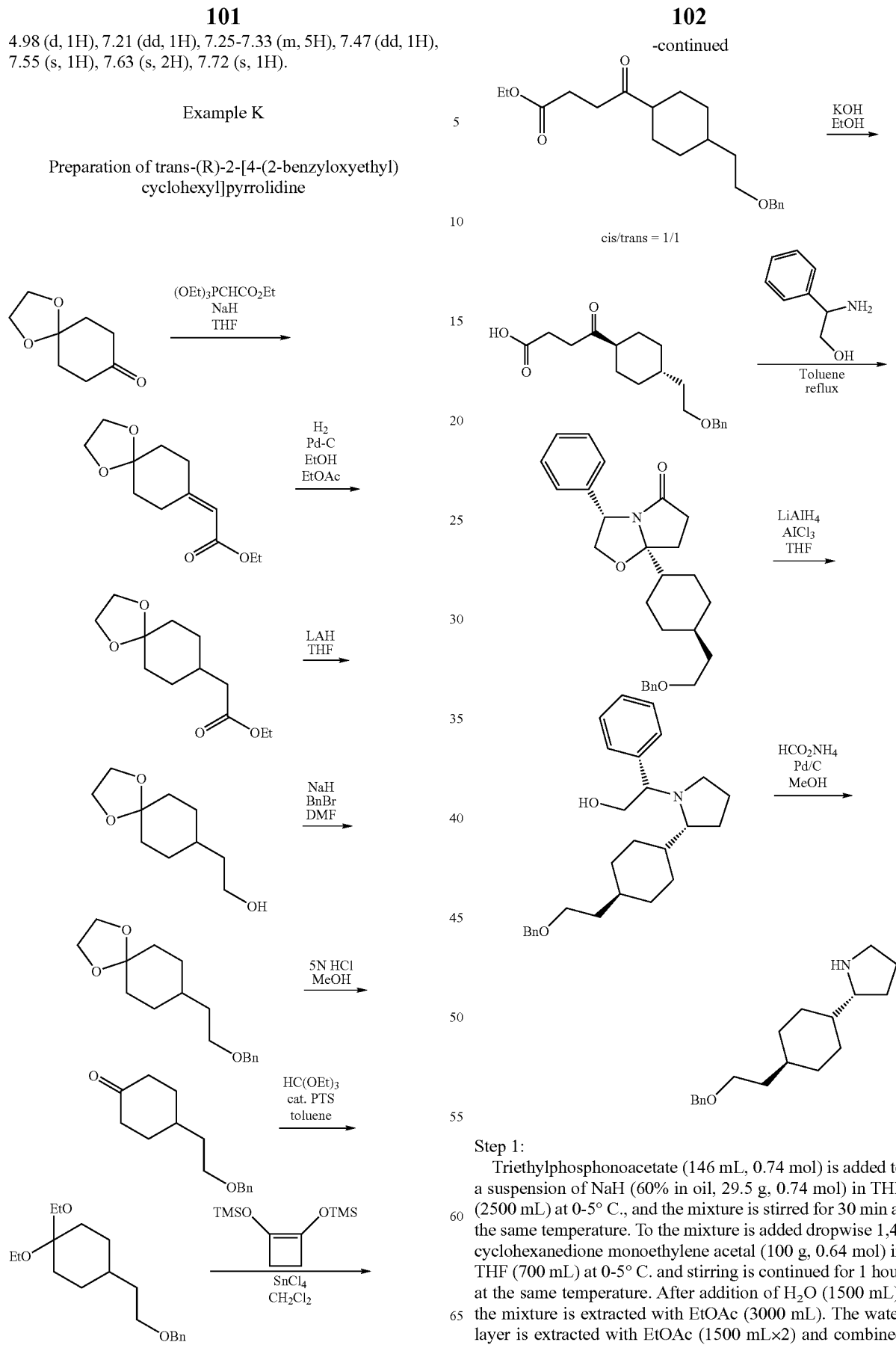

cis/trans = 1/1

Step 1:

Triethylphosphonoacetate (146 mL, 0.74 mol) is added to a suspension of NaH (60% in oil, 29.5 g, 0.74 mol) in THF (2500 mL) at 0-5° C., and the mixture is stirred for 30 min at the same temperature. To the mixture is added dropwise 1,4-cyclohexanedione monoethylene acetal (100 g, 0.64 mol) in THF (700 mL) at 0-5° C. and stirring is continued for 1 hour at the same temperature. After addition of H₂O (1500 mL), the mixture is extracted with EtOAc (3000 mL). The water layer is extracted with EtOAc (1500 mL×2) and combined organic layer is washed with brine, dried over magnesium sulfate, and concentrated under reduced pressure to afford 8-ethoxycarbonylmethylidene-1,4-dioxaspiro[4.5]decane (172.9 g) as a colorless oil. The crude product is used without further purification.

$^1$H-NMR (400 MHz, CDCl$_3$), δ (ppm): 1.28 (t, 3H), 1.74-1.80 (m, 4H), 2.38 (ddd, 2H), 3.00 (ddd, 2H), 3.98 (s, 4H), 4.15 (q, 2H), 5.67 (s, 1H).

Step 2:

A suspension of 8-ethoxycarbonylmethylidene-1,4-dioxaspiro[4.5]decane (crude, 172.9 g) 10% Pd—C (53.2% wet, 6.5 g) in EtOAc/MeOH (1250 mL and 400 mL) is stirred under H$_2$ atmosphere at room temperature for 4 hours. The reaction mixture is filtered, and the filtrate is concentrated in vacuo to afford crude 8-ethoxycarbonylmethyl-1,4-dioxaspiro[4.5]decane. The crude product is used without further purification.

$^1$H-NMR (400 MHz, CDCl$_3$), δ (ppm): 1.25 (t, 3H), 1.27-1.37 (m, 2H), 1.57 (ddd, 2H), 1.70-1.78 (m, 4H), 1.80-1.90 (m, 1H), 2.22 (d, 2H), 3.91-3.95 (m, 4H), 4.13 (q, 2H).

Step 3:

To a mixture of lithium aluminum hydride (42.5 g, 1.12 mol) in THF (1200 mL) is carefully added crude 8-ethoxycarbonylmethyl-1,4-dioxaspiro[4.5]decane (174.7 g) in THF solution (640 mL) at 0° C. under argon atmosphere. After stirring for 10 min at ambient temperature, Na$_2$SO$_4$-10H$_2$O (360.9 g) is added at 0° C., and the mixture is stirred for additional 3 hours. Insoluble matter is filtered and washed with EtOAc, and the filtrate is concentrated in vacuo to afford crude 2-(1,4-dioxaspiro[4.5]dec-8-yl)ethanol (139.5 g). The crude product is used without further purification.

$^1$H-NMR (400 MHz, CDCl$_3$), δ (ppm): 1.22-1.36 (m, 4H), 1.44-1.58 (m, 4H), 1.70-1.78 (m, 4H), 3.69 (dt, 2H), 3.94 (s, 4H).

Step 4:

To a mixture of NaH (60% in oil, 43.6 g, 1.09 mol) in DMF (900 mL) is carefully added crude 2-(1,4-dioxaspiro[4.5]dec-8-yl)ethanol (139.5 g) in DMF (300 mL) at 0-5° C., and the mixture is stirred for 30 min at the same temperature. To the mixture is added dropwise benzyl bromide (129.6 mL, 1.09 mol) at 0-5° C., and stirring is continued for 1 hour at the same temperature. After addition of H$_2$O (1000 mL), the mixture is extracted with EtOAc-Hexane (3:1, 1200 mL). The water layer is extracted with EtOAc-Hexane (3:1, 1200 mL×2), and the combined organic layer is washed with brine, dried over magnesium sulfate, and concentrated under reduced pressure to afford crude 8-[2-(benzyloxy)ethyl]-1,4-dioxaspiro[4.5]decane. The crude product is used without further purification.

$^1$H-NMR (400 MHz, CDCl$_3$), δ (ppm): 1.25 (m, 2H), 1.52 (m, 5H), 1.74 (m, 4H), 3.50 (t, 2H), 3.93 (s, 4H), 4.49 (s, 2H), 7.34 (m, 5H).

Step 5:

To a mixture of crude 8-[2-(benzyloxy)ethyl]-1,4-dioxaspiro[4.5]decane (227.8 g) in THF (500 mL) is added 5N HCl (600 mL) at room temperature, and the mixture is stirred for 10 hours at the same temperature. After addition of NaHCO$_3$ aq. (300 g in 500 mL water), the mixture is extracted with EtOAc (1500 mL). The water layer is extracted with EtOAc (1000 mL×2), and the combined organic layer is washed with brine, dried over magnesium sulfate, and concentrated under reduced pressure. The crude mixture is purified by silica gel column chromatography to afford 4-(2-benzyloxyethyl)cyclohexanone.

$^1$H-NMR (400 MHz, CDCl$_3$), δ (ppm): 1.35-1.46 (m, 2H), 1.63 (dt, 2H), 1.87-2.00 (m, 1H), 2.01-2.09 (m, 2H), 2.28-2.42 (m, 4H), 3.54 (t, 2H), 4.52 (s, 2H), 7.27-7.36 (m, 5H).

Step 6:

4-(2-benzyloxyethyl)cyclohexanone (133.0 g, 0.57 mol) is dissolved in ethanol (1200 mL), and then triethylorthoformate (296 mL) and p-toluenesulfonic acid monohydrate (10.9 g, 0.057 mol) are added. The resulting mixture is stirred and refluxed for 2 hours. After addition of triethylamine (8.8 mL, 0.063 mol) at room temperature, the mixture is concentrated. After addition of sat. NaHCO$_3$ aq. (500 mL), the resulting mixture is extracted with EtOAc (1000 mL). The water layer is extracted with EtOAc (1000 mL×2) and the combined organic layer is washed with brine, dried over magnesium sulfate, and concentrated under reduced pressure. The crude mixture is purified by short pad silica gel column chromatography to afford [2-(4,4-diethoxycyclohexyl)ethoxymethyl]benzene as a pale yellow oil.

$^1$H-NMR (400 MHz, CDCl$_3$), δ (ppm): 1.12-1.17 (m, 2H), 1.16 (t, 3H), 1.17 (t, 3H), 1.36 (ddd, 2H), 1.42-1.48 (m, 1H), 1.52-1.64 (m, 4H), 1.93-2.01 (m, 2H), 3.40 (q, 2H), 3.49 (q, 2H), 3.50 (t, 2H), 4.50 (s, 2H), 7.25-7.38 (m, 5H).

Step 7:

To a mixture of tin tetrachloride (131 mL, 1.23 mol) in CH$_2$Cl$_2$ (2600 mL) is added [2-(4,4-diethoxycyclohexyl)ethoxymethyl]benzene (344 g, 1.12 mol) and 1,2-bis(trimethylsiloxy)cyclobutene (317 mL, 1.23 mol) in CH$_2$Cl$_2$ (1500 mL) at −70° C. The mixture is stirred for 2 hours at −40° C. The cooled reaction mixture is poured into water (1000 mL) and extracted with CH$_2$Cl$_2$ (1000 mL). The combined organic layer is washed with sat. NaHCO$_3$ aq. and brine, dried over magnesium sulfate, and concentrated under reduced pressure. The crude mixture is purified by silica gel column chromatography to afford ethyl 4-{[4-(2-benzyloxy)ethyl]cyclohexyl}-4-oxobutyrate (cis/trans=1/1) as a pale yellow oil.

$^1$H-NMR (400 MHz, CDCl$_3$, cis:trans=1/1), δ (ppm): 0.90-1.02 (m, 1H), 1.25 (t, 3H), 1.33-1.44 (m, 2H), 1.50-1.67 (m, 5H), 1.79-1.94 (m, 3H), 2.33 (tt, 0.5H), 2.47-2.53 (m, 0.5H), 2.56 (t, 1H), 2.57 (t, 1H), 2.74 (t, 2H), 3.47 (t, 1H), 3.50 (t, 1H), 4.12 (q, 2H), 4.48 (s, 1H), 4.49 (s, 1H), 7.25-7.37 (m, 5H).

Step 8:

Potassium hydroxide (192 g, 3 mol) is added to EtOH (2000 mL) solution of ethyl 4-{[4-(2-benzyloxy)ethyl]cyclohexyl}-4-oxobutyrate (346.2 g, 1.0 mol), and the resulting mixture is stirred and refluxed for 3 hours. After addition of 5N HCl (to reach pH 2) at 0° C., the mixture is extracted with EtOAc (4000 mL). The water layer is extracted with EtOAc (1000 mL), and the combined organic layer is washed with brine, dried over magnesium sulfate, and concentrated under reduced pressure to obtain brown solid. The solid is suspended in Et$_2$O-hexane (1:4), and collected by filtration to afford trans-4-{[4-(2-benzyloxy)ethyl]cyclohexyl}-4-oxobutyric acid as a pale yellow solid.

$^1$H-NMR (400 MHz, CDCl$_3$), δ (ppm): 0.90-1.02 (m, 2H), 1.22-1.45 (m, 3H), 1.54 (dt, 2H), 1.80-1.94 (m, 4H), 2.32 (tt, 1H), 2.62 (t, 2H), 2.76 (t, 2H), 3.50 (t, 2H), 4.49 (s, 2H), 7.26-7.36 (m, 5H).

Step 9:

To a stirred solution of (S)-(+)-phenylglycinol (16.4 g, 0.12 mol) in toluene (450 mL) is added trans-4-{[4-(2-benzyloxy)ethyl]cyclohexyl}-4-oxobutyric acid (38.0 g, 0.12 mol). The resulting mixture is heated to reflux for 5 hours with continuous water removal by using Dean-stark apparatus. The mixture is concentrated, and the resulting residue is purified by silica gel column chromatography to afford trans-(3S,7aS)-7a-[4-(benzyloxyethyl)cyclohexyl]-3-phenyltetrahydropyrrolo[2,1-b]oxazol-5-one as a colorless solid.

¹H-NMR (400 MHz, CDCl₃), δ (ppm): 0.67-0.84 (m, 2H), 1.06-1.21 (m, 2H), 1.30-1.52 (m, 4H), 1.73-1.93 (m, 4H), 1.96 (dt, 1H), 2.43 (ddd, 1H), 2.58 (ddd, 1H), 2.75 (dt, 1H), 3.47 (t, 2H), 4.06 (dd, 1H), 4.48 (s, 2H), 4.64 (t, 1H), 5.19 (t, 1H), 7.19-7.23 (m, 2H), 7.24-7.36 (m, 8H).

Step 10:

To a cooled (0° C.) mixture of anhydrous AlCl₃ (6.30 g, 47 mmol) in THF (300 mL) is slowly added lithium aluminum hydride (5.95 g, 157 mmol), and the resulting mixture is stirred at the same temperature for 10 min. To the resulting stirred and cooled (−65° C.) THF mixture is added trans-(3S, 7aS)-7a-[4-(benzyloxyethyl)cyclohexyl]-3-phenyltetrahydropyrrolo[2,1-b]oxazol-5-one (22.0 g, 52 mmol) dissolved in THF (150 mL) over 30 min. The resulting mixture is stirred at the same temperature for 2 hours, and then warmed to room temperature and stirred additional 1 hour. The resulting mixture is cooled to 0° C., quenched by careful addition of Na₂SO₄-10H₂O, and stirred for additional 30 min at room temperature. The insoluble matter is filtered and the filtrate is concentrated in vacuo to afford crude trans-(S)-2{(R)-2-[4-(benzyloxyethyl)cyclohexyl]pyrrolidin-1-yl}-2-phenylethanol, which is used without further purification.

¹H-NMR (400 MHz, CDCl₃), δ (ppm): 0.94-1.13 (m, 4H), 1.35-1.88 (m, 12H), 2.20-2.29 (m, 1H), 2.58-2.63 (m, 1H), 2.86-2.94 (m, 1H), 3.52 (t, 2H), 3.61-3.66 (m, 1H), 3.95-4.04 (m, 2H), 4.51 (s, 2H), 7.14-7.18 (m, 2H), 7.28-7.52 (m, 8H).

Step 11:

To a stirred mixture of anhydrous ammonium formate (15.8 g, 0.25 mol) and trans-(S)-2-{(R)-2-[4-(benzyloxyethyl)cyclohexyl]pyrrolidin-1-yl}-2-phenylethanol (20.5 g, 0.050 mol) in MeOH (200 mL) is added 10% palladium on carbon (1.00 g), and the resulting mixture is stirred under nitrogen atmosphere at room temperature for 2 hours and then at 35° C. for 3 hours. The reaction mixture is filtered, and the filtrate is concentrated. The crude residue is dissolved with 1N HCl and extracted with ether to remove phenethylalcohol. The water layer is neutrized by addition of 2.5; N NaOH and extracted with CH₂Cl₂. The combined organic layer is washed with brine, dried over magnesium sulfate, filtered and concentrated to give crude trans-(R)-2-[4-(benzyloxyethyl)cyclohexyl]pyrrolidine. To the mixture of crude trans-(R)-2-[4-(benzyloxyethyl)cyclohexyl]pyrrolidine in EtOH (65 mL), L-tartaric acid (7.60 g, 0.050 mol) is added. The resulting mixture is warmed to 60° C., then cooled slowly to room temperature. The precipitate is filtered and rinsed with additional EtOH to afford trans-(R)-2-[4-(benzyloxyethyl)cyclohexyl]pyrrolidine tartaric acid salt as off-white crystal. The tartaric acid salt is dissolved in 1N NaOH aq. and extracted with CH₂Cl₂, and the organic layer is dried over magnesium sulfate, filtered, and evaporated to afford pure trans-(R)-2-[4-(benzyloxyethyl)cyclohexyl]pyrrolidine.

¹H-NMR (400 MHz, CDCl₃), δ (ppm): 0.86-1.05 (m, 4H), 1.09-1.19 (m, 1H), 1.21-1.43 (m, 2H), 1.51 (dt, 2H), 1.60-1.94 (m, 7H), 2.62 (dt, 1H), 2.80 (ddd, 1H), 2.99 (ddd, 1H), 3.50 (t, 2H), 4.49 (s, 2H), 7.22-7.36 (m, 5H).

Example L

Preparation of trans-N-[2-((R)-2-{4-[2-(benzyloxy)ethyl]cyclohexyl}pyrrolidin-1-yl)-6,7-difluoroquinolin-3-ylmethyl]-N-[3,5-bis(trifluoromethyl)benzyl](2-methyl-2H-tetrazol-5-yl)amine

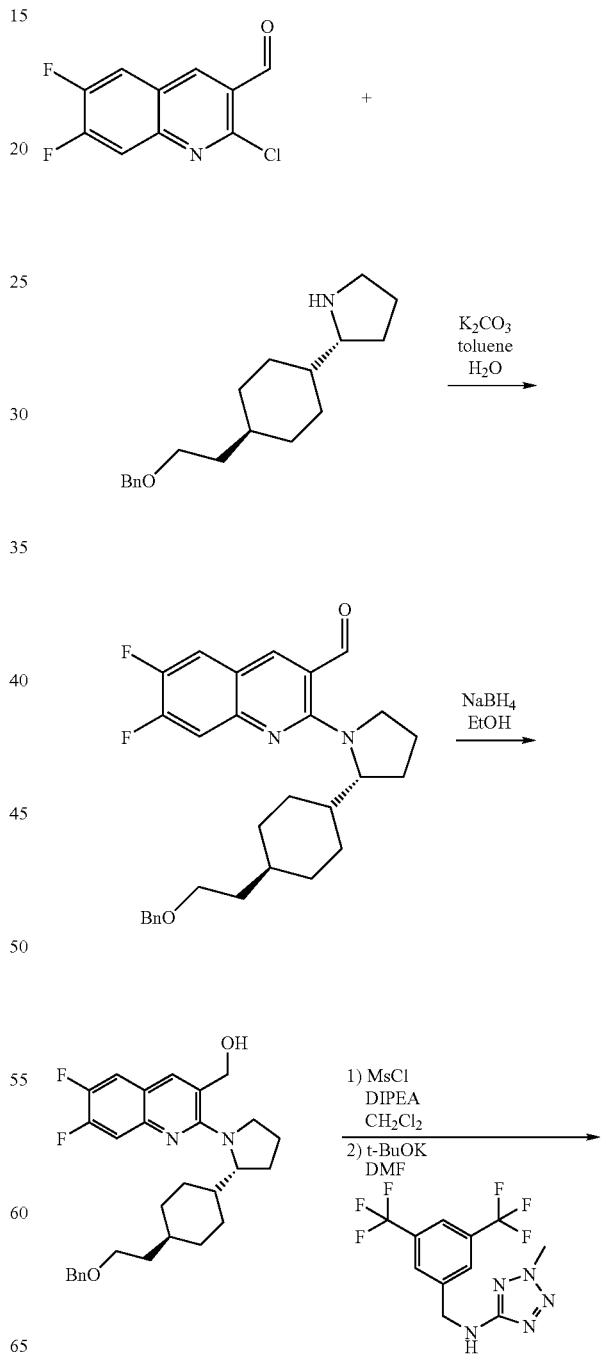

-continued

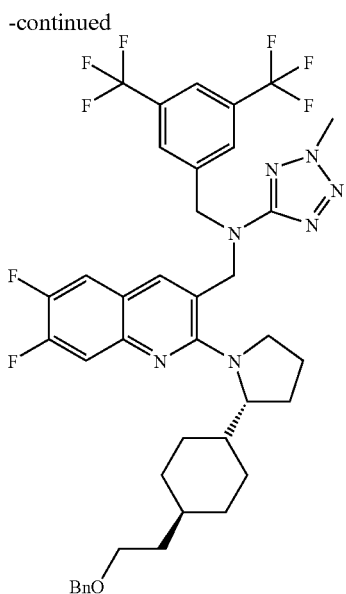

Step 1:
A suspension of 2-chloro-6,7-difluoroquinoline-3-carbaldehyde (8.30 g, 36 mmol), trans-(R)-2-[4-(benzyloxyethyl)cyclohexyl]pyrrolidine (10.5 g, 36 mmol), and potassium carbonate (7.60 g, 55 mmol) in toluene (90 mL) and water (12 mL) is stirred and refluxed for 4 hours. The reaction mixture is cooled to room temperature and then diluted with 1N HCl aq. and ethyl acetate. The organic layer is washed with sat. NaHCO$_3$ aq., brine, dried over magnesium sulfate, filtered and concentrated to give 2-((R)-2-{4-[2-(benzyloxy)ethyl]cyclohexyl}pyrrolidin-1-yl)-6,7-difluoroquinoline-3-carbaldehyde as yellow syrup, which is used without further purification.

$^1$H-NMR (400 MHz, CDCl$_3$), δ (ppm): 0.77-1.00 (m, 2H), 1.07-1.20 (m, 2H), 1.30-1.43 (m, 1H), 1.49 (dt, 2H), 1.51-1.88 (m, 6H), 1.91-2.04 (m, 3H), 3.18-3.24 (m, 1H), 3.48 (t, 2H), 3.69 (dt, 1H), 4.49 (s, 2H), 4.66-4.73 (m, 1H), 7.24-7.35 (m, 5H), 7.40-7.47 (m, 2H), 8.31 (s, 1H), 10.12 (s, 1H).

Step 2:
A crude 2-((R)-2-{4-[2-(benzyloxy)ethyl]cyclohexyl}pyrrolidin-1-yl)-6,7-difluoroquinoline-3-carbaldehyde is dissolved with ethanol-THF (120 mL/20 mL) and treated with sodium borohydride (1.33 g, 36 mmol) at 5° C., and the resulting mixture is stirred at the same temperature for 30 min. After addition of sat. NH$_4$Cl aq. and ethyl acetate, the mixture is partially concentrated to remove ethanol. The mixture is extracted with EtOAc, and the organic layer is washed with brine, dried over magnesium sulfate, filtered and concentrated. The crude product is purified by silica gel column chromatography to give [2-((R)-2-{4-[2-(benzyloxy)ethyl]cyclohexyl}pyrrolidin-1-yl)-6,7-difluoroquinolin-3-yl]methanol as a yellow syrup.

$^1$H-NMR (400 MHz, CDCl$_3$), δ (ppm): 0.74-0.92 (m, 2H), 0.98-1.13 (m, 2H), 1.26-1.39 (m, 1H), 1.45 (dt, 2H), 1.55-1.82 (m, 7H), 1.90-2.04 (m, 2H), 2.44-2.49 (m, 1H), 3.26-3.33 (m, 1H), 3.45 (t, 2H), 3.60 (dt, 1H), 4.47 (s, 2H), 4.61-4.67 (m, 1H), 4.72 (dd, 1H), 4.87 (d, 1H), 7.23-7.33 (m, 5H), 7.37 (dd, 1H), 7.48 (dd, 1H), 7.93 (s, 1H).

Step 3:
Methaneslufonyl chloride (5.5 mL, 71 mmol) is added dropwise to a mixture of [2-((R)-2-{4-[2-(benzyloxy)ethyl]cyclohexyl}pyrrolidin-1-yl)-6,7-difluoroquinolin-3-yl]methanol (13.7 g, 28.5 mmol) and N,N-diisopropylethylamine (DIPEA, 12.4 mL, 71 mmol) in toluene (150 mL) at 5° C., and the reaction mixture is stirred at ambient temperature for 2 hours. To the mixture, water and ethyl acetate are added and the organic layer is washed with sat. NaHCO$_3$ aq, brine, dried over magnesium sulfate, filtered and concentrated in vacuo to give crude 2-((R)-2-{4-[2-(benzyloxy)ethyl]cyclohexyl}pyrrolidin-1-yl)-3-(chloromethyl)-6,7-difluoroquinoline. To a mixture of 2-((R)-2-{4-[2-(benzyloxy)ethyl]cyclohexyl}pyrrolidin-1-yl)-3-(chloromethyl)-6,7-difluoroquinoline and N-[3,5-bis(trifluoromethyl)benzyl]-N-(2-methyl-2H-tetrazol-5-yl)amine (13.9 g, 43 mmol) in DMF (120 mL) is added potassium tert-butoxide (4.80 g, 43 mmol) at 5° C. The resulting mixture is stirred for 1 hour at the same temperature. After adding sat. NH$_4$Cl aq., the mixture is extracted with ethyl acetate. The combined organic layer is washed with water, brine, dried over magnesium sulfate, filtrated, and concentrated. The resulting mixture is purified by silica gel column chromatography to give trans-N-[2-((R)-2-{4-[2-(benzyloxy)ethyl]cyclohexyl}pyrrolidin-1-yl)-6,7-difluoroquinolin-3-ylmethyl]-N-[3,5-bis(trifluoromethyl)benzyl](2-methyl-2H-tetrazol-5-yl)amine as a yellow amorphous.

$^1$H-NMR (400 MHz, CDCl$_3$), δ (ppm): 0.69-0.93 (m, 2H), 0.97-1.11 (m, 2H), 1.25-1.38 (m, 1H), 1.43-1.54 (m, 3H), 1.60-1.76 (m, 6H), 1.82-1.93 (m, 1H), 1.95-2.05 (m, 1H), 3.18-3.24 (m, 1H), 3.46 (t, 2H), 3.45-3.54 (m, 1H), 4.20 (s, 3H), 4.47 (s, 2H), 4.54 (d, 1H), 4.56 (d, 1H), 4.58-4.66 (m, 1H), 4.78 (d, 1H), 4.99 (d, 1H), 7.22 (dd, 1H), 7.26-7.34 (m, 5H), 7.47 (dd, 1H), 7.56 (s, 1H), 7.63 (s, 2H), 7.72 (s, 1H).

Example M

Preparation of N-[3-(bromomethyl)quinoxalin-2-yl]-N-(cyclopentylmethyl)ethylamine

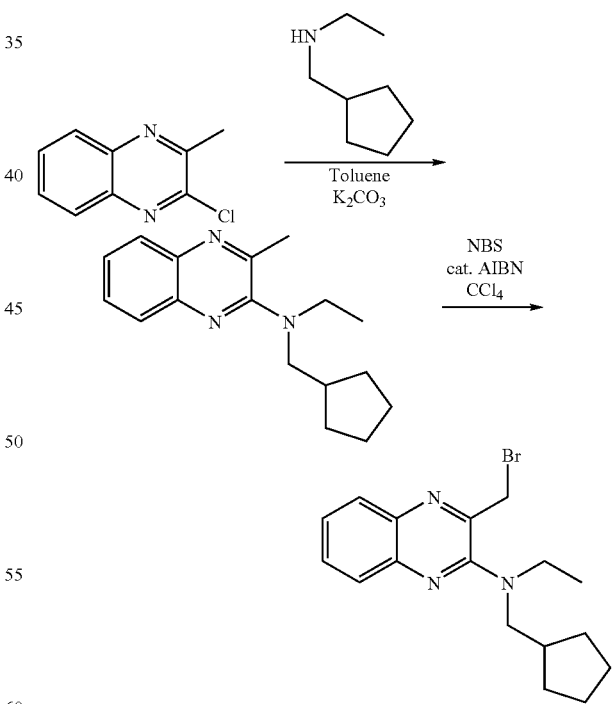

Step 1:
A suspension of 2-chloro-3-methylquinoxaline (500 mg, 2.8 mmol), N-(cyclopenthylmethyl)-N-ethylamine (900 mg, 7.1 mmol), potassium carbonate (970 mg, 7.0 mmol) in toluene (2.5 mL) is stirred at 150° C. for 14 hours. The reaction mixture is cooled to room temperature, diluted with water and ethyl acetate. The organic layer is washed with brine, dried over magnesium sulfate, filtered and concentrated. The crude product is purified by reverse phase HPLC (0.1% TFA to acetonitrile) to give N-(3-methylquinoxalin-2-yl)-N-(cyclopentylmethyl)ethylamine.

$^1$H-NMR (400 MHz, CDCl$_3$), δ (ppm): 1.15-1.20 (m, 2H), 1.19 (t, 3H), 1.45-1.73 (m, 8H), 2.21 (m, 1H), 2.69 (s, 3H), 3.37 (d, 2H), 3.39 (q, 2H), 7.47 (ddd, 1H), 7.55 (ddd, 1H), 7.79 (dd, 1H), 7.86 (dd, 1H).

Step 2:

A mixture of N-(3-methylquinoxalin-2-yl)-N-(cyclopentylmethyl)ethylamine (160 mg, 0.59 mmol), N-bromosuccinimide (130 mg, 0.73 mmol), and 2,2'-azobisisobtyronitrile (10 mg) in CCl$_4$ is stirred and refluxed for 1 hour. The reaction mixture is purified by silica gel column chromatography to give N-[3-(bromomethyl)quinoxalin-2-yl]-N-(cyclopentylmethyl)ethylamine. $^1$H-NMR (400 MHz, CDCl$_3$), δ (ppm): 1.10-1.25 (m, 2H), 1.22 (t, 3H), 1.45-1.73 (m, 8H), 2.22 (m, 1H), 3.42 (d, 2H), 3.49 (q, 2H), 4.73 (s, 2H), 7.51 (ddd, 1H), 7.62 (ddd, 1H), 7.81 (dd, 1H), 7.94 (dd, 1H).

Example N

Preparation of {5-[N-(cyclopentylmethyl)-N-ethylamino]-1-methyl-1H-pyrrolo[3,2-b]pyridin-6-yl}methanol

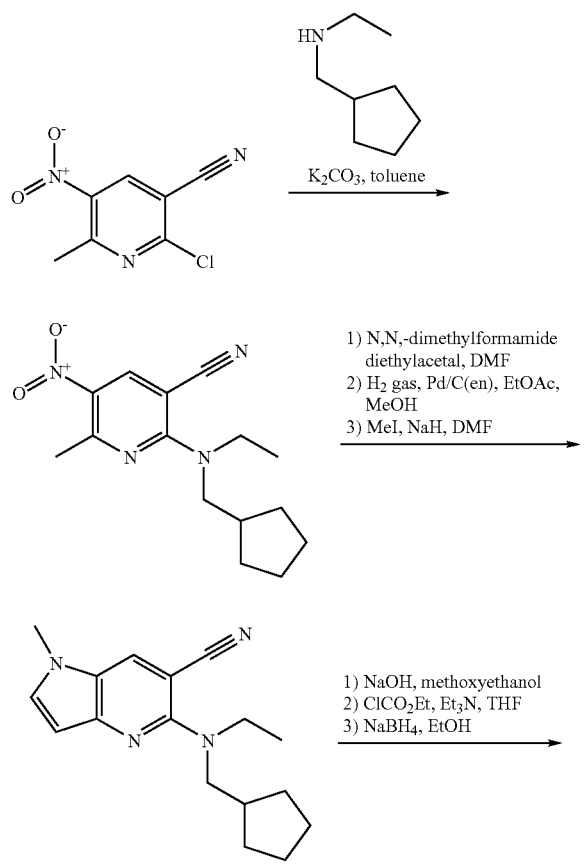

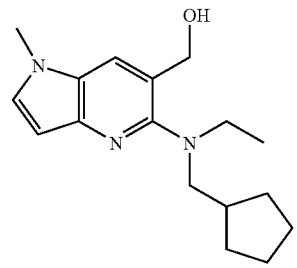

Step 1:

A mixture of 2-chloro-6-methyl-5-nitronicotinonitrile (997 mg, 5.05 mmol), N-(cyclopentylmethy)-N-ethylamine (770 mg, 6.05 mmol), and K$_2$CO$_3$ (1.7 g, 12.3 mmol) in toluene (20 mL) is heated to 110° C. After stirring for 3 hours, the reaction mixture is filtered to remove the resulting precipitate. The filtrate is diluted with EtOAc and washed with H$_2$O and brine. The organic layer is dried over sodium sulfate and concentrated in vacuo. The residue is purified by silica-gel column chromatography to give 2-[N-(cyclopentylmethyl)-N-ethylamino]-6-methyl-5-nitronicotinonitrile as orange oil.

$^1$H-NMR (400 MHz, CDCl$_3$), δδ (ppm): 1.30 (t, 3H), 1.22-1.33 (m, 2H), 1.55-1.64 (m, 2H), 1.65-1.76 (m, 2H), 1.75-1.85 (m, 2H), 2.32 (ddt, 1H), 2.78 (s, 3H), 3.77 (d, 2H), 3.88 (dd, 2H), 8.54 (s, 1H).

Step 2:

To a mixture of 2-[N-(cyclopentylmethyl)-N-ethylamino]-6-methyl-5-nitronicotinonitrile (1.22 g, 4.23 mmol) in DMF (10 mL) is added N,N-dimethylformamide diethyl acetal (1.09 mL, 6.35 mmol). After stirring at 85° C. for 30 min, the reaction mixture is cooled to room temperature and then H$_2$O is added. The mixture is extracted with EtOAc, dried over sodium sulfate and concentrated in vacuo. The resulting solid is rinsed with MeOH to give an orange solid. The solid is dissolved in MeOH (200 mL) and EtOAc (200 mL) and treated with Palladium-activated carbon ethylenediamine complex (Pd/C(en), 470 mg). The mixture is stirred under H$_2$ atmosphere for 2.5 hours at room temperature. The reaction mixture is filtered, and the filtrate is concentrated in vacuo. The residue is dissolved in EtOAc/Hexane and passed through a silica-gel pad. The resulting mixture is concentrated in vacuo, and the residue is dissolved in DMF (10 mL). To this mixture, NaH (0.54 g, 13.5 mmol) is added at 0° C., and after 30 min, iodomethane (0.28 mL, 4.50 mmol) is added. After stirring for 1 hour, the reaction is quenched with H$_2$O. The mixture is extracted with EtOAc and washed with brine. The organic layer is dried over sodium sulfate and concentrated in vacuo. The residue is purified by silica-gel column chromatography to give 5-[N-(cyclopentylmethyl)-N-ethylamino]-1-methyl-1H-pyrrolo[3,2-b]pyridine-6-carbonitrile as a colorless oil.

$^1$H-NMR (400 MHz, CDCl$_3$), δ (ppm): 1.19 (t, 3H), 1.16-1.26 (m, 2H), 1.44-1.55 (m, 2H), 1.56-1.66 (m, 2H), 1.67-1.75 (m, 2H), 2.24 (ddt, 1H), 3.46 (d, 2H), 3.58 (dd, 2H), 3.76 (s, 3H), 6.47 (d, 1H), 7.31 (d, 1H), 7.76 (s, 1H).

Step 3:

A solution of 5-[N-(cyclopentylmethyl)-N-ethylamino]-1-methyl-1H-pyrrolo[3,2-b]pyridine-6-carbonitrile (0.30 g, 1.06 mmol) in methoxyethanol (6 mL) is treated with 5N NaOH aq. (6 mL). The reaction mixture is stirred at 130° C. for 60 hours. After cooling to room temperature, the mixture is acidified with 1N HCl. The mixture is extracted with CH$_2$Cl$_2$, dried over sodium sulfate and concentrated in vacuo.

To a solution of the obtained residue in THF (5 mL) is added triethylamine (0.14 mL, 1.00 mmol) and ethyl chloroformate (0.10 mL, 1.00 mmol) at room temperature. After stirring for 1 h, the resulting precipitate is removed by filtration, and the filtrate is concentrated in vacuo. To a solution of the residue in EtOH (3 mL) is added sodium borohydride (41 mg, 1.08 mmol) at 0° C. After stirring for 1 h, the reaction is quenched with H$_2$O. The mixture is extracted with EtOAc and washed with brine. The organic layer is dried over sodium sulfate and concentrated in vacuo. The residue is purified by silica-gel column chromatography to give {5-[N-(cyclopentylmethyl)-N-ethylamino]-1-methyl-1H-pyrrolo[3,2-b]pyridin-6-yl}methanol as a colorless oil.

$^1$H-NMR (400 MHz, CDCl$_3$), δ (ppm): 1.08 (t, 3H), 1.14-1.23 (m, 2H), 1.42-1.50 (m, 2H), 1.71-1.79 (m, 2H), 2.01-2.10 (m, 2H), 3.12-3.22 (m, 4H), 3.78 (s, 3H), 4.87 (s, 2H), 5.98 (s, 1H), 6.60 (d, 1H), 7.21 (d, 1H), 7.42 (s, 1H).

Example O

Preparation of {5-[N-(cyclopentylmethyl)ethylamino]-1,3-dimethyl-1H-pyrrolo[3,2-b]pyridin-6-yl}methanol

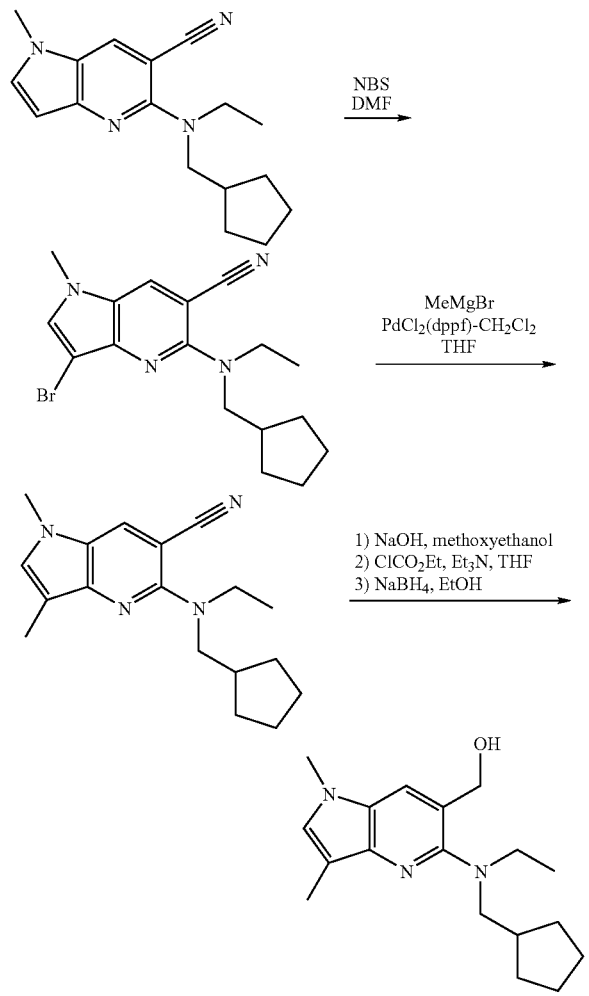

Step 1:
To a mixture of 5-[N-(cyclopentylmethyl)-N-ethylamino]-1-methyl-1H-pyrrolo[3,2-b]pyridine-6-carbonitrile (105 mg, 0.37 mmol) in DMF (2 mL) is added N-bromosuccinimide (NBS, 66 mg, 0.37 mmol) at 0° C. After stirring for 30 min, H$_2$O is added, and the reaction mixture is extracted with EtOAc. The organic layer is dried over sodium sulfate, concentrated and purified by silica-gel column chromatography to give 3-bromo-5-[N-(cyclopentylmethyl)-N-ethylamino]-1-methyl-1H-pyrrolo[3,2-b]pyridine-6-carbonitrile as a yellow solid.

$^1$H-NMR (400 MHz, CDCl$_3$), δ (ppm): 1.26 (t, 3H), 1.20-1.30 (m, 2H), 1.48-1.54 (m, 2H), 1.58-1.67 (m, 2H), 1.68-1.79 (m, 2H), 2.31 (ddt, 1H), 3.57 (d, 2H), 3.68 (d, 2H), 3.74 (s, 3H), 7.32 (s, 1H), 7.73 (s, 1H).

Step 2:
A mixture of 3-bromo-5-[N-(cyclopentylmethyl)-N-ethylamino]-1-methyl-1H-pyrrolo[3,2-b]pyridine-6-carbonitrile (1.05 g, 2.91 mmol) and [1,1-bis(diphenylphosphino)ferrocene]dichloropalladium (II) dichloromethane complex (PdCl$_2$(dppf)-CH$_2$Cl$_2$, 0.24 g, 0.29 mmol) in THF (20 mL) is treated with methylmagnesium bromide (0.93 M in THF, 7.8 mL) at 0° C. The reaction mixture is stirred at 75° C. for 22 hours. After cooling to room temperature, H$_2$O is added, and the reaction mixture is extracted with EtOAc. The organic layer is washed with sat. NaHCO$_3$ and brine, dried over sodium sulfate and concentrated. The residue is purified by silica-gel column chromatography to give 5-[N-(cyclopentylmethyl)-N-ethylamino]-1,3-dimethyl-1H-pyrrolo[3,2-b]pyridine-6-carbonitrile as a colorless oil.

$^1$H-NMR (400 MHz, CDCl$_3$), δ (ppm): 1.23 (t, 3H), 1.19-1.29 (m, 2H), 1.46-1.52 (m, 2H), 1.58-1.65 (m, 2H), 1.66-1.77 (m, 2H), 2.22-2.33 (m, 4H), 3.49 (d, 2H), 3.60 (dd, 2H), 3.68 (s, 3H), 7.09 (s, 1H), 7.68 (s, 1H).

Step 3:
{5-[N-(cyclopentylmethyl)ethylamino]-1,3-dimethyl-1H-pyrrolo[3,2-b]pyridin-6-yl}methanol is prepared from 5-[N-(cyclopentylmethyl)-N-ethylamino]-1,3-dimethyl-1H-pyrrolo[3,2-b]pyridine-6-carbonitrile following the procedure of example N (step 3).

$^1$H-NMR (400 MHz, CDCl$_3$), δ (ppm): 1.09 (t, 3H), 1.13-1.23 (m, 2H), 1.42-1.51 (m, 2H), 1.51-1.63 (m, 2H), 1.68-1.79 (m, 2H), 1.99-2.10 (m, 1H), 2.33 (s, 3H), 3.12-3.19 (m, 4H), 3.70 (s, 3H), 4.85 (s, 2H), 6.98 (s, 1H), 7.32 (s, 1H).

General HPLC (Ultra Performance liquid chromatography) Condition.
Column: Waters ACQUITY HPLC BEH C18, 1.7 μM
Mobile phase: CH$_3$CN/H$_2$O (0.1% TFA)

What is claimed is:
1. A compound of formula (I C):

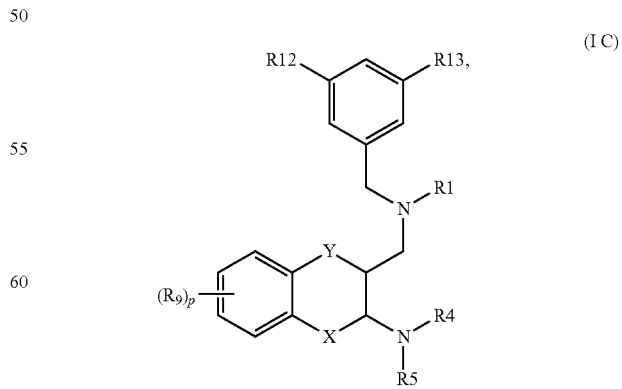

wherein X is N and Y is CH or N;
R$_1$ is 2-C$_1$-C$_7$-alkyl-2H-tetrazol-5-yl;

the element —N(R₄)(R₅) is pyrrolidine-1-yl which is substituted by one or two stubstituents selected from the group consisting of $C_1$-$C_7$-alkyl-, $C_3$-$C_7$-cycloalkyl-, $C_3$-$C_7$-cycloalkyl-methyl-, $C_1$-$C_7$-alkoxy-methyl-, hydroxy-$C_1$-$C_2$-alkyl-$C_3$-$C_7$-cycloalkyl-, formyl-$C_3$-$C_7$-cycloalkyl-, formyl-$C_1$-$C_2$-alkyl-$C_3$-$C_7$-cycloalkyl-, $HO_2C$—$C_3$-$C_7$-cycloalkyl-, $HO_2C$—$C_1$-$C_2$-alkyl-$C_3$-$C_7$-cycloalkyl-, $H_2NC(=O)$—$C_3$-$C_7$-cycloalkyl-, or $H_2NC(=O)$—$C_1$-$C_2$-alkyl-$C_3$-$C_7$-cycloalkyl-;

$R_9$ is one or two substituents selected from hydrogen, —CN, $C_1$-$C_7$-alkoxy, ($C_1$-$C_7$-alkyl)($C_1$-$C_7$-alkyl-)amine-, halo-$C_1$-$C_7$-alkyl, or halogen;

$R_{12}$ and $R_{13}$, independently of one another, is halo-$C_1$-$C_7$-alkyl or also halogen;

wherein p is 0, or 1 or 2; or $R_4$ is $(C_1$-$C_4)$alkyl- or $(C_3$-$C_5)$cycloalkyl-; and $R_5$ is $(C_3$-$C_7)$cycloalkyl-$(C_1$-$C_2)$alkyl- which is substituted by one to two substitutents selected from hydroxyl, alkoxy, $HO_2C$—, $HO_2C$—$(C_1$-$C_3)$alkyl-, hydroxy-$(C_1$-$C_3)$alkyl-, $(C_1$-$C_6)$alkoxy-carbonyl-, or $(C_1$-$C_6)$alkoxy-carbonyl-$(C_1$-$C_3)$alkyl-;

or a salt thereof.

2. A compound of formula (II):

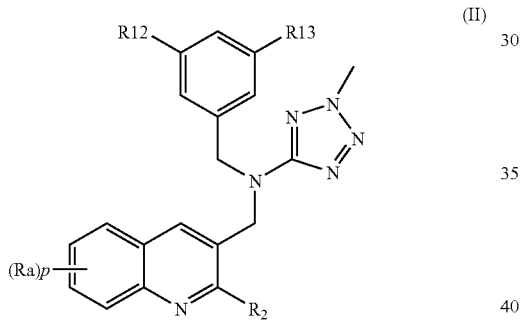

(II)

wherein p is 0, or 1 or 2;

Ra is halogen, or $(C_1$-$C_4)$-alkoxy, or halo-$(C_1$-$C_4)$alkyl;

$R_{12}$ and $R_{13}$ are independently halogen or halo-$(C_1$-$C_4)$alkyl;

$R_2$ is formula (III):

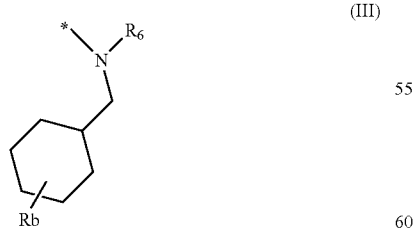

(III)

wherein $R_6$ is $(C_1$-$C_4)$alkyl- or $(C_3$-$C_5)$cycloalkyl-; Rb is —$(CH_2)_n$-Rc; n is 0, or 1, or 2, or 3, Rc is carboxy, hydroxy, $(C_1$-$C_4)$-alkoxy, or $(C_1$-$C_4)$-alkoxycarbonyl; or a salt thereof.

3. The compound according to claim 2 of formula (II):

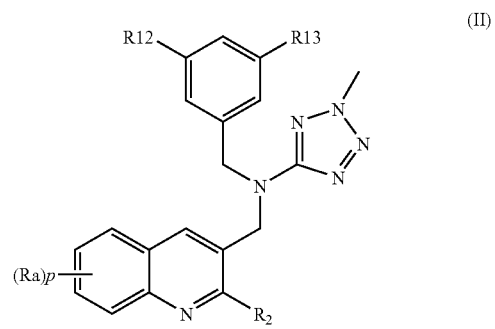

(II)

wherein p is 0, or 1 or 2;

Ra is halogen, or $(C_1$-$C_4)$-alkoxy, or halo-$(C_1$-$C_4)$alkyl;

$R_{12}$ and $R_{13}$ are independently halogen or halo-$(C_1$-$C_4)$alkyl;

$R_2$ is formula (IIIA):

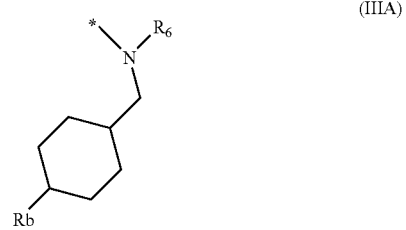

(IIIA)

wherein $R_6$ is $(C_1$-$C_4)$alkyl- or $(C_3$-$C_5)$cycloalkyl-; Rb is —$(CH_2)_n$-Rc; n is 0, or 1, or 2, or 3, Rc is carboxy, hydroxy, $(C_1$-$C_4)$-alkoxy, or $(C_1$-$C_4)$-alkoxycarbonyl; or a salt thereof.

4. A compound of formula (II):

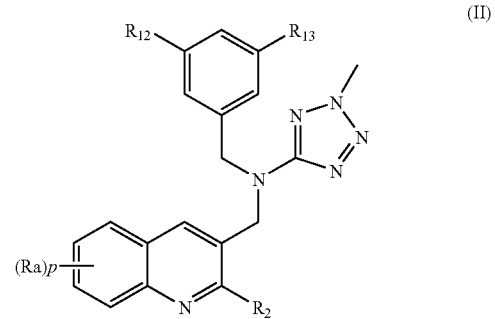

(II)

wherein p is 0, or 1, or 2, or 3;

Ra is halogen, or $(C_1$-$C_4)$-alkoxy, or halo-$(C_1$-$C_4)$alkyl;

$R_{12}$ and $R_{13}$ are independently halogen or halo-$(C_1$-$C_4)$alkyl;

$R_2$ is formula (IV):

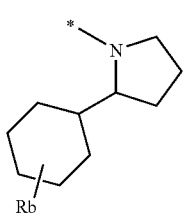

(IV)

wherein Rb is —$(CH_2)_n$-Rc; n is 0, or 1, or 2, or 3; Rc is carboxyl, hydroxy, formyl, $(C_1-C_4)$-alkoxy, $H_2NC(=O)$—, $H_2NC(=O)$—$(C_1-C_4)$alkyl, $(C_1-C_4)$-alkoxycarbonyl, or halo-$(C_1-C_4)$-alkoxycarbonyl; or a salt thereof.

5. The compound of claim 4, wherein $R_2$ is formula (IVA):

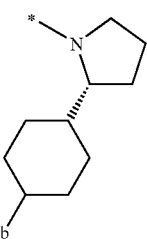

(IVA)

wherein Rb is —$(CH_2)_n$-Rc; n is 0, or 1, or 2, or 3; Rc is carboxyl, hydroxy, formyl, $(C_1-C_4)$-alkoxy, $H_2NC(=O)$—, $H_2NC(=O)$—$(C_1-C_4)$alkyl, $(C_1-C_4)$-alkoxycarbonyl, or halo-$(C_1-C_4)$-alkoxycarbonyl; or a salt thereof.

6. The compound of claim 5, wherein p is 1 or 2; Ra is halogen; $R_{12}$ and $R_{13}$ are halo-$(C_1-C_4)$alkyl; Rb is —$(CH_2)_n$-Rc, wherein n is 0 or 1; Rc is carboxyl, or $(C_1-C_4)$-alkoxycarbonyl, or halo-$(C_1-C_4)$-alkoxycarbonyl; or a pharmaceutically acceptable salt.

7. The compound according to claim 1 or 4 selected from

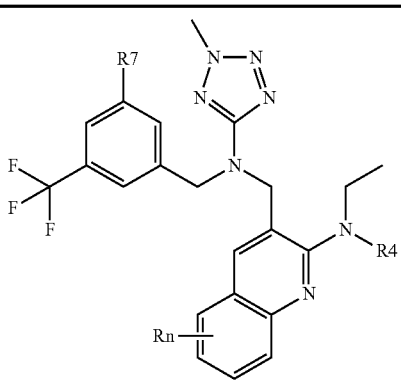

| No. | Rn | $R_4$ | $R_7$ |
|---|---|---|---|
| 15 | 6,7-$F_2$ | 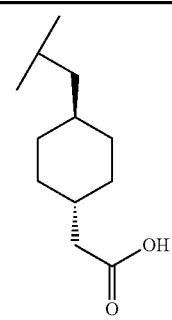 | $CF_3$ |

-continued

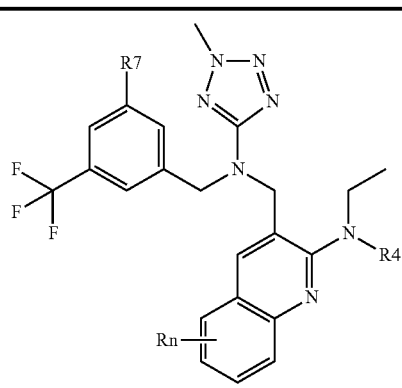

| No. | Rn | $R_4$ | $R_7$ |
|---|---|---|---|
| 17 | 6,7-$F_2$ | 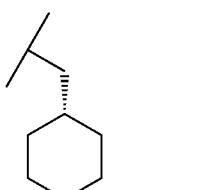 | $CF_3$ |
| 22 | 7-F | 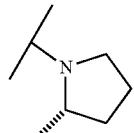 2-(R) | $CF_3$ |

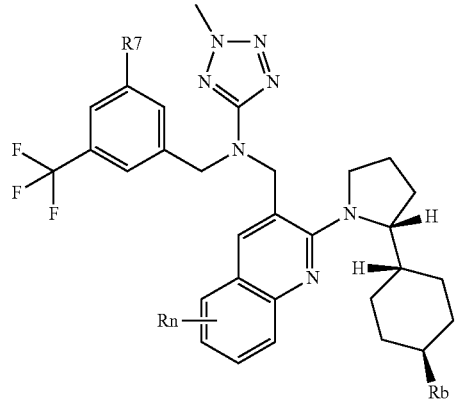

| No. | Rn | Rb | $R_7$ |
|---|---|---|---|
| 29 | 7-F | —$CH_2OH$ | $CF_3$ |
| 30 | 7-F | —$CH_2OH$ | Cl |
| 31 | 6,7-$F_2$ | —$CH_2OH$ | $CF_3$ |
| 32 | 6,7-$F_2$ | —$CH_2OH$ | Cl |

-continued

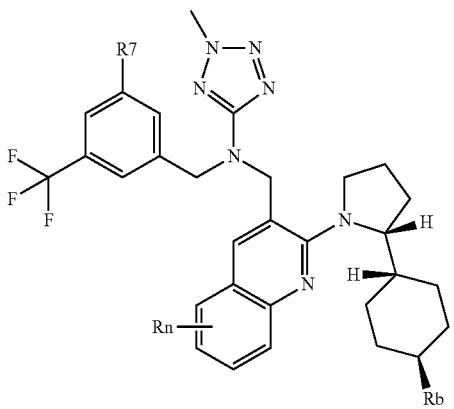

| No. | Rn | Rb | R7 |
|---|---|---|---|
| 33 | 7-F | —(CH$_2$)$_2$OH | CF$_3$ |
| 34 | 7-F | —(CH$_2$)$_2$OH | Cl |
| 35 | 6,7-F$_2$ | —(CH$_2$)$_2$OH | CF$_3$ |
| 36 | 6,7-F$_2$ | —(CH$_2$)$_2$OH | Cl |
| 37 | 7-F | —CHO | CF$_3$ |
| 38 | 7-F | —CHO | Cl |
| 39 | 6,7-F$_2$ | —CHO | CF$_3$ |
| 40 | 6,7-F$_2$ | —CHO | Cl |
| 41 | 7-F | —CH$_2$CHO | CF$_3$ |
| 42 | 7-F | —CH$_2$CHO | Cl |
| 43 | 6,7-F$_2$ | —CH$_2$CHO | CF$_3$ |
| 44 | 6,7-F$_2$ | —CH$_2$CHO | Cl |
| 45 | 7-F | —CO$_2$H | CF$_3$ |
| 46 | 7-F | —CO$_2$H | Cl |
| 47 | 6,7-F$_2$ | —CO$_2$H | CF$_3$ |
| 48 | 6,7-F$_2$ | —CO$_2$H | Cl |
| 49 | 7-F | —CH$_2$CO$_2$H | CF$_3$ |
| 50 | 7-F | —CH$_2$CO$_2$H | Cl |
| 51 | 6,7-F$_2$ | —CH$_2$CO$_2$H | CF$_3$ |
| 52 | 6,7-F$_2$ | —CH$_2$CO$_2$H | Cl |
| 53 | 6,7-F$_2$ | —C(=O)NH$_2$ | CF$_3$ |
| 54 | 6,7-F$_2$ | —CH$_2$C(=O)NH$_2$ | CF$_3$ | or, in each case, a salt thereof.

8. A pharmaceutical composition, comprising:
the compound according claim 1, 2 or 4 or pharmaceutically acceptable salts thereof and a pharmaceutically acceptable carrier.

9. The compound according to claim 1, 2 or 4 or a pharmaceutically acceptable salt thereof in combination with an active principles selected from the group consisting of a:
(i) HMG-Co-A reductase inhibitor or a pharmaceutically acceptable salt thereof,
(ii) angiotensin II receptor antagonist or a pharmaceutically acceptable salt thereof,
(ii) angiotensin converting enzyme (ACE) Inhibitor or a pharmaceutically acceptable salt thereof,
(iv) calcium channel blocker or a pharmaceutically acceptable salt thereof,
(v) aldosterone synthase inhibitor or a pharmaceutically acceptable salt thereof,
(vi) aldosterone antagonist or a pharmaceutically acceptable salt thereof,
(vii) dual angiotensin converting enzyme/neutral endopeptidase (ACE/NEP) inhibitor or a pharmaceutically acceptable salt thereof,
(viii) endothelin antagonist or a pharmaceutically acceptable salt thereof,
(ix) renin inhibitor or a pharmaceutically acceptable salt thereof,
(x) diuretic or a pharmaceutically acceptable salt thereof,
(xi) an ApoA-I mimic, and
(xii) a DGAT inhibitor.

10. A method for the treatment of atherosclerosis or dyslipidemia, comprising:
administering to a mammal, an effective amount of the compound according to claim 1, 2 or 4, or a pharmaceutically acceptable salt thereof.

* * * * *